(12) United States Patent
Antonelli

(10) Patent No.: US 9,739,423 B2
(45) Date of Patent: Aug. 22, 2017

(54) SYNTHESIS AND HYDROGEN STORAGE PROPERTIES OF NOVEL METAL HYDRIDES

(71) Applicant: University of South Wales Commercial Services Ltd., Wales (GB)

(72) Inventor: David Antonelli, Cardiff (GB)

(73) Assignee: UNIVERSITY OF SOUTH WALES COMMERCIAL SERVICES LTD., Wales (GB)

(*) Notice: Subject to any disclaimer, the term of this patent is extended or adjusted under 35 U.S.C. 154(b) by 0 days.

(21) Appl. No.: 14/737,759

(22) Filed: Jun. 12, 2015

(65) Prior Publication Data

US 2015/0362129 A1    Dec. 17, 2015

Related U.S. Application Data

(60) Provisional application No. 62/084,723, filed on Nov. 26, 2014, provisional application No. 62/011,817, filed on Jun. 13, 2014.

(51) Int. Cl.

| | | |
|---|---|---|
| C07F 11/00 | (2006.01) | |
| C07F 13/00 | (2006.01) | |
| C07F 9/00 | (2006.01) | |
| F17C 11/00 | (2006.01) | |
| C01B 3/00 | (2006.01) | |
| C01B 6/02 | (2006.01) | |
| H01M 4/38 | (2006.01) | |
| H01M 8/065 | (2016.01) | |

(52) U.S. Cl.
CPC ............ *F17C 11/007* (2013.01); *C01B 3/001* (2013.01); *C01B 3/0015* (2013.01); *C01B 3/0031* (2013.01); *C01B 3/0042* (2013.01); *C01B 6/02* (2013.01); *C07F 9/00* (2013.01); *C07F 11/00* (2013.01); *C07F 13/00* (2013.01); *H01M 4/383* (2013.01); *H01M 8/065* (2013.01); *Y02E 60/328* (2013.01)

(58) Field of Classification Search
CPC ... F17C 11/007; C01B 3/0042; C01B 3/0031; C01B 6/02; C01B 3/0015; C07F 9/00; C07F 11/00; C07F 13/00; H01M 8/065; H01M 4/383
USPC .......................... 556/12, 46; 423/648.1; 206/7
See application file for complete search history.

(56) References Cited

U.S. PATENT DOCUMENTS

| | | | |
|---|---|---|---|
| 5,906,792 A | 5/1999 | Schulz et al. | |
| 7,625,547 B2* | 12/2009 | Wolverton | ............ C01B 3/0026 252/182.32 |
| 2001/0051130 A1 | 12/2001 | Jensen et al. | |
| 2004/0105805 A1 | 6/2004 | Zidan | |
| 2004/0229090 A1 | 11/2004 | Davis et al. | |
| 2005/0180916 A1 | 8/2005 | Autrey et al. | |
| 2006/0003203 A1 | 1/2006 | Wang et al. | |
| 2007/0025908 A1 | 2/2007 | Sandrock et al. | |
| 2008/0138675 A1 | 6/2008 | Jang et al. | |
| 2009/0227808 A1 | 9/2009 | Kim et al. | |
| 2010/0022791 A1 | 1/2010 | Ihm et al. | |
| 2010/0036145 A1 | 2/2010 | Kim et al. | |
| 2010/0184595 A1 | 7/2010 | Vajo et al. | |
| 2010/0247424 A1 | 9/2010 | Mao et al. | |
| 2011/0201834 A1 | 8/2011 | Kim et al. | |
| 2013/0181162 A1 | 7/2013 | Antonelli | |
| 2014/0370406 A1* | 12/2014 | Antonelli | .............. H01M 8/065 429/421 |

FOREIGN PATENT DOCUMENTS

| | | |
|---|---|---|
| CN | 2861702 Y | 1/2007 |
| CN | 201233436 Y | 5/2009 |
| EP | 0283359 A1 | 9/1988 |
| EP | 0374015 A2 | 6/1990 |
| EP | 2098530 A1 | 9/2009 |
| EP | 2154105 A1 | 2/2010 |
| GB | 1577830 A | 10/1980 |
| JP | 2006298670 A | 11/2006 |
| JP | 201043082 | 2/2010 |
| JP | 2010503662 A | 2/2010 |
| KR | 20100031446 A | 3/2010 |
| WO | WO-2007015597 A1 | 2/2007 |
| WO | WO-2008032985 A1 | 3/2008 |
| WO | WO-2008094007 A1 | 8/2008 |
| WO | WO-2010072002 A1 | 7/2010 |
| WO | WO-2010085108 A2 | 7/2010 |
| WO | WO-2013088170 A1 | 6/2013 |

OTHER PUBLICATIONS

E. E.Krasovskii et al., Electronic Structure of Early Transition Metal Dihydrides and Hypothetical ScH3, TiH3 and VH3 Compounds, Int. J. Hydrogen Energy, 1995, vol. 20, No. 5, pp. 373-376.

Buyoung MA et al., Periodic Trends for Transition Metal Dihydrides MH2, Dihydride Dihydrogen Complexes MH2/H2, and Tetrahydrides MH4 (M=Ti, V, and Cr), J. Am. Chem. Soc., 1996, vol. 118, No. 4, pp. 870-879.

Alberola, et al., Bis[(Trimethylsilyl]Manganese: Structural Variations of Its Solvent-Free and TMEDA-, Pyridine-, and Dioxane-Complexed Forms, Organometallics, 2009, 28, 2112-2118.

Andersen, et al., Bis(Neopentyl)-, Bis(trimethylsilylmethyl)- and Bis(2-methyl-2-phenyl-propyl)-magnesium, J.C.S. Dalton, 1977, 809-811.

Andersen, et al., Neopentyl, Neophyl, and Trimethylsilylmethyl Compounds of Manganese, Manganese (II) Dialkyls; Manganese (II) Dialkyl Amine Adducts; Tetra-alkylmanganate(II) Ions and Lithium Salts, Manganese IV) Tetra-alkyls, J.C.S. Dalton, 1976, 2204-2211.

Andersen, et al., The Molecular Structure of Monomeric Base-Free Bis(neopentyl)manganese by Gas Electron Diffraction, J. Chem. Soc., Chem. Commun., 1985, 1807-1808.

(Continued)

*Primary Examiner* — Porfirio Nazario Gonzalez
(74) *Attorney, Agent, or Firm* — Blank Rome LLP

(57) ABSTRACT

The present disclosure relates to improved processes for the preparation of metal hydrides. The present disclosure also relates to metal hydrides, e.g., metal hydrides prepared by the processes described herein, that exhibit enhanced hydrogen storage capacity when used as hydrogen storage systems.

66 Claims, 59 Drawing Sheets

(56) References Cited

OTHER PUBLICATIONS

Andrews, Matrix Infrared Spectra and Density Functional Calculations of Transition Metal Hydrides and Dihydrogen Complexes, Chem. Soc. Rev., 2004, 33, 123-132.
Antonov, et al., Neutron Spectroscopy of y Manganese Hydride, Solid State Communications, 2000, 113:569-572.
Badding, et al., High-Pressure Chemistry of Hydrogren in Metals: In Situ Study of Iron Hydride, Science, 1991, 253, 421-424.
Balabanov, et al., Ab lnitio Study of Structure and Spectra of MnH2, MnH2-, and MnH3, J. Phys. Chem. A, 2002, 106, 6839-6843.
Barker, et al., Silylmethyl and Related Complexes, Part 6. Preparation, Properties, and Crystal and Molecular Structure of Trispis(trimethylsilypmethylFchromium(III); the Chemistry of Related Compounds of Titanium(III) Vanadium(III), Zirconium(IV), and Hafnium(IV), J.C.S. Dalton, 1978, 734-740.
Buijink, et al., Electron-Deficient Vanadium Alkyl Complexes: Synthesis and Molecular Structure of the Vanadium(III) Dinitrogen Complex [(Me3CCH2)3V]2(?-N2), Organometallics, 1993, 2004-2005.
Cahiez et al., Chemistry of Organomanganese(II) Compounds, Chem. Rev., 2009, 109:3, 1435-1476.
Cahiez, et al., Organomangaense(II) Reagents XVII: Preparation of Organomanganese Bromide Compounds in Either: An Efficient and Economic Alternative to Organomanganese Iodide Compounds for Synthetic Applications, Tetrahedron Letters, 1989, 30:27, 3545-3546.
Cahiez, et al., Reactivity of Organomanganese(II) Reagents: II. A New, Convenient Preparation of Alkyl, Alkenyl, and Alkynyl Ketones via Organomangaese(II) Iodides, Synthesis Communications, 1977, 130-133.
Cahiez, et al., Salt Effects on the Reactivity and the Stability of Organomanganese Reagents, Tetrahedron Letters, 1998, 39, 849-852.
Cantrell, Phase Composition and the Effect of Thermal Cycling for VHx, V0.995C0.005Hx, and V0.975Zr0.020C0.005Hx, J. Alloys and Compounds, Feb. 1999, 1-14, available online at http://hdl.handle.net/2014/17065.
Chertihin, et al., Infrared Spectra of FeH, FeH2, and FeH3 in Solid Argon, J. Phys. Chem., 1995, 99, 12131-12134.
Chertihin, et al., Reactions of Laser Ablated Ti Atoms with Hydrogen During Condensation in Excess Argon, Infrared Spectra of the TiH, TiH2, TiH3, and TiH4 Molecules, J. Am. Chem. Soc., 1994, 116, 8322-8327.
Coates, et al., Some t-Butylmagnesium and Related Complexes, Reactions Between Hydrides and Organomagnesium Compounds, J. Chem. Soc. (A), 1968, 514-518.
Dilts, et al., the Nature of Soluble Copper(I) Hydride, Journal of the American Chemical Society, 1968, 90:21, 5769-5772.
Dolgoplosk, et al., Preparation of E-Alkenyl and E-Organometallic Compounds of Transition Metals and Study of their Properties, Organic Chemistry, 1978, Plenum Publishing Corporation, 2315-2328.
Eckert, et al., IV.D.1 Hydrogen Storage Material with Binding Intermediate Between Physisorption and Chemisorption, FY 2007 Annual Progress Report, DOE Hydrogen-Program, 587-592.
El-Kurdi, Homoleptic Alkyl- and Aryl-Complexes of Transition Metals (Ti, Zr, Hf, Nb, and Cr) and Tetra-organyloxyvanadium-(V) and -(IV) Complexes, Inaugural-Dissertation, Dept. Biology, Chemistry and Pharmacy, Freie Universitat Berlin, Sep. 2010.
Fedotov, et al., Atomic Ordering in the hcp Cobalt Hydrides and Deuterides, Journal of Alloys and Compounds, 1999, 291, 1-7.
Fischer, et al., Reinvestigation of Arylmanganese Chemistry—Synthesis and Molecular Structures of [(thf)4Mg(☐-Cl)2Mn(Br)Mes], [Mes(thf)Mn(☐-Mes)]2, and (MnPh2)° (Ph = C6H5; Mes = Mesityl, 2,4,6-Me3C6H2), Journal of Organometallic Chemistry, 2009, 694, 1107-1111.
Friour, et al., Organomanganous Reagents: IX, Preparation of Various Halogenated, Alkoxylated, Aryloxylated, and Arylsulfenylated Ketones from Correspondingly Functionalized Carboxylic Acid Chlorides or Anyhdrides, Synthesis Communications, 1984, 37-40.
Gambarotta, et al., a Homoleptic Arylmanganese (II) Complex: Synthesis and Structure of a Thermally Stable Trinuclear Mesitylmanganese (II) Complex, J. Chem. Soc., Chem. Commun., 1983, 1128-1129.
Gamo, et al., Formation and Properties of Titanium-manganese Alloy Hydrides, International Journal of Hydrogen Energy, Elseview Science Publishers B.V., 1985, 10:1:39-47.
Goffrey, et al., Synthesis of Ligand-free Transition-metal Dibyrides in Low-temperature Matrixes: Manganese Dihydride, MnH2, Journal of the American Chemical Society, 1984, 106:3:807-809.
Hamaed et al., Hydride-Induced Amplification of Performance and Binding Enthalpies in Chromium Hydrazide Gels for Kubas-Type Hydrogen Storage, J. Am. Chem. Soc., 133, 15434-15443, 2011.
Hoang et al., Design and Synthesis of Vanadium Hydrazide Gels for Kubas-Type Hydrogen Adsorption: A New Class of Hydrogen Storage Materials, J. Am. Chem. Soc., 132(33), 11792-11798, 2010.
Hoang, et al., Observation of TiH5 and TiH7 in Bulk-Phase TiH3 Gels for Kubas-Type Hydrogen Storage, Chem. Matter., 2013, 25:4765-4771.
Hood, et al., Electronic Structure of Homoleptic Transition Metal Hydrides TiH4, VH4, CrH4, MnH4, FeH4, CoH4, and NiH4, J. Chem. Phys., 1979, 71:2:705-712.
International Search Report issued in PCT/EP2015/063237 dated Sep. 30, 2015.
International Search Report issued in PCT/GB2014/051825 on Oct. 8, 2014.
King, Structure and Bonding in Homelpetic Transition Metal Hydride Anions, Coordination Chemistry Reviews 2000, 200-202, 813-829.
Klose, et al., Insertion Reactions of Isocyanides and Nitriles into Unsupported Iron-Aryl Bonds: The Synthesis of a Dimeric Iron(II) Homeleptic Iminoacyl Complex, Organometallics, 1993, 12, 2414-2416.
Korsgen, et al., the Identification of the FeH2 Radical in the Gas Phase by Infrared Spectroscopy, J. Chem. Phys. 1996, 104:12, 4859-4861.
Korsgen, et al., the Infrared Spectrum of FeH2, Studied in the Gas Phase by Laser Magnetic Resonance, Journal of Chemical Physics, 1999, 110:8, 3861-3869.
Kyoi, et al., Novel Magnesium-Manganese Hydrides Prepared by the Gigapascal High Pressure Technique, Materials Transactions, 2002, 43:5:1124-1126.
Love, et al., a Non-Metallocene Hydride of Titanium(III), J. Chem. Soc., 1999, 121, 6843-6849.
Marinin, et al., Hydrogren Sorption Properties of Hexagonal Laves Phase TiMn1,5 Intermetallic Compound, 228-229.
Matuso, et al., First-principles Studies of Complex Hydride YMn2H6 and Its Synthesis from Metal Hydride YMn2H4.5, Applied Physics Letters, American Institute of Physics, 2011, 98:22:221908.
Meunier, et al., Synthesis and Characerization of Titanium Hydride Thin Films Obtained by Reactice Cathodic Sputtering, Materials Science and Engineering, 1993, B18, 303-307.
Miller, et al., Laser Photoelectron Spectroscopy of MnH2-, FeH2-, CoH2-, and NiH2-: Determination of the Electron Affinities for the Metal Dihydrides, J. Chem. Phys., 1996, 84:8, 4127-4131.
Morris, et al., on the Path to Bulk FeH2: Synthesis and Magnetic Properties of Amorphous Iron (II) Hydride, Journal of Alloys and Compounds, 2014, 590:199-204.
Morris, et al., Thermodynamically Neutral Kubas-type Hydrogen Storage Using Amorphous Cr(III) Alkyl Hydride Gels, Phys. Chem. Chem. Phys., 2015, 17:9480-9487.
Mowat, et al., Elimination Stabilized Alkyls, Part I. Chromium, Molybdenum, Tungsten and Vanadium, J.C.S. Dalton, 1972, 533-542.
Noh, et al., Rhenium Oxohalides: Synthesis and Crystal Structures of ReO3Cl(Thf)2, ReOCl4(Thf), Re203C16(Thf)2, and Re203C16(H20)2, the Royal Society of Chemistry, Dalt. Trans., 2007, 674-679.

(56) References Cited

OTHER PUBLICATIONS

Ozin, et al., Synthesis of Ligand-free Transition-metal Dihydrides in Low-temperature Matrixes: Manganese Dihydride MnH2, Journal of the American Chemical Society, 1984, 106:3:807-809.
Ozin, et al., The Photoreverisble Oxidative-Addition, Reductive-Elimination Reactions Fe + H2 FeH2 in Low-Temperature Martrices, J. Phys. Chem. 1984, 88, 645-648.
Pearse, et al., Band Spectrum of Manganese Hydride, MnH, 1937, 139:590.
Peddada, et al., Hydride Precipitation in Vapor Deposited Ti Thin Films, J. Mater. Res., 1993, 8:2, 291-296.
Rathman, et al., Amazing Base-Mesityllithium, MESLi, Fine, Specialty & Performance Chemicals, 2003, 6-8.
Richard, et al., Neopentyl, Neophyl, and Trimethylsilmethyl Compounds of Manganese, Manganese (II) dialkyls; Manganese (II) dialkyl amine Adducts; Tetra-alkylmangante (II) Ions and Lithium Salts; Manganese (IV) Tetra-alkyls, Journal of the Chemistry Society, 1976, 22042211.
Rubinovitz, et al., the Photochemical Fe + H2 Reaction in Ar and Kr Matrices by Irradiation in the Visible Region, J. Phys. Chem., 1986, 90, 1940-1944.
Sakintuna et al., Metal Hydride Materials for Solid Hydrogen Storage: a Review. International Journal of Hydrogen Energy, 32, 1121-1140, 2007.
Schulzke, et al., the Unusual Stability of Homoleptic Di- and Tetravalent Chromium Alkyls, Organometallics, 3810-3816, 2002.
Skipper et al., the Kubas Interaction in M(Ii) (M = Ti, V, Cr) Hydrazine-Based Hydrogen Storage Materials: a Dft Study, Dalton Trans., 41(28), 8515-8523, 2012.
Stepien, Formation of Cobalt Hydrides in Low Temperature Field Evaporation, Optica Applicata, 2005, XXXV:3, 363-368.
Takashi, Reaction of Titanium Trichloride with Amines, Notes, 1967, 40, 4, 9-1000.
Van Zee, et al., High Spin Molecules: Esr and Optical Spectroscopy of MnH (7↑) and MnH2 (6A1) at 4°K, J. Chem. Phys. 1978, 69:5, 1869-1875.
Van Zee, et al., MnF2 and MnH2 Molecules (S=5/2): "Extra" Lines in Their ESR Spectra, Chemical Physics Letters, 1979, 64:2, 325-327.
Wang, et al., Matrix Infrared Spectra and Density Functional Theory Calculations of Manganese and Rhenium Hydrides, J. Phys. Chem. A, 2003, 107, 4081-4091.
Zucchini, et al., Synthesis and Properties of Some Titanium and Zirconium Benzyl Derivatives, Journal of Organometallic Chemistry, 1971, 26, 357-372.

\* cited by examiner

SYNTHESIS AND HYDROGEN STORAGE PROPERTIES OF NOVEL METAL HYDRIDES

This application claims the benefit of U.S. Provisional Application Nos. 62/011,817, filed Jun. 13, 2014 and 62/084,723, filed Nov. 26, 2014, each of which is incorporated by reference in its entirety.

FIELD OF THE INVENTION

The present invention relates to improved processes for the preparation of metal hydrides. The present invention also relates to metal hydrides, e.g., metal hydrides prepared by the processes described herein, that exhibit enhanced hydrogen storage capacity when used as hydrogen storage systems.

BACKGROUND OF THE INVENTION

The enormous demands placed on the world's fossil fuel reserves have led to concerns regarding global warming, energy security and environmental pollution. Researchers continue to seek alternative fuel sources. Molecular hydrogen is ideal in this regard because it is lightweight, abundant, has more than three times the energy density by mass than currently used hydrocarbon fuels such as gasoline, and its only combustion product (water) is environmentally benign. Despite the advances made in fuel cell technology and hydrogen production, storage remains a great hurdle. See, e.g., R. H. Wiswall et al., *Science*, 186, 1158, 1974; S. Orimo et al., *Chem. Rev.*, 107, 4111, 2007, and L. K. Heung, On-board Hydrogen Storage System Using Metal Hydride, *HYPOTHESIS II*, 1, 1997. Using current technology, hydrogen storage has a low energy storage density by volume relative to hydrocarbon fuels. Therefore, with all other factors being equal, in order to store the same amount of energy, hydrogen storage requires a much larger and heavier storage tank than hydrocarbon fuel storage.

Gravimetric capacity is a measure of the amount of hydrogen that can be stored per unit mass of the storage system. Volumetric capacity is a measure of the amount hydrogen that can be stored per unit volume of the storage system. The United States Department of Energy (DOE) has set targets for hydrogen storage. The 2017 target set by the DOE for hydrogen storage is 5.5 wt. % and 40 kg/m$^3$ volumetric adsorption for a fully reversible system operating near room temperature. The ultimate goals are 7.5 wt % and 70 kg/m$^3$.

To date no technology has satisfied all the requirements set out by the DOE. Some technologies being considered involve the use of chemical carriers such as alloys, adsorbents such as amorphous carbons (see, e.g., R. Yang et al., *J. Am. Chem. Soc.*, 131, 4224, 2009), zeolites (see, e.g., A. Pacula, et al., *J. Phys. Chem. C*, 112, 2764, 2008) and metal organic frameworks (MOFs) (see, e.g., K. M. Thomas, *Dalton Trans.*, 1487, 2009; S. S. Kaye et al., *J. Am. Chem. Soc.*, 129, 14176, 2007, and N. L. Rosi et al., *Science*, 300, 1127, 2003).

The use of metal hydrides, such as LiH and NaAlH$_4$ is thwarted by heat management issues and problems with slow kinetics and/or reversibility. For example, when hydrogen reacts with magnesium or a sodium-aluminum alloy to give a metal hydride such as MgH$_2$ and NaAlH$_4$, significant amounts of heat are given off. When this heat is produced, a cooling step must be carried out to prevent a significant rise in temperature in the system, and this cooling step constitutes an energy loss to the system. Furthermore, heating is typically necessary to remove the hydrogen when required. This is an artifact of the high enthalpies of hydrogen binding (>60 kJ/mol) typical of hydrides such as MgH$_2$ and NaAlH$_4$.

Compression techniques have been used to increase gas pressure and improve the energy storage density by volume for hydrogen. This allows for the storage tanks to be smaller. However, compressing hydrogen requires a significant amount of energy, often accounting for as much as 30% of the stored energy. Furthermore, large pressure vessels are required for such compression techniques.

Another technique for storing hydrogen involves converting hydrogen gas to liquid hydrogen. This technique requires cryogenic storage because hydrogen has a very low boiling point (−252.88° C.). The liquefaction of hydrogen requires a large amount of energy to maintain these extremely low temperatures. Furthermore, the storage tank for liquid hydrogen requires complex and expensive insulation in order to prevent the liquid hydrogen from evaporating. In addition, liquid hydrogen has a lower energy density by volume than hydrocarbon fuels, such as gasoline, by a factor of about 4.

Physisorption materials, such as amorphous carbons and metal organic frameworks (MOFs), achieve promising storage capacities at temperatures of 77 K, but typically lose approximately 90% of their performance at room temperature due to low heats of adsorption (typically 5-13 kJ/mol H$_2$). See, e.g., A. Dailly et al., *J. Phys. Chem. B*, 110, 1099, 2006, J. Rowsell et al., *Angew. Chem., Int. Ed.*, 2005, 4670, 2005. In order to achieve the DOE target under ambient conditions, the ideal H$_2$ binding energy is predicted to be in the range of 20-30 kJ/mol per hydrogen molecule. See, e.g., R. Lochan et al., *Phys. Chem. Chem. Phys.*, 8, 1357, 2006. Moreover, energy production costs for the preparation of hydrogen storage materials may be an important factor.

There is, therefore, a need for improved, lower cost materials that can be used as hydrogen storage systems. Additionally, there is a need for improved methods to synthesize materials of higher purity that exhibit enhanced hydrogen storage capacity when used as hydrogen storage systems.

SUMMARY OF THE INVENTION

In one aspect, the inventor has surprisingly developed an improved process for the preparation of metal hydride compounds useful in hydrogen storage applications. The improved process involves thermal precipitation of a metal hydrocarbon compound (e.g., a metal alkyl or metal aryl compound) in the absence of hydrogen followed by hydrogenation of the resulting precipitate. The inventor has surprisingly found that the thermal precipitation process forms an intermediate containing residual hydrocarbon, in what is believed to be, without wishing to be bound by theory, bridging modes. Again, without wishing to be bound by theory, the inventor theorizes that the precipitation process may form a polymer by α-elimination (e.g., α-elimination of tetramethylsilane in the case of a bis[(trimethylsilyl)methyl] compound) to form a bridging alkylidene structure or, in the case of a metal aryl compound, by condensation via bimolecular C—H activation and subsequent hydrocarbon elimination (i.e., bimolecular sigma bond metathesis). It is believed that these bridging ligands create space in the downstream amorphous structure, effectively acting as templates to ensure that hydrogen can diffuse in and out of the structure once the bridging hydrocarbon is removed. Hydrogenation of the precipitate subsequently removes the residual hydrocarbon. Again, without wishing to be bound by theory, the inventor theorizes that the resulting metal hydride contains bridging hydride ligands.

The metal hydrides described herein, such as those prepared by the processes described herein, surprisingly exhibit enhanced hydrogen storage capacity and permit the metal centres to form interactions (e.g., Kubas interactions) with multiple $H_2$ molecules to form solid state hydrides, such as the hydrides $MH_x$ (e.g., M=titanium, vanadium, chromium, manganese, iron, cobalt, nickel or copper) wherein x is about 4 to about 13 (such as about 4.5 to about 13 or about 4.6 to about 13) e.g., $MH_4$, $MH_5$, $MH_6$, $MH_7$, $MH_8$, $MH_9$, $MH_{10}$, $MH_{11}$, $MH_{12}$ or $MH_{13}$ (e.g., $MH_5$, $MH_6$, $MH_5$, $MH_8$, $MH_9$, $MH_{10}$, $MH_{11}$, $MH_{12}$ or $MH_{13}$) and can reversibly release hydrogen, thereby acting as materials for hydrogen storage.

The metal hydrides described herein are stable as bulk solids at room temperature (i.e., exhibit low pyrophoricity and reduced air sensitivity), which are important features for practical hydrogen storage.

In one aspect, the present invention relates to a process for preparing a metal hydride (e.g., a metal hydride suitable for hydrogen storage applications). In one embodiment, the process comprises:

(i) heating an alkyl or aryl transition metal compound (or a combination thereof) in a solvent (e.g., an organic solvent) in the absence of hydrogen to form a precipitate;
(ii) optionally isolating the precipitate;
(iii) hydrogenating the precipitate; and
(iv) optionally isolating the hydrogenated precipitate.

In one embodiment, the alkyl or aryl transition metal compound has the formula $M^1R$, $M^1R_2$, $M^1R_3$ or $M^1R_4$ (or a combination thereof), wherein:

$M^1$ is a transition metal; and
each R group is, independently, selected from alkyl, silylated alkyl, alkenyl, arylalkyl, heteroaryl and aryl. In a preferred embodiment, R is silylated alkyl or aryl.

In one embodiment, R does not contain a β-hydrogen substituent (e.g., an organic alkyl group without a β-hydrogen substituent, such as mesityl, neopentyl, trimethylsilylmethyl or benzyl). The starting alkyl or aryl transition metal compound may be monomeric, dimeric, trimeric, tetrameric or polymeric.

In one embodiment, $M^1$ is selected from titanium, vanadium, chromium, manganese, iron, cobalt, nickel and copper, and combinations thereof. In another embodiment, $M^1$ is selected from titanium, vanadium, chromium, manganese, iron, cobalt, and nickel, and combinations thereof. In yet another embodiment, $M^1$ is selected from vanadium, manganese and chromium, and combinations thereof.

In one embodiment, the product of step (i) contains greater than about 10% by weight, such as greater than about 20%, greater than about 30%, greater than about 40% or greater than about 50% by weight of residual hydrocarbon. In another embodiment, the product of step (i) contains less than about 50% by weight, such as less than about 40%, less than about 30%, less than about 20% or less than about 10% by weight of residual hydrocarbon.

In one embodiment, step (i) is conducted at a temperature of from about 5° C. to about 250° C., such as from about 50° C. to about 200° C., from about 75° C. to about 150° C., from about 80° C. to about 120° C., from about 90° C. to about 110° C. or from about 95° C. to about 105° C. In one embodiment, step (i) is conducted at about 100° C.

In one embodiment, step (i) is conducted for a period of time between about 12 hours and about 72 hours, for example, between about 24 hours and about 60 hours, such as for about 24 hours or for about 48 hours.

In one embodiment, step (i) is conducted at a temperature of from about 100° C. for a period of about 48 hours.

In one embodiment, step (i) is conducted in an aliphatic solvent such as a hydrocarbon solvent e.g., pentane, hexane, cyclohexane, heptane, octane, and combinations thereof. In one embodiment, step (i) is conducted in petroleum ether. In one embodiment, step (i) is conducted in an aromatic solvent (e.g., toluene). Preferably, the solvent in step (i) is anhydrous. In one embodiment, step (i) is a solution prior to formation of the desired precipitate.

In one embodiment, step (ii) comprises filtering the product of step (i). In another embodiment, step (ii) comprises filtering the product of step (i) followed by drying the resulting solid (e.g., under vacuum, at a temperature of between about 50° C. and 200° C., such as between about 100° C. and 150° C., for example, at about 100° C., optionally, for a period of time between about 1 and about 10 hours, such as between about 2 and 6 hours, for example, about 4 hours). In one embodiment, step (ii) comprises filtering the product of step (i) followed by drying the resulting solid in vacuo at a temperature of about 100° C. for about four hours.

In one embodiment, the hydrogenation in step (iii) is conducted at a hydrogen pressure of between about 1 bar and about 200 bar, such as between about 25 bar and about 150 bar, about 50 bar and about 125 bar, about 50 bar and about 100 bar, or about 60 bar to about 80 bar. In additional embodiments, the hydrogenation in step (iii) is conducted at a hydrogen pressure of about 1 bar, about 5 bar, about 10 bar, about 15 bar, about 20 bar, about 25 bar, about 30 bar, about 40 bar, about 50 bar, about 60 bar, about 70 bar, about 80 bar, about 90 bar, or about 100 bar. In one embodiment, the hydrogenation in step (iii) is conducted at a hydrogen pressure of about 70 bar.

In one embodiment, step (iii) is conducted at a temperature of from about 10° C. to about 200° C., such as from about 10° C. to about 100° C., from about 15° C. to about 50° C., from about 20° C. to about 40° C., from about 20° C. to about 30° C. In one embodiment, step (iii) is conducted at about 25° C. In one embodiment step (iii) is conducted at room temperature. In one embodiment step (iii) is conducted without heating or cooling.

In one embodiment, step (iii) is conducted for a period of time between about 12 hours and about 72 hours, for example, between about 24 hours and about 60 hours, such as for about 48 hours. In another embodiment, step (iii) is conducted for a period of time between about 1 day and about 7 days, e.g., for about 2 days, about 3 days, about 4 days, about 5 days, about 6 days or about 7 days.

In one embodiment, step (iii) is conducted at a temperature of about 25° C. and a hydrogen pressure of about 70 bar for about 48 hours.

In one embodiment, step (iii) is conducted in the absence of solvent. In another embodiment step (iii) is conducted in an aliphatic solvent, such as a hydrocarbon solvent e.g., petroleum ether, pentane, cyclohexane, hexane, heptane, octane, and combinations thereof. In one embodiment, step (iii) is conducted in an aromatic solvent (e.g., toluene). Preferably, the solvent in step (iii) is anhydrous.

In one embodiment, the process comprises step (ii) (i.e., step (ii) is not optional and forms part of the process). In another embodiment the process comprises step (iv) (i.e., step (iv) is not optional and forms part of the process). In a preferred embodiment, the process comprises steps (i)-(iv) (i.e., steps (ii) and (iv) are not optional and form part of the process).

In another embodiment, the process further comprises (v), subjecting the product of step (iii) (or step (iv) if performed) to one or more (such as about 5 or more, about 10 or more, about 20 or more, about 30 or more, about 40 or more or about 50 or more) hydrogen adsorption-desorption cycles.

In one embodiment of step (v), hydrogen adsorption-desorption cycles may be conducted at a hydrogen pressure of between about 1 bar and about 250 bar, between about 1 bar and about 200 bar, between about 50 bar and about 170 bar, between about 100 bar and about 150 bar or between about 120 bar and about 150 bar. In additional embodiments, the hydrogenation in step (v) is conducted at a hydrogen pressure of about 1 bar, about 5 bar, about 10 bar, about 15 bar, about 20 bar, about 25 bar, about 30 bar, about 40 bar, about 50 bar, about 60 bar, about 70 bar, about 80 bar, about 90 bar, about 100 bar, about 125 bar or about 150 bar.

In another aspect, the present invention relates to a process for preparing a metal hydride of Formulas I or II as described below, wherein the process comprises the steps described in any of the embodiments set forth above.

In another aspect, the present invention relates to a metal hydride (e.g., a metal hydride suitable for hydrogen storage applications, such as any of the metal hydrides described herein) prepared by a process according to any of the embodiments described herein. In another aspect, the present invention relates to a metal hydride (e.g., a metal hydride suitable for hydrogen storage applications, such as any of the metal hydrides described herein) prepared by a process according to any of the embodiments described herein, wherein the metal hydride is capable of absorbing hydrogen ($H_2$) in an amount of at least 4.0% (e.g., from about 4.0% to about 12.0%, from about 5.0% to about 12.0%, or higher) (based upon 100% total weight of the metal hydride without hydrogen stored in it).

In another aspect, the present invention relates to a metal hydride of the formula (I):

$$M^1(M^2)_z H_x R_y L_n \qquad (I)$$

wherein $M^1$ is a first metal selected from titanium, vanadium, chromium, iron, cobalt, nickel, copper, and, optionally, mixtures thereof;

$M^2$ is one or more additional metals, which have a total content of z (e.g., one or more doping metals, such as, e.g., zinc, gallium, zirconium, niobium, molybdenum, technetium, ruthenium, rhodium, palladium, silver, cadmium, hafnium, tantalum, tungsten, rhenium, osmium, iridium, platinum, gold, and mercury);

R, if present, is an organic group (e.g., an organic group that does not contain a β-hydrogen substituent);

L is a Lewis base (e.g., an organic solvent (such as an ether solvent, e.g., $Et_2O$, dioxane, THF), water, $H_2S$, an amine, a phosphine, a sulfide, an olefin (e.g., 1-hexene), and combinations thereof);

n is 0 to about 1 (e.g., 0 to about 0.8, 0 to about 0.6, 0 to about 0.5, 0 to about 0.4, 0 to about 0.2, 0 to about 0.1, 0 to about 0.05 or 0 to about 0.01);

y is 0 to about 0.5, and z is 0 to about 1 (e.g., 0 to about 0.9, 0 to about 0.8, 0 to about 0.7, 0 to about 0.6, 0 to about 0.5, 0 to about 0.4, 0 to about 0.3, 0 to about 0.2, 0 to about 0.1 or 0 to about 0.05);

wherein when $M^1$ is Ti or V, x is about 4.6 to about 13;
when $M^1$ is Cr, x is about 4.6 to about 12;
when $M^1$ is Fe, x is about 4.6 to about 10;
when $M^1$ is Ni or Co, x is about 4.6 to about 8;
when $M^1$ is Cu, x is about 4.6 to about 6.

In one embodiment, $M^1$ is selected from titanium, vanadium, chromium, iron, and mixtures thereof. In one embodiment, $M^1$ is selected from titanium, vanadium, chromium, and mixtures thereof. In one embodiment, $M^1$ is selected from vanadium, chromium, and mixtures thereof.

In a further embodiment, x is about 8.6 to about 13, about 8.6 to about 12, about 8.6 to about 11 or about 8.6 to about 10.

In one embodiment, $M^1$ is Ti and x is greater than 7 (e.g., about 7.5 to about 13, about 8 to about 13, about 9 to about 13, about 10 to about 13, about 11 to about 13 or about 12 to about 13). For example $M^1$ is Ti and x is about 7.5 to about 8.5, about 8.5 to about 9.5, about 9.5 to about 10.5, about 10.5 to about 11.5, about 11.5 to about 12.5 or about 12.5 to about 13.

In one embodiment, $M^1$ is V and x is greater than 7 (e.g., about 7.5 to about 13, about 8 to about 13, about 9 to about 13, about 10 to about 13, about 11 to about 13 or about 12 to about 13). For example $M^1$ is V and x is about 7.5 to about 8.5, about 8.5 to about 9.5, about 9.5 to about 10.5, about 10.5 to about 11.5, about 11.5 to about 12.5 or about 12.5 to about 13.

In one embodiment, $M^1$ is Cr and x is greater than 6 (e.g., about 6.5 to about 12, about 7 to about 12, about 8 to about 12, about 9 to about 12, about 10 to about 12 or about 11 to about 12, a). For example $M^1$ is Cr and x is about 6.5 to about 7.5, about 7.5 to about 8.5, about 8.5 to about 9.5, about 9.5 to about 10.5, about 10.5 to about 11.5 or about 11.5 to about 12.

In one embodiment, $M^1$ is Fe and x is greater than 6 (e.g., about 6.5 to about 10, about 7 to about 10, about 8 to about 10 or about 9 to about 10). For example $M^1$ is Fe and x is about 6.5 to about 7.5, about 7.5 to about 8.5, about 8.5 to about 9.5 or about 9.5 to about 10.

In one embodiment, $M^1$ is Co and x is greater than 6 (e.g., about 6.5 to about 8 or about 7 to about 8). For example $M^1$ is Co and x is about 6.5 to about 7.5 or about 7.5 to about 8.

In one embodiment, $M^1$ is Ni and x is greater than 6 (e.g., about 6.5 to about 8 or about 7 to about 8). For example $M^1$ is Ni and x is about 6.5 to about 7.5 or about 7.5 to about 8.

In another aspect, the present invention relates to a metal hydride of the formula (II):

$$M^1(M^2)_z H_x R_y L_n (H_2)_a \qquad (II)$$

wherein $M^1$ is a first metal selected from titanium, vanadium, chromium, iron, cobalt, nickel, copper, and mixtures thereof;

$M^2$ is one or more additional metals (e.g., a metal other than titanium, vanadium, chromium, iron, cobalt, nickel, and copper), which have a total content of z (e.g., one or more doping metals, such as, e.g., zirconium, gallium, zinc, niobium, molybdenum, technetium, ruthenium, rhodium, palladium, silver, cadmium, hafnium, tantalum, tungsten, rhenium, osmium, iridium, platinum, gold, and mercury);

R, if present, is an organic group (e.g., an organic group that does not contain a β-hydrogen substituent);

L is a Lewis base (e.g., an organic solvent (such as an ether solvent, e.g., $Et_2O$, dioxane, and THF), water, $H_2S$, an amine, a phosphine, a sulfide, an olefin (e.g., 1-hexene), and combinations thereof);

n is 0 to about 1 (e.g., 0 to about 0.8, 0 to about 0.6, 0 to about 0.5, 0 to about 0.4, 0 to about 0.2, 0 to about 0.1, 0 to about 0.05 or 0 to about 0.01)

x is about 0.5 to about 4.5 (e.g., about 1.8 to about 4.2 or about 2 to about 4);

a is greater than 1 (such as greater than 2; such as about 3 to about 5, e.g., about 3, about 4 or about 5);

y is 0 to about 0.5, and z is 0 to about 1 (e.g., 0 to about 0.9, 0 to about 0.8, 0 to about 0.7, 0 to about 0.6, 0 to about 0.5, 0 to about 0.4, 0 to about 0.3, 0 to about 0.2, 0 to about 0.1 or 0 to about 0.05);

In one embodiment, a is about 2 to about 5 (e.g., about 2, about 3, about 4 or about 5). In one embodiment, a is about 3 to about 5 (e.g., about 3, about 4 or about 5). In one embodiment, a is about 3. In one embodiment, a is about 4. In one embodiment, a is about 5.

In one embodiment, $M^1$ is Ti, x is about 3 and a is about 3 to about 5 (e.g., about 3, about 4 or about 5).

In one embodiment, $M^1$ is V, x is about 3 and a is about 3 to about 5 (e.g., about 3, about 4 or about 5).

In one embodiment, $M^1$ is Cr, x is about 2 and a is about 3 to about 5 (e.g., about 3, about 4 or about 5).

In one embodiment, $M^1$ is Fe, x is about 2 and a is about 3 to about 5 (e.g., about 3, about 4 or about 5).

In one embodiment, $M^1$ is Co, x is about 2 and a is about 3.

In one embodiment, $M^1$ is Ni, x is about 2 and a is about 3.

In another aspect, the present invention relates to a metal hydride of the formula (III):

$$M^1(M^2)_zH_xR_yL_n \qquad (III)$$

wherein $M^1$ is a first metal selected from titanium, vanadium, chromium, iron, cobalt, nickel, copper, and, optionally, mixtures thereof;

$M^2$ is one or more additional metals, which have a total content of z (e.g., one or more doping metals, such as, e.g., zinc, gallium, zirconium, niobium, molybdenum, technetium, ruthenium, rhodium, palladium, silver, cadmium, hafnium, tantalum, tungsten, rhenium, osmium, iridium, platinum, gold, and mercury);

R, if present, is an organic group (e.g., an organic group that does not contain a β-hydrogen substituent);

L is a Lewis base (e.g., an organic solvent (such as an ether solvent, e.g., $Et_2O$, dioxane, THF), water, $H_2S$, an amine, a phosphine, a sulfide, an olefin (e.g., 1-hexene), and combinations thereof);

n is 0 to about 1 (e.g., 0 to about 0.8, 0 to about 0.6, 0 to about 0.5, 0 to about 0.4, 0 to about 0.2, 0 to about 0.1, 0 to about 0.05 or 0 to about 0.01);

y is 0 to about 0.5;

z is between greater than 0.2 and about 1 (e.g., about 0.25 to about 1, about 0.25 to about 0.9, about 0.25 to about 0.8, about 0.25 to about 0.7, about 0.25 to about 0.6, about 0.25 to about 0.5, about 0.25 to about 0.4, about 0.25 to about 0.3); and x is about 0.5 to about 4.5 (e.g., about 2.5 to about 4.5, about 0.5 to about 3.6 or about 0.5 to about 3.3).

In one embodiment of the metal hydride of formula (III), one or more of (such as 2, 3 or 4) of the following apply (i) when $M^1$ is vanadium, x is at least 2.4; (ii) when $M^1$ is copper, x is at least 1.0, (iii) when $M^1$ is titanium, x is at least 2.4 and/or (iv) when $M^1$ is nickel, x is at least 1.6.

In one embodiment of any of the metal hydrides of described herein, y is less than about 0.4, such as less than about 0.3, less than about 0.2, less than about 0.1 or less than about 0.05. In one embodiment, y is 0 to about 0.4, such as 0 to about 0.3, 0 to about 0.25, 0 to about 0.2, 0 to about 0.1, or 0 to about 0.05.

In one embodiment of any of the metal hydrides described herein, R, if present, is, independently selected from alkyl, silylated alkyl, alkenyl, arylalkyl, heteroaryl and aryl. In a preferred embodiment, R, if present, is silylated alkyl or aryl.

In one embodiment of any of the metal hydrides described herein, hydrogenation and/or dehydrogenation of the metal hydride is thermodynamically neutral, such as when averaged over the bulk sample. For example, the net enthalpy changes associated with either the process of hydrogen adsorption and/or the process of hydrogen desorption, such as when averaged over the bulk sample, are close to 0 kJ $mol^{-1}$ $H_2$.

For example, in one embodiment, any of the metal hydrides described herein adsorb and/or desorb hydrogen at an absolute value of about 0 to about ±3 kJ $mol^{-1}$ $H_2$, such as at about 0 to about ±2.5 kJ $mol^{-1}$ $H_2$, about 0 to about ±2 kJ $mol^{-1}$ $H_2$, about 0 to about ±1.5 kJ $mol^{-1}$ $H_2$, about 0 to about ±1 kJ $mol^{-1}$ $H_2$, about 0 to about ±0.5 kJ $mol^{-1}$ $H_2$ or about 0 to about ±0.25 kJ $mol^{-1}$ $H_2$.

In another embodiment, any of the metal hydrides described herein adsorb and/or desorb hydrogen at an absolute value of about ±0.5 to about ±3 kJ $mol^{-1}$ $H_2$, such as at about ±0.5 to about ±2.5 kJ $mol^{-1}$ $H_2$, about ±0.5 to about ±2 kJ $mol^{-1}$ $H_2$, about ±0.5 to about ±1.5 kJ $mol^{-1}$ $H_2$, about ±0.5 to about ±1 kJ $mol^{-1}$ $H_2$, or about ±0.5 to about ±0.75 kJ $mol^{-1}$ $H_2$.

In another embodiment, any of the metal hydrides described herein adsorb and/or desorb hydrogen at an absolute value of about ±1 to about ±3 kJ $mol^{-1}$ $H_2$, such as at about ±1 to about ±2.5 kJ $mol^{-1}$ $H_2$, about ±1 to about ±2 kJ $mol^{-1}$ $H_2$, about ±1 to about ±1.5 kJ $mol^{-1}$ $H_2$, or about ±1 to about ±1.25 kJ $mol^{-1}$ $H_2$.

In another embodiment, any of the metal hydrides described herein adsorb and/or desorb hydrogen at an absolute value of about ±1.5 to about ±3 kJ $mol^{-1}$ $H_2$, such as at about ±1.5 to about ±2.5 kJ $mol^{-1}$ $H_2$, about ±1.5 to about ±2 kJ $mol^{-1}$ $H_2$, or about ±1.5 to about ±1.75 kJ $mol^{-1}$ $H_2$.

In another embodiment, any of the metal hydrides described herein adsorb and/or desorb hydrogen at an absolute value of less than about ±4 kJ $mol^{-1}$ $H_2$, such as less than about ±3.75 kJ $mol^{-1}$ $H_2$, less than about ±3.5 kJ $mol^{-1}$ $H_2$, less than about ±3.25 kJ $mol^{-1}$ $H_2$, less than about ±3 kJ $mol^{-1}$ $H_2$, less than about ±2.75 kJ $mol^{-1}$ $H_2$, less than about ±2.5 kJ $mol^{-1}$ $H_2$, less than about ±2.25 kJ $mol^{-1}$ $H_2$, less than about ±2 kJ $mol^{-1}$ $H_2$, less than about ±1.75 kJ $mol^{-1}$ $H_2$, less than about ±1.5 kJ $mol^{-1}$ $H_2$, less than about ±1.25 kJ $mol^{-1}$ $H_2$, less than about ±1 kJ $mol^{-1}$ $H_2$, less than about ±0.75 kJ $mol^{-1}$ $H_2$, less than about ±0.5 kJ $mol^{-1}$ $H_2$, less than about ±0.25 kJ $mol^{-1}$ $H_2$ or less than about ±0.1 kJ $mol^{-1}$ $H_2$.

In another embodiment, any of the metal hydrides described herein adsorb and/or desorb hydrogen at an absolute value of about ±3 kJ $mol^{-1}$ $H_2$, such as at about ±2.9 kJ $mol^{-1}$ $H_2$, about ±2.8 kJ $mol^{-1}$ $H_2$, about ±2.7 kJ $mol^{-1}$ $H_2$, about ±2.6 kJ $mol^{-1}$ $H_2$, about ±2.5 kJ $mol^{-1}$ $H_2$, about ±2.4 kJ $mol^{-1}$ $H_2$, about ±2.3 kJ $mol^{-1}$ $H_2$, about ±2.2 kJ $mol^{-1}$ $H_2$, about ±2.1 kJ $mol^{-1}$ $H_2$, about ±2 kJ $mol^{-1}$ $H_2$, about ±1.9 kJ $mol^{-1}$ $H_2$, about ±1.8 kJ $mol^{-1}$ $H_2$, about ±1.7 kJ $mol^{-1}$ $H_2$, about ±1.6 kJ $mol^{-1}$ $H_2$, about ±1.5 kJ $mol^{-1}$ $H_2$, about ±1.4 kJ $mol^{-1}$ $H_2$, about ±1.3 kJ $mol^{-1}$ $H_2$, about ±1.2 kJ $mol^{-1}$ $H_2$, about ±1.1 kJ $mol^{-1}$ $H_2$, about ±1 kJ $mol^{-1}$ $H_2$, about ±0.9 kJ $mol^{-1}$ $H_2$, about ±0.8 kJ $mol^{-1}$ $H_2$, about ±0.7 kJ $mol^{-1}$ $H_2$, about ±0.6 kJ $mol^{-1}$ $H_2$, about ±0.5 kJ $mol^{-1}$ $H_2$, about ±0.4 kJ $mol^{-1}$ $H_2$, about ±0.3 kJ $mol^{-1}$ $H_2$, about ±0.2 kJ $mol^{-1}$ $H_2$, or about ±0.1 kJ $mol^{-1}$ $H_2$.

In one embodiment of any of the metal hydrides described herein, the metal hydride is in the bulk phase. In one embodiment of any of the metal hydrides described herein, the metal hydride is polymeric, e.g., polymeric in the bulk phase.

In one embodiment, any of the metal hydrides described herein are mesoporous (e.g., have a pore diameter between about 0.5 and about 50 nm or between about 2 and about 50 nm). In another embodiment, any of the metal hydrides described herein are microporous (e.g., have a pore diameter less than about 2 nm, such as less than about 1 nm). In one embodiment, any of the metal hydrides described have a pore diameter of about 2 nm.

In one embodiment, any of the metal hydrides described herein have a porosity of between about 5 and about 80%, such as between about 5 and about 70%, between about 5 and about 60%, between about 5 and about 50%, between about 5 and about 40%, between about 5 and about 30% or between about 5 and about 20%.

In one embodiment, any of the metal hydrides described herein are amorphous or substantially amorphous (e.g., with little (e.g., nanoscopic order) or no long range order in the position of the atoms in the hydride structure). In one embodiment, any of the metal hydrides described herein contain less than about 20% crystallinity, such as less than about 10%, less than about 5%, less than about 2.5%, less than about 1%, less than about 0.5% crystallinity, or less than about 0.1% crystallinity as measured, for example, by X-ray diffraction using a Cu Kα radiation (40 kV, 40 mA) source.

In another embodiment, any of the metal hydrides described herein (e.g., a metal hydride of formula (I), (II) or (III)) exhibit one or more (such as two or three) of the following properties: (i)R, when present in the metal hydride, is bound to the metal center by a carbon atom (such as a single carbon atom) in the R group, (ii) the metal hydride is stable as a bulk solid at room temperature and (iii) the metal hydride is capable of reversibly absorbing and releasing hydrogen.

In one embodiment, the present invention relates to a composition comprising one or more metal hydrides of the formula (I):

$$M^1(M^2)_z H_x R_y L_n \qquad (I)$$

wherein each $M^1$ is, independently, a first metal selected from titanium, vanadium, chromium, iron, cobalt, nickel, copper, and, optionally, mixtures thereof;

each $M^2$ is, independently, one or more additional metals, which have a total content of z (e.g., one or more doping metals, such as, e.g., zinc, gallium, zirconium, niobium, molybdenum, technetium, ruthenium, rhodium, palladium, silver, cadmium, hathium, tantalum, tungsten, rhenium, osmium, iridium, platinum, gold, and mercury);

each R, if present, is, independently, an organic group (e.g., an organic group that does not contain a β-hydrogen substituent);

each L is, independently, a Lewis base (e.g., an organic solvent (such as an ether solvent, e.g., $Et_2O$, dioxane, and THF), water, $H_2S$, an amine, a phosphine, a sulfide, an olefin (e.g., 1-hexene), and combinations thereof);

each n is, independently, 0 to about 1 (e.g., 0 to about 0.8, 0 to about 0.6, 0 to about 0.5, 0 to about 0.4, 0 to about 0.2, 0 to about 0.1, 0 to about 0.05 or 0 to about 0.01);

each y is, independently, 0 to about 0.5; and each z is, independently, 0 to about 1 (e.g., 0 to about 0.9, 0 to about 0.8, 0 to about 0.7, 0 to about 0.6, 0 to about 0.5, 0 to about 0.4, 0 to about 0.3, 0 to about 0.2, 0 to about 0.1 or 0 to about 0.05);

wherein when $M^1$ is Ti or V, x is about 4.6 to about 13;

when $M^1$ is Cr, x is about 4.6 to about 12;

when $M^1$ is Fe, x is about 4.6 to about 10 when $M^1$ is Ni or Co, x is about 4.6 to about 8;

when $M^1$ is Cu, x is about 4.6 to about 6.

In another embodiment, the present invention relates to a composition comprising one or more metal hydrides of the formula (II):

$$M^1(M^2)_z H_x R_y L_n (H_2)_a \qquad (II)$$

wherein each $M^1$ is, independently, a first metal selected from titanium, vanadium, chromium, iron, cobalt, nickel, copper, and mixtures thereof;

each $M^2$ is, independently, one or more additional metals (e.g., a metal other than titanium, vanadium, chromium, iron, cobalt, nickel, and copper), which have a total content of z (e.g., one or more doping metals, such as, e.g., zirconium, gallium, zinc, niobium, molybdenum, technetium, ruthenium, rhodium, palladium, silver, cadmium, hathium, tantalum, tungsten, rhenium, osmium, iridium, platinum, gold, and mercury);

each R, if present, is, independently, an organic group (e.g., an organic group that does not contain a β-hydrogen substituent);

each L is, independently, a Lewis base (e.g., an organic solvent (such as an ether solvent, e.g., $Et_2O$, dioxane, and THF), water, $H_2S$, an amine, a phosphine, a sulfide, an olefin (e.g., 1-hexene), and combinations thereof);

each n is, independently, 0 to about 1 (e.g., 0 to about 0.8, 0 to about 0.6, 0 to about 0.5, 0 to about 0.4, 0 to about 0.2, 0 to about 0.1, 0 to about 0.05 or 0 to about 0.01);

each x is, independently, about 0.5 to about 4.5 (e.g., about 1.8 to about 4.2 or about 2 to about 4);

each a is, independently, greater than 1 (such as greater than 2; such as about 3 to about 5, e.g., about 3, about 4 or about 5);

each y is, independently, 0 to about 0.5, and each z is, independently, z is 0 to about 1 (e.g., 0 to about 0.9, 0 to about 0.8, 0 to about 0.7, 0 to about 0.6, 0 to about 0.5, 0 to about 0.4, 0 to about 0.3, 0 to about 0.2, 0 to about 0.1 or 0 to about 0.05).

In another embodiment, the present invention relates to a composition comprising one or more metal hydrides of the formula (I) and one or more metal hydrides of the formula (II):

$$M^1(M^2)_z H_x R_y L_n \qquad (I)$$

$$M^1(M^2)_z H_x R_y L_n (H_2)_a \qquad (II)$$

wherein each $M^1$ is, independently, a first metal selected from titanium, vanadium, chromium, iron, cobalt, nickel, copper, and mixtures thereof;

each $M^2$ is, independently, one or more additional metals (e.g., a metal other than titanium, vanadium, chromium, iron, cobalt, nickel, and copper), which have a total content of z (e.g., one or more doping metals, such as, e.g., zirconium, gallium, zinc, niobium, molybdenum, technetium, ruthenium, rhodium, palladium, silver, cadmium, hathium, tantalum, tungsten, rhenium, osmium, iridium, platinum, gold, and mercury);

each R, if present, is, independently, an organic group (e.g., an organic group that does not contain a β-hydrogen substituent);

each L is, independently, a Lewis base (e.g., an organic solvent (such as an ether solvent, e.g., $Et_2O$, dioxane, and THF), water, $H_2S$, an amine, a phosphine, a sulfide, an olefin (e.g., 1-hexene), and combinations thereof);

each n is, independently, 0 to about 1 (e.g., 0 to about 0.8, 0 to about 0.6, 0 to about 0.5, 0 to about 0.4, 0 to about 0.2, 0 to about 0.1, 0 to about 0.05 or 0 to about 0.01);

each y is, independently, 0 to about 0.5; and each z is, independently, z is 0 to about 1 (e.g., 0 to about 0.9, 0 to about 0.8, 0 to about 0.7, 0 to about 0.6, 0 to about 0.5, 0 to about 0.4, 0 to about 0.3, 0 to about 0.2, 0 to about 0.1 or 0 to about 0.05) wherein for a metal hydride of the formula (I):

when $M^1$ is Ti or V, x is about 4.6 to about 13;

when $M^1$ is Cr, x is about 4.6 to about 12;

when $M^1$ is Fe, x is about 4.6 to about 10 when $M^1$ is Ni or Co, x is about 4.6 to about 8; and when $M^1$ is Cu, x is about 4.6 to about 6;

and for a metal hydride of the formula (II):

each x is, independently, about 0.5 to about 4.5 (e.g., about 1.8 to about 4.2 or about 2 to about 4); and each a is, independently, greater than 1 (such as greater than 2; such as about 3 to about 5, e.g., about 3, about 4 or about 5)

In another embodiment, the present invention relates to a method of storing hydrogen, the method comprising:

providing a metal hydride according to any of the embodiments described herein (e.g., one or more metal hydrides of formula (I) or (II), or any mixture thereof);

adding hydrogen to the metal hydride; and allowing the hydrogen to coordinate to (e.g., be absorbed by) the metal hydride.

In another embodiment, the present invention relates to a method of storing hydrogen in a storage system, the method comprising:

providing a metal hydride according to any of the embodiments described herein (e.g., one or more metal hydrides of formula (I) or (II), or any mixture thereof) in a system;

adding hydrogen to the metal hydride in the storage system; and allowing the hydrogen to coordinate to (e.g., be absorbed by) the metal hydride in the storage system.

In one embodiment, the hydride is compacted into a pellet form, optionally with a binder and/or lubricant (e.g., amorphous carbon, paraffin, mineral oil, or a polymer such as cellulose or polypropylene) or other material (e.g., an inorganic compound such as $TiO_2$, a metal or a metal alloy such as Ni to facilitate the pelletization process). The binder, lubricant and/or other material may be incorporated at this stage to minimize the effects of poisoning, hydrolysis or other potentially adverse reaction induced by contaminants in the hydrogen supply to the material in its final form. Additional additives (e.g., porous carbons, metal organic frameworks (MOFs) and covalent organic frameworks (COFs)) may also be added to accelerate the rate at which the hydrogen is adsorbed and desorbed by the metal hydrides described herein. In one embodiment, the hydride is deposited in the macropores of a honeycomb-structured support.

The storage system (e.g., storage tank) tank may comprise one or more openings in a wall of the storage system. Fluids, such as hydrogen gas, can pass into and out of the storage tank through the one or more openings. The system may further comprise one or more valves which control the passage of fluids through the one or more openings. The one or more valves can be used to release pressure inside the storage tank by opening said one or more valves and allowing fluids to pass out of the storage tank through the one or more openings. The system may also further comprise a compressor (e.g., a gas compressor) for adding hydrogen into the storage system.

In additional embodiments, the method of storing hydrogen further comprises releasing the hydrogen from the metal hydride (e.g., a metal hydride in a storage system). In one embodiment, the hydrogen is released from the metal hydride by reducing the pressure of the hydrogen in the storage system. In one embodiment, the hydrogen is released from the metal hydride by changing (e.g., increasing) the temperature of the storage system.

Yet another embodiment of the present invention relates to a hydrogen storage system comprising a storage system and a metal hydride within the storage system, wherein the metal hydride is encompassed by any of the embodiments described herein (e.g., a metal hydride of formulas (I) and (II)).

The metal hydrides of the present invention may be useful in other applications, such as, but not limited to, methane adsorption, compressed natural gas storage, propellants, battery technologies, fuel cells, sorbents, olefin polymerization catalysts and sensors. The metal hydrides of the present invention may also be useful in other applications, such as, but not limited to, propelling electric and/or hybrid vehicles, and storing electricity while connected to the electrical grid. In one embodiment, the present invention relates to a storage system (which can be of any size and be stationary or mobile) for producing energy in conjunction with a fuel-cell, the storage system comprising a metal hydride according to any embodiment described herein within the storage system.

A propellant is a material that is used to move or propel an object, such as a jet or rocket. A propellant may comprise a fuel and an oxidizer. The fuel may be, for example, gasoline, jet fuel or rocket fuel. When the metal hydrides of the present invention are used in a propellant, the propellant further comprises hydrogen. The hydrogen may coordinate to a metal center present in the metal hydride of the present invention. In one embodiment, the hydrogen is in liquid form. In a preferred embodiment, the propellant further comprises an oxidizer, for example, liquid oxygen. In one embodiment, the propellant is used to propel a jet or a rocket. In another embodiment, it is used in conjunction with an oxidixer in a flame-producing device such as, e.g., a welding torch.

A battery comprises one or more electrochemical cells, which convert stored chemical energy into electrical energy. The metal hydrides of the present invention may be used to coordinate to and store a compound in a battery. In a preferred embodiment, the compound that is stored is hydrogen. In one embodiment, the battery converts energy stored in the hydrogen into electrical energy. In one embodiment, the metal hydrides of the present invention are used in conjunction with a fuel cell for generating electricity.

A sorbent is a material that is used to absorb a liquid or a gas. The metal hydrides of the present invention may be used as a sorbent to absorb a liquid or a gas. For example, the metal hydrides of the present invention may be used to absorb hydrogen. In one embodiment, the hydrogen is liquid form. In another embodiment, the hydrogen is in the form of a gas.

Another embodiment is a catalyst system for polymerization of olefins comprising a metal hydride of the present invention. The catalyst system may further comprise a support.

Yet another embodiment is a process comprising polymerizing or copolymerizing olefins (e.g., ethylene, propylene) carried out in the presence of a catalyst system of the present invention.

A sensor is used to detect a substance or to measure a physical quantity. The sensor gives a signal that the substance has been detected or gives a signal representing the measurement of the physical quantity. The signal can be read by an observer or by an instrument.

The metal hydrides of the present invention may be used in a sensor. For example, the metal hydrides of the present invention may be used to detect hydrogen, e.g., in a system. In one embodiment, the metal hydrides of the present invention measure the amount of hydrogen that is present in a system. In one embodiment, the hydrogen is in liquid form. In another embodiment, the hydrogen is in the form of a gas.

The metal hydrides of the present invention may be used for propelling electric and/or hybrid vehicles or for storing electricity while connected to the electrical grid.

In another aspect, the present invention relates to a battery or fuel cell comprising a metal hydride according to any embodiment described herein.

In another aspect, the present invention relates to a storage system for producing electricity using a fuel-cell or heat using an oxidant, comprising a storage system and a metal hydride according to any embodiment described herein.

In another aspect, the present invention relates to a storage system for a gas selected from hydrogen, methane and compressed natural gas comprising a storage system and a metal hydride according to any embodiment described herein.

In another aspect, the present invention relates to a storage system for producing electricity using a fuel-cell or heat using an oxidant, comprising a storage system and a metal hydride according to any embodiment described herein within the storage system.

DETAILED DESCRIPTION OF THE INVENTION

Definitions

Figure 1:
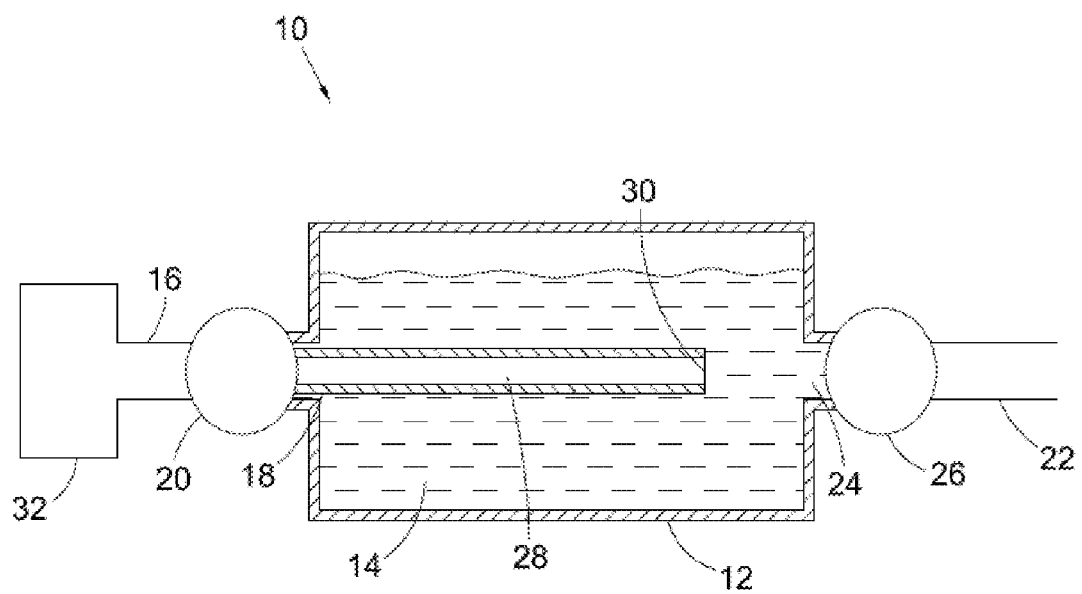
FIG. 1 depicts an embodiment of a storage system useful in the present invention.

Unless defined otherwise, all technical and scientific terms used herein generally have the same meaning as commonly understood by one of ordinary skill in the art to which this invention belongs.

The term "comprising" is open ended and, in connection with a composition, refers to the elements recited. The term "comprising" as used in connection with the compositions described herein can alternatively cover compositions "consisting essentially of" or "consisting of" the recited components.

The term "coordinate" as used here is not limited to a specific type of interaction between a metal center and hydrogen. For example, in one embodiment, the interaction between a metal center and hydrogen is a Kubas interaction.

The term "Kubas interaction" refers to hydrogen bound in a non-dissociative manner as a dihydrogen molecule to a transition metal center. In a Kubas interaction, free d-electrons of a metal centre interact with hydrogen. Specifically, where the metal centre has a low coordination number, the dihydrogen shares both of its α-bonding electrons with the metal centre, and the metal centre back donates electrons by overlap of its π symmetry d-orbital with the empty antibonding σ* empty orbital of the dihydrogen. This results in a lengthening of the H—H bond (without rupture) and a shift to a lower wavenumber for the H—H resonance (see, e.g. *J. Am. Chem. Soc.*, 119, 9179-9190, 1997).

Without wishing to be bound by theory, the inventor theorizes that one or more (such as 2 or more, such as 3, 4 or 5) H$_2$ molecules interact with the metal centers by Kubas interactions to form metal hydrides of the formula MH$_x$ in which x can be approximately an even number, e.g., about 4, about 6, about 8, about 10 or about 12. However, bimolecular and/or free radical processes may also occur leading to metal hydrides of the formula MH$_x$ in which x can approximately an odd number, e.g., about 3, about 5, about 7, about 9, about 11 or about 13. Additionally, mixed metal hydrides, in which variable x is a non integer may also be formed by continuous (not stepwise) adsorption.

The term "substantially free" as used herein means containing less than about 2 wt %, such as less than about 1 wt %, less than about 0.5 wt %, less than about 0.1 wt %, less than about 0.05 wt %, less than about 0.01 wt %, less than about 0.005 wt % or less than about 0.001 wt % of a specified element or compound.

The term "organic group" refers to any carbon containing group that may be present in a in a metal hydride of Formulas (I) and (II). For example, the organic group may be a solvent used in the formation of the metal hydride that has not been fully removed during the synthesis process. Another example of an organic group may be a ligand (e.g., trimethylsilylmethyl, mesityl, benzyl or neopentyl) that is not fully removed from the metal center during formation of the metal hydride. The organic group may also be a compound (e.g., a protic compound, such as methanol) that is added to the metal hydride in order to increase microporosity of the metal hydride structure (e.g., by forming bridging methoxide ligands within the structure), thereby facilitating H$_2$ moving in and out of the metal hydride.

As used herein, in one embodiment the term "thermodynamically neutral" refers to the net enthalpy changes associated with either the process of hydrogen adsorption and/or the process of hydrogen desprotion when averaged over the whole metal hydride sample. For example, the net enthalpy changes associated with either the process of hydrogen adsorption and/or the process of hydrogen desprotion, when averaged over the bulk sample, are close to 0 kJ mol$^{-1}$ H$_2$. Typically, hydrogen adsorption on a microscopic basis exhibits a range of enthalpies between about −5 and −70 kJ mol$^{-1}$ H$_2$. Without wishing being bound to theory, the inventor theorizes that the energy required by external pressure to open up binding sites in the metal hydride is approximately equal and opposite to the exothermic M-H bond forming process, resulting in effective enthalpy buffering and thermodynamic neutrality. Also without being bound to theory, the inventor theorizes that the energy required to open up the hydrogen binding sites in the metal hydrides described herein is provided by the gradually increasing external pressure of the hydrogen, which is roughly equal and opposite in value to the energy involved in hydrogen binding to the metal enters resulting in thermodynamic neutrality, and can be rationalised by the energy required to twist the amorphous structure into a conformation favourable for hydrogen binding. See, e.g., Skipper et al., *J. Phys. Chem. C*, 116, 19134, 2002.

As used herein, the term "alkyl" refers to a straight or branched chain saturated hydrocarbon moiety. In one embodiment, the alkyl group is a straight chain saturated hydrocarbon. Unless otherwise specified, the "alkyl" or "alkylene" group contains from 1 to 24 carbon atoms. Representative saturated straight chain alkyl groups include, e.g., methyl, ethyl, n-propyl, n-butyl, n-pentyl, and n-hexyl. Representative saturated branched alkyl groups include, e.g., isopropyl, sec-butyl, isobutyl, tert-butyl, neopentyl, and isopentyl. In a preferred embodiment, an "alkyl" group does not contain a β hydrogen substituent.

As used herein, the term "aryl" refers to an aromatic hydrocarbon (mono- or multi-cyclic) having from 6 to 24 carbon atoms (e.g., phenyl, naphthyl), bound to the metal center via a metal-carbon bond.

As used herein, the term "arylalkyl" refers to an alkyl-aryl group, wherein alkyl and aryl are as defined herein (e.g., benzyl).

As used herein, the term "heteroaryl" refers to an aromatic group (mono- or multi-cyclic) having from 5 to 24 carbon atoms, additionally containing one or more N, S or O atoms.

One of ordinary skill in the art will readily understand that a metal hydride having a non-integral stoichiometry, such as MH$_{4.2}$, refers to a material having metal (M) atoms coordinated with varying amounts of hydrogen (e.g., an average of 9 parts MH$_4$ to 1 part MnH$_6$). Additionally, any metal hydride defined herein having an integral stoichiometry of metal to hydride ligand (e.g., MH$_x$) is intended to also cover a metal hydride sample having an overall mixed stoichiometry of MH$_{(x-0.2\ to\ x+0.2)}$ (e.g., MH$_{10.8-11.2}$ or MH$_{11.8-12.25}$ for MH$_{11}$ and MH$_{12}$, respectively).

Metal Hydrides

In one embodiment, any of the metal hydrides described herein has a BET surface area of less than about 5 m$^2$/g, such as less than about 4 m$^2$/g, such as less than about 3 m$^2$/g, less than about 2 m$^2$/g, less than about 1.5 m$^2$/g or less than about 1.0 m$^2$/g, such as about 0.6 m$^2$/g.

In another embodiment, any of the metal hydrides described herein has a BET surface area of about 2 m$^2$/g or greater, such as about 5 m$^2$/g or greater, about 7.5 m$^2$/g or greater, about 10 m$^2$/g or greater, about 25 m$^2$/g or greater, about 50 m$^2$/g or greater, about 75 m$^2$/g or greater, about 100 m$^2$/g or greater, about 150 m$^2$/g or greater, about 200 m$^2$/g or greater, about 250 m$^2$/g or greater, about 275 m$^2$/g or greater, about 300 m$^2$/g or greater, about 350 m$^2$/g or greater, about 400 m$^2$/g or greater, about 450 m$^2$/g or greater or about 500 m$^2$/g or greater. For example, the metal hydride has a BET surface area of about 377 m$^2$/g or 391 m$^2$/g.

In other embodiments, the BET surface area is from about 2 m$^2$/g to about 1000 m$^2$/g, such as from about 10 m$^2$/g to about 750 m$^2$/g, from about 50 m$^2$/g to about 500 m$^2$/g, from about 100 m$^2$/g to about 500 m$^2$/g, from about 250 m$^2$/g to about 500 m$^2$/g, from about 300 m$^2$/g to about 500 m$^2$/g. In one embodiment, the BET surface area is from about 300 m$^2$/g to about 400 m$^2$/g.

In one embodiment, the metal hydrides described herein are in the form of a gel. In one embodiment, the metal hydrides described herein are in the form of a solid (e.g., a powder). In one embodiment, any of the metal hydrides described herein is a bulk solid, for example, a stable bulk solid at room temperature. In one embodiment, the metal hydrides described herein are polymeric (e.g., polymeric in the bulk phase). In one embodiment, the metal hydrides described herein are in the form of a pellet.

In one embodiment, any of the metal hydrides described have a pore diameter of about 2 nm.

In one embodiment, any of the metal hydrides described herein have a porosity of between about 5 and about 80%, such as between about 5 and about 70%, between about 5 and about 60%, between about 5 and about 50%, between about 5 and about 40%, between about 5 and about 30% or between about 5 and about 20%.

In further embodiments, any of the metal hydrides described herein exhibit a gravimetric hydrogen absorption at least about 2%, at least about 3%, at least about 4%, at least about 5%, at least about 6%, at least about 7%, at least about 8%, at least about 9%, at least about 10%, at least about 11%, at least about 12%, at least about 13% or at least about 14%, e.g., in an amount up to about 14%, such as from about 2.0% to about 14.0%, from about 8.0% to about 12.0%, or about 3.5%, about 7.0%, about 10.5%, about 14%) based upon 100% total weight of the metal hydride without molecular hydrogen stored in it.

In one embodiment, the organic group R does not contain a β hydrogen substituent (e.g., R is mesityl, neopentyl, benzyl or trimethylsilylmethyl). In a preferred embodiment, R is neopentyl or mesityl.

In another embodiment, any of the metal hydrides described herein are free or substantially free of metal ions (other than titanium, vanadium, chromium, iron, cobalt, nickel and/or copper). In another embodiment, any of the metal hydrides described herein are free or substantially free of organic residue (e.g., organic ligands or solvents used during the synthesis of the metal hydride or a precursor thereof). In another embodiment, any of the metal hydrides described herein are free or substantially free of metal ions (other than titanium, vanadium, chromium, iron, cobalt, nickel and/or copper) and free or substantially free of organic residue (e.g., organic ligands or solvents used during the synthesis of the metal hydride or a precursor thereof).

In another embodiment, any of the metal hydrides described herein may contain a transition metal in more than one oxidation state (e.g., M (I)/M(II), M(I)/M(III), M(II)/M (IV), (M(II)/M(III), M(II)/M(0)) wherein M is a metal as described herein.

In one embodiment, any of the metal hydrides described herein comprise greater than about 25 wt. % of MH$_x$ (wherein x is as described in any embodiment herein), such as greater than about 30 wt. %, greater than about 40 wt. %, greater than about 50 wt. %, greater than about 60 wt. %, greater than about 70 wt. %, greater than about 75 wt. %, greater than about 80 wt. %, greater than about 85 wt. %, greater than about 90 wt. %, greater than about 95 wt. %, greater than about 99 wt. %, greater than about 99.5 wt. % of $MH_x$.

In one embodiment of any of the metal hydrides described herein, the ratio of M-H (metal-hydrogen) bonds to M-C (metal-carbon) bonds in the metal hydride is greater that about 2:1, such as greater that about 2.5:1, greater that about 5:1, greater that about 10:1, greater that about 20:1, greater that about 25:1, greater that about 50:1, greater that about 75:1, greater that about 100:1, greater that about 250:1.

In one embodiment of any of the metal hydrides described herein, the metal hydride is capable of coordinating with $H_2$. For example, in one embodiment of any of the metal hydrides described herein, the metal hydride is capable of coordinating with $H_2$ via a Kubas interaction.

The metal hydrides described herein preferably have sufficient microporosity (which may or may not be visible by nitrogen adsorption) to permit $H_2$ to move in and out of the metal hydride framework to the active binding sites. In one embodiment, the present invention relates to a metal hydride storage material comprising a metal hydride of any of the embodiments described herein, where the material has sufficient microporosity to permit: (i) $H_2$ to diffuse in and out of the material and the active binding sites of the metal hydride; (ii) the metal to coordinate with $H_2$ via, for example, a Kubas interaction; and (iii) absorption of $H_2$ in an amount of about 2.0% to about 14.0% (based upon 100% total weight of the metal hydride without hydrogen stored in it). The metal hydride storage material may be incorporated into a hydrogen storage system as described herein.

In yet another embodiment, any of the metal hydrides described herein is crystalline. In one embodiment, and without being bound by theory, the $H_2$ may move through the structure via a shuttle mechanism whereby it binds to the metal on one side and desorbs on the other to penetrate further into the structure, or moves through lammellai between crystalline planes.

In one embodiment, the metal hydrides described herein are amorphous or substantially amorphous (e.g., with little (e.g., nanoscopic order) or no long range order in the position of the atoms in the hydride structure). In one embodiment, the metal hydrides described herein contain less than about 20% crystallinity, such as less than about 10%, less than about 5%, less than about 2.5%, less than about 1%, less than about 0.5% or less than about 0.1% crystallinity, as measured, for example, by X-ray diffraction using a Cu Kα radiation (40 kV, 40 mA) source. Metal hydrides having closed packed structures are desirable due to their higher volumetric densities, so long as they permit diffusion of $H_2$ to the metal binding sites within them. Where the closed packed structure of a metal hydride does not permit diffusion of $H_2$ to the metal binding sites, the metal hydride preferably does not have a closed packed structure.

In one embodiment, the metal hydrides described herein are greater than 80% amorphous, such as greater than about 85%, greater than about 90%, greater than about 95%, greater than about 99% or greater than about 99.5% amorphous, as measured, for example, by X-ray diffraction using a Cu Kα radiation (40 kV, 40 mA) source.

In another embodiment, any of the metal hydrides described herein may contain a minor amount (e.g., up to 0.5 moles total) of an impurity selected from phosphines (e.g., trimethylphosphine), ethers, water, alcohols, amines, olefins, sulfides, nitrides, and combinations thereof. The phosphine (e.g., trimethylphosphine), ether, water, alcohol, amine, olefin (e.g., 1-hexene) sulfide or nitride residues may remain from their use in the synthesis of the metal hydride or may be formed as byproducts during the synthesis. In one embodiment, any of the metal hydrides of the present invention may contain less than about 10.0 wt %, less than about 9.0 wt %, less than about 9.0 wt %, less than about 7.5 wt %, less than about 5.0 wt %, less than about 4.0 wt %, less than about 3.0 wt %, less than about 2.0 wt %, less than about 1.0 wt %, less than about 0.75 wt %, less than about 0.5 wt %, less than about 0.4 wt %, less than about 0.3 wt %, less than about 0.25 wt %, less than about 0.2 wt %, less than about 0.1 wt %, less than about 0.05 wt %, less than about 0.01 wt %, less than about 0.005 wt % or less than about 0.001 wt % of a phosphine (e.g., trimethylphosphine), ethers (e.g., $Et_2O$, THF, dioxane), water, alcohol, amine, olefin (e.g., 1-hexene), sulfide or nitride residue, or a combination thereof. In a preferred embodiment, the metal hydride is free or substantially free of a phosphine (e.g., trimethylphosphine), ethers, water, alcohol, amine, olefin, sulfide or nitride residue, or a combination thereof. In addition, in embodiments of the invention where impurities are found, the metal hydrides described herein may also contain minor amounts (e.g., up to 0.5 moles total) of metal hydroxides (M-OH) and metal ethers (M-O-M) from the hydrolysis of metal alkyl species with residual water contained within the reaction mixture.

In certain embodiments, any of the metal hydrides of the present invention contain less than about 10.0 wt % of lithium or magnesium, or a combination thereof. These lithium and magnesium residues may remain from their use in the synthesis of the metal hydride. For example, any of the metal hydrides of the present invention may contain less than about 9.0 wt %, less than about 8.0 wt %, less than about 7.5 wt %, less than about 5.0 wt %, less than about 4.0 wt %, less than about 3.0 wt %, less than about 2.0 wt %, less than about 1.0 wt %, less than about 0.75 wt %, less than about 0.5 wt %, less than about 0.25 wt %, less than about 0.1 wt % or less than about 0.05 wt %, less than about 0.01 wt %, less than about 0.005 wt %, or less than about 0.001 wt % of lithium or magnesium or a combination thereof. In another embodiment, any of the metal hydrides of the present invention contain less than about 0.5 wt % of lithium or magnesium, or a combination thereof. For example, any of the metal hydrides of the present invention may contain less than about 0.4 wt %, less than about 0.3 wt %, less than about 0.25 wt %, less than about 0.2 wt %, less than about 0.1 wt %, less than about 0.05 wt %, less than about 0.01 wt %, less than about 0.005 wt % or less than about 0.001 wt % of lithium or magnesium or a combination thereof. In a preferred embodiment, the metal hydride is free or substantially free of lithium or magnesium, or a combination thereof.

The metal hydrides of the present invention may contain halogen. For instance, the metal hydride may contain less than about 20.0 wt % of a halogen, such as less than about 10.0 wt % of a halogen (such as $Br^-$, $Cl^-$, or $I^-$). These halogen residues may remain from their use in the synthesis of the metal hydride (for instance, from the use of a Grignard reagent). For example, any of the metal hydrides of the present invention may contain less than about 9.0 wt %, less than about 8.0 wt %, less than about 7.5 wt %, less than about 5.0 wt %, less than about 4.0 wt %, less than about 3.0 wt %, less than about 2.0 wt %, less than about 1.0 wt %, less than about 0.75 wt %, less than about 0.5 wt %, less than about 0.25 wt %, less than about 0.1 wt % less than about 0.05 wt %, less than about 0.01 wt %, less than about 0.005 wt %, or less than about 0.001 wt % of halogen. In a preferred embodiment, the metal hydride is free or substantially free of halogen.

In one embodiment, any of the metal hydrides described herein (e.g., Formulas (I) and (II)) are capable of absorbing molecular hydrogen (H$_2$) in an amount of at least 2.0% (e.g., from about 2.0% to about 8.0%, from about 8.0% to about 12.0%, or higher) (based upon 100% total weight of the metal hydride without hydrogen stored in it). In another embodiment, the metal hydride is capable of absorbing molecular hydrogen (H$_2$) in an amount of from about 2.0, 2.5, 3.0, or 3.5% to about 4.0, 4.5, 5.0, 5.5, 6.0, 6.5, or 7.0%. In another embodiment, the metal hydride is capable of absorbing molecular hydrogen (H$_2$) in an amount of from about 8.0, 8.5 or 9.0% to about 11.0, 11.5 or 12%.

The metal hydrides of the present invention are capable of absorbing molecular hydrogen (H$_2$) in an amount of at least about 2%, at least about 3%, at least about 4%, at least about 5%, at least about 6%, at least about 7%, at least about 8%, at least about 9%, at least about 10%, at least about 11%, at least about 12%, at least about 13% or at least about 14%, e.g., in an amount up to about 14%, such as from about 2.0% to about 14.0%, from about 8.0% to about 12.0%, or about 3.5%, about 7.0%, about 10.5%, about 14%) based upon 100% total weight of the metal hydride without molecular hydrogen stored in it.

In one embodiment of any of the metal hydrides described herein, R, if present, is selected from alkyl, silylated alkyl, alkenyl, arylalkyl, heteroayl and aryl.

In one embodiment of any of the metal hydrides described herein R, if present, is selected from (trimethylsilyl)methyl, bis(trimethylsilyl)methyl, phenyl, benzyl, mesityl (or a group of formula (V) below where R$^1$ is any organic group), allyl, 1,3-dimethyl allyl, 1,3-diethyl allyl (or another 1,3-disubstituted allyl where the substituents are organic groups), neopentyl, 2,2,2-dimethylphenylpropyl, benzyl, benzyl substituted on its aromatic ring with one or more groups (for example, methoxide or norborane) at its meta and para positions, aryl, aryl substituted on its aromatic ring with one or more groups (for example, methoxide or norborane) at its meta and para positions, and combinations thereof. In one embodiment, R is a silylated alkyl group, such as bis(trimethylsilyl)methyl.

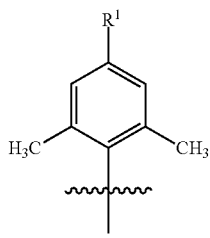

Formula (V)

In another embodiment R, if present, is selected from (trimethylsilyl)methyl, bis(trimethylsilyl)methyl, mesityl, allyl, 1,3-dimethyl allyl, benzyl, phenyl and combinations thereof. In one embodiment, R is a silylated alkyl group, such as bis(trimethylsilyl)methyl. In one embodiment, R is phenyl.

In one embodiment, the present invention relates to a metal hydride storage material comprising one or more metal hydrides prepared by any of the processes described herein.

In another embodiment, the present invention relates to a metal hydride storage material comprising one or more metal hydrides according to any of the embodiments described herein.

The metal hydride storage material may be incorporated into the hydrogen storage system as described herein.

Hydrogen Storage

In another embodiment, the present invention relates to a method of storing hydrogen comprising providing a metal hydride according to any of the embodiments described herein (e.g., a metal hydride prepared according to any of the processes described herein and/or one or more metal hydrides of formula (I) or (II)), adding hydrogen to the metal hydride, and allowing the hydrogen to coordinate to the metal hydride. The storing of hydrogen may be carried out in a storage system.

One embodiment of a storage system suitable for hydrogen storage is a pressure vessel. For example, the pressure vessel may hold the metal hydride of the present invention at a temperature of up to 200° C., e.g., from about −100 to about 150° C., from about −50 to about 0° C., from about −25 to about 0° C., from about 0 to about 150° C., from about 0 to about 50° C., from about 10 to about 30° C. or from about 20 to about 25° C. In one embodiment, the storage system is substantially free of oxygen.

Hydrogen may be added to the storage system (e.g., a pressure vessel) and stored using the metal hydrides of the present invention. In one embodiment, no heating is required when adding hydrogen to the pressure vessel for storage.

The amount of hydrogen that can be stored by the metal hydrides of the present invention is proportional to the pressure in the storage system. For example, at higher pressures, more hydrogen can be stored by the metal hydrides of the present invention. The pressure in the storage system may be increased by adding hydrogen to the storage system. Without wishing to be bound by any particular theory, the inventor theorizes that as the pressure is increased, the number of Kubas interactions per metal centre may increase. For example, when the metal hydride is a metal dihydride such as MH$_2$, one hydrogen molecule coordinated to the metal (e.g., by a Kubas interaction) affords MH$_4$. Two hydrogen molecules coordinated to the metal (e.g., by Kubas interactions) affords MH$_6$. Three hydrogen molecules coordinated to the metal (e.g., by Kubas interactions) affords MH$_8$. Four hydrogen molecules coordinated to the metal (e.g., by Kubas interactions) affords MH$_{10}$. Five hydrogen molecules coordinated to the metal (e.g., by Kubas interactions) affords MH$_{12}$. As noted above, however, this process will appear continuous in the bulk state, resulting in the formation of a bulk material containing metal hydrides having a mixture of coordinated hydrogen molecules, and, therefore, an overall non-integer stoichiometry of manganese to hydrogen. Furthermore it may be possible (e.g., via a free radical and/or bimolecular process) to form molecular species of the formula MH$_3$, MH$_5$, MH$_7$, MH$_9$ and MH$_{11}$.

In further embodiments, any of the metal hydrides described herein optionally contain one or more additional metals (e.g., a metal other than titanium, vanadium, chromium, manganese, iron, cobalt, nickel and copper). For example, the metal hydride may contain one or more additional metals selected from sodium, potassium, aluminum, beryllium, boron, calcium, lithium, magnesium and combinations thereof. In an alternate embodiment, the metal hydride may contain one or more additional metals (e.g., a metal other than titanium, vanadium, chromium, manganese, iron, cobalt, nickel and copper) wherein the one or more additional metals is a period 4, 5, 6, 7, 8, 9, 10, 11 and/or 12 transition metal, or a lanthanide, that forms a hydride upon treatment with hydrogen. For example, the metal hydride may contain one or more additional metals selected from zirconium, niobium, molybdenum, technetium, ruthenium, rhodium, palladium, silver, and combinations thereof. In one embodiment, any of the metal hydrides described herein may optionally contain one or more additional period 4, period 5 or period 6 transition metals. In another embodiment, the metal hydride may contain one or more additional metals selected from iron, zirconium, niobium, molybdenum, technetium, ruthenium, rhodium, palladium, silver, cadmium, hafnium, tantalum, tungsten, rhenium, osmium, iridium, platinum, gold, mercury, and combinations thereof. The one or more additional metals may be present in an amount of about 50 wt. % or less, about 40 wt. % or less, about 30 wt. % or less, about 25 wt. % or less, about 20 wt % or less, about 10 wt % or less, about 5 wt % or less, about 1 wt % or less, about 0.75 wt % or less, about 0.5 wt % or less, about 0.25 wt % or less, about 0.1 wt % or less, about 0.05 wt % or less or about 0.01 wt % or less. In one embodiment, the metal hydrides described herein contain no additional metal (e.g., no metal other than manganese).

The hydrogen pressure in the system may be increased using a compressor, such as a gas compressor, which pumps hydrogen into the system. Preferably, the hydrogen pressure in the system is increased to about 30 atm or more. For example, the hydrogen pressure in the system may be increased to from about 30 atm to about 500 atm, from about 50 atm to about 200 atm, or from about 75 atm to about 100 atm.

The system preferably has a temperature of (or operates at) up to 200° C., such as about −200° C. to 150° C. (e.g., about −100° C. to 150° C.), about −200° C. to 100° C., about 0° C. to 50° C., about 10° C. to 30° C., or about 20° C. to 25° C. In one embodiment, the system has a temperature (or operates at) about 25° C. to about 50° C. The system is preferably free of oxygen to prevent the oxidation of metal in the system. In one embodiment, the method of storing and releasing hydrogen in a system of the present invention may be carried out without adding heat to and/or cooling the system. In another embodiment, the method of storing and releasing hydrogen in a system of the present invention may be carried out by adding heat to and/or cooling the system.

In a further embodiment, the hydrogen is released from the storage system. For example, this may be accomplished by reducing the pressure of hydrogen in the system. In one embodiment, no heating is required in order to release the hydrogen from the metal hydride. For example, a valve in the storage system may be opened to allow hydrogen gas to escape from the system, thus decreasing the pressure in the storage system. In one embodiment, about 100% of the stored hydrogen is released. In additional embodiments, greater than about 50%, greater than about 55%, greater than about 60%, greater than about 70%, greater than about 75%, greater than about 80%, greater than about 90%, greater than about 95%, greater than about 97.5%, greater than about 99% or greater than about 99.5% of the hydrogen is released. The step of releasing the hydrogen pressure in the system may be carried out by allowing hydrogen gas to escape from the system, thus decreasing the hydrogen pressure. For instance, the step of releasing the hydrogen pressure may decrease the hydrogen pressure in the system to 100 atm or less (such as to 50 atm or less, 30 atm or less, or 20 atm or less). In another embodiment, the hydrogen is released from the storage system by increasing the temperature of the system.

Hydrogen may be added or released from the system at any point throughout the entire pressure gradient of the system without any adverse effects to the storage capacity of the system. In certain embodiments, hydrogen may be added or released from the system any number of times without any adverse effect to the storage capacity of the system. For example, the system can be filled with hydrogen and emptied of hydrogen at least 100, such as at least 200, at least 500, at least 1000 or at least 1500 times without a significant decrease in the storage capacity of the system.

In one embodiment, the storage system (e.g. pressure vessel) is a fuel tank in a vehicle, such as a truck or automobile.

Figure 2:
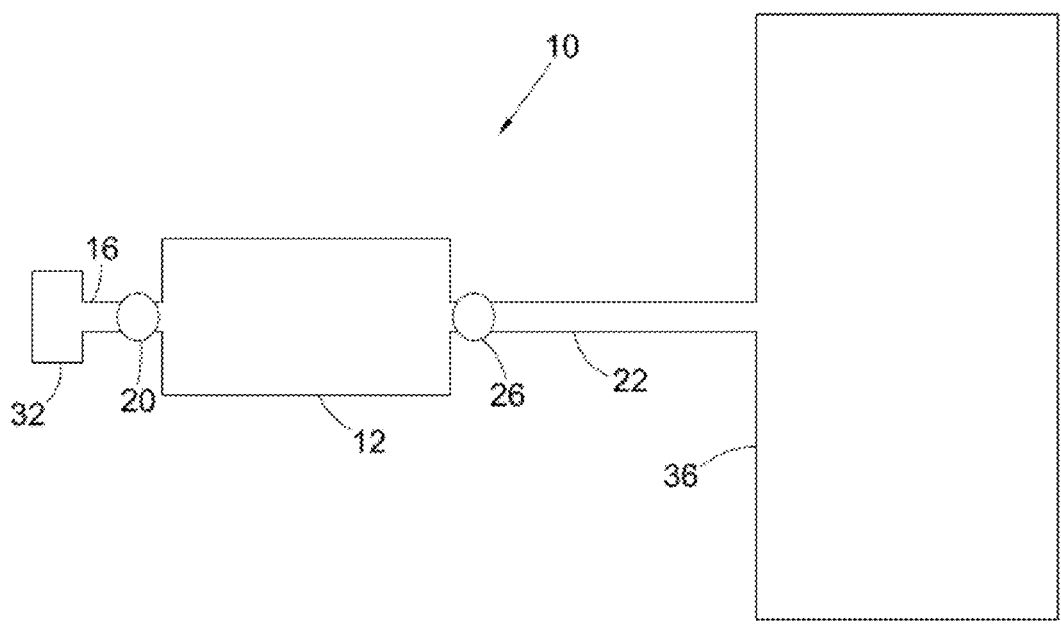
FIG. 2 depicts an embodiment of the storage system attached to a hydrogen fuel cell.

FIG. 1 depicts an embodiment of a storage system useful in the present invention. FIG. 2 depicts an embodiment of the storage system attached to a hydrogen fuel cell. The system 10 comprises a tank body 12 which is made of a material that is impermeable to hydrogen gas, thus preventing undesired leaking of the hydrogen gas out of the tank body 12. For example, the tank body 12 is made of metal, such as, e.g., steel or aluminum. Alternatively, the tank body 12 is made of a composite material, such as a composite of fibreglass and aramid. In another embodiment, the tank body 12 is made of a carbon fibre with a liner. The liner may be a polymer liner, such as a thermoplastic liner or a metal liner, such as a steel liner or an aluminum liner.

The metal hydride 14 of the present invention is present inside the tank body 12. In FIG. 1, the metal hydride 14 is in a gel form. The metal hydride 14 may partially fill or totally fill the tank body 12. In certain embodiments, the metal hydride may be present as a coating on a support or in pellet form, depending upon the requirements for pressure drops in the tank body. In additional embodiments, the metal hydride may be present in admixture with other compounds (such as a binder) which enhance the structural integrity and other properties of the coating or the pellet.

A first passage 16 leads to a first opening 18 in the wall of the tank body 12. A first valve 20 controls the flow of hydrogen gas through the first opening 18.

A second passage 22 extends from a second opening 24 in the wall of the tank body 12. A second valve 26 controls the flow of hydrogen gas through the second opening 24.

The first valve 20 and the second valve 26 can be any type of valve that controls the flow of hydrogen gas through the first opening 18 and the second opening 24, respectively. For example, the first valve 20 and the second valve 26 can be ball valves or gate valves.

In one embodiment, hydrogen is added to the system 10 as follows. A gas compressor 32 pumps hydrogen gas into the first passage 16. The first valve 20 is opened to allow the hydrogen gas to flow through the first opening 18 and into the tank body 12.

A passage tube 28 is in gaseous communication with the first opening 18 and extends into the interior of the tank body 12. The passage tube 28 facilitates the distribution of the hydrogen gas to the metal hydride 14. In one embodiment, the passage tube 28 is made of a material that is permeable to the hydrogen gas. This allows the hydrogen gas to pass through the wall of the passage tube 28 and into contact with the metal hydride 14. The passage tube is also preferably made of a material that is impermeable to the metal hydride 14, thus preventing the metal hydride 14 from entering into the interior of the passage tube 28. The passage tube 28 preferably opens into the interior of the tank body 12. The opening of the passage tube 28 is preferably covered with a filter 30 which prevents the metal hydride 14 from entering into the interior of the passage tube 28.

When the compressor 32 pumps hydrogen gas into the tank body 12, there is an increase of the hydrogen pressure inside the tank body 12. When the hydrogen pressure inside the tank body is increased, the metal hydride 14 is able to coordinate with a greater amount of hydrogen. Preferably, the increase in pressure causes an increase in the number of Kubas interactions per metal centre in the metal hydride 14. After the desired amount of hydrogen has been added to the system, the valve 20 is closed.

When desired, hydrogen may be released from the system 10 as follows. The second valve 26 is opened, which allows hydrogen gas to flow out of the tank body 12 through the second opening 24. When hydrogen gas flows out of the tank body through the second opening 24, there is a decrease in pressure inside the tank body 12. When the pressure is decreased inside the tank body 12, the metal hydride 14 releases hydrogen. For example, the decrease in pressure may cause a decrease in the number of Kubas interactions per metal centre of the metal hydride 14.

Hydrogen that is released by the metal hydride 14 can flow out of the tank body 12 through the second opening 24. As shown in FIG. 2, the hydrogen can flow through the second passage 22 to a fuel cell 36. The fuel cell 36 preferably uses hydrogen as a fuel and oxygen as an oxidant to produce electricity. Typically, a filter is present at the second opening 24 in order to prevent loss of particulates downstream.

In an alternative embodiment, the storage system of the present invention comprises a storage tank with a single opening. In this embodiment, hydrogen flows both into and out of the storage tank through the single opening. A valve is used to control the flow of hydrogen through the opening. Since the enthalpies of $H_2$ binding are moderate to thermodynamically neutral and binding may be controlled by pressure, the tank may not need an exotic heat management system for most applications, unlike many prior hydrogen storage systems.

In one embodiment, the system is portable. As such, the system can be transported to a filling station to be filled with hydrogen. After being filled with hydrogen, the system can then be transported to a site where the hydrogen energy is to be used. Applications for this system include, but are not limited to, vehicles, airplanes, homes, buildings, and barbeques.

EXAMPLES

The present invention will now be further described by way of the following non-limiting examples. In applying the disclosure of these examples, it should be kept clearly in mind that the examples are merely illustrative of the present invention and should not be construed as limiting the scope of the invention in any way as many variations and equivalents that are encompassed by the present invention will become apparent to those skilled in the art upon reading the present disclosure.

All chemicals were purchased from Sigma-Aldrich and used without further purification. Standard Schlenk techniques were used and manipulations were performed in an argon glove box and on a nitrogen Schlenk line Nitrogen adsorption and desorption data were collected at 77K on a Micromeritics ASAP 2020™.

Infrared spectroscopy was conducted on a Perkin Elmer Spectrum RX1 using KBr discs. Prior to analysis the IR grade KBr was oven dried overnight at 120° C. to remove any residual water. A blank sample of KBr was ground in an oven-dried pestle and mortar in the glovebox and then compressed in air to form a disc. A background was taken of the blank KBr disc. Approximately 5 mg of sample was ground with 200 mg IR grade, oven dried KBr and compressed to form a disc. The spectrum of KBr was subtracted from the IR of the sample.

Thermogravimetric analysis (TGA) and differential thermal analysis (DTA) was performed in a STA 449C analyser from Netzsch under a flow of dried air at 10.00° C./min up to 650° C. Argon was also used to protect the balance section.

X-Ray powder diffraction (XRPD) patterns were collected by putting a small amount of powder in small capillaries (1 mm in diameter) and the XRD spectrum was taken using a Bruker Discover diffractometer with a Vantec 500 2D detector using Co Kα radiation. The X-ray beam was limited using a 0.2 mm collimator.

Hydrogen adsorption isotherms were obtained using a computer controlled gas sorption Sieverts apparatus manufactured by Hy-Energy. High purity hydrogen (Grade 6, 99.9999% purity) purchased from Air Liquide was used. Stainless steel spacers were added to the sample holder along with the material to reduce excess void space. The void space of the sample was calculated by performing a helium volume calibration at 298K using 5 each adsorption and desorption points (total of 10), with outlying values discarded and rerun. Excess hydrogen storage measurements on a 200 mg standard AX-21 sample (0.65 wt. % at 70 bar and 298 K) were performed and ensure correct functioning of the instrument and to ensure the accuracy of the isotherms. The reported gravimetric hydrogen storage capacity of Carbon-AX21 is 0.3 wt % at 35 bar (Bernard et al., *Assessment of Hydrogen Storage on Different Carbons*, IEA Report, 2001). This corresponds to 0.6 wt % at 70 bar which gives an error of ±0.07 wt % ((0.65-0.6)×100/70) at 100 bar $H_2$ with a 200 mg sample size. This sample size was chosen such that the absolute amount adsorbed was equivalent to that in the metal hydride hydrogen storage experiments described herein (ca. 1 mmol $H_2$) to eliminate systematic error, since the instrument measures total mols hydrogen adsorbed and then converts it to wt %.

Raman spectra were obtained using a Renishaw inVia Raman Microscope with a 488 nm excitation laser (20 mW power on the sample). The sample was placed in an aluminum pan and loaded into the sample cell inside an argon glovebox (MBraun Labstar) with the levels of water and oxygen kept below 0.1 ppm. A microscope objective was used to focus the laser beam onto the sample with a spot-diameter of about 50 μm. The bespoke sample cell stage, with a 3 mm thick sapphire window, was used to measure pressure-dependent Raman spectra up to 50 bar. Hydrogen (99.9995% purity) or deuterium (100%) pressure was maintained using a computer controlled mass flow controller and back pressure regulator. Spectra were obtained by taking 750 scans and adding the intensities.

Calorimetry data was collected using a reaction, scanning and isotherm C80 calorimeter manufactured by Setaram. Two high pressure cells were used, one for the sample and one as a reference and the cells were linked to the PCT-Pro via a stainless steel gas line with connections manufactured by Swagelok. The instrument set-up was calibrated by measuring the enthalpy of hydrogen adsorption of 540 mg of palladium. A PCT hydrogen adsorption measurement of Palladium up to 6 bar was taken simultaneously to an isothermal calorimetry measurement at 170° C. The total heat of adsorption of palladium was determined to be 31.6 kJ mol$^{-1}$ $H_2$, which is in line with literature values. For a measurement, 200 mg of a sample was placed in the sample cell with stainless steel spacers to reduce the void space. Identical spacers were also placed in the reference cell. Prior to the measurement the void space of the cells and gas line were determined using a helium volume calibration, one at room temperature and one with the cells in the C80 furnace at 40° C. A hydrogen adsorption measurement was set up using the PCT-Pro apparatus with a dose time for each addition of hydrogen gas to the sample set to 60 minutes. This is to allow for thermal equilibration before the hydrogen adsorption measurement moves onto the next dose. The C80 calorimeter was set to take an isothermal measurement of the heat flow of the sample during the PCT measurement with the temperature of the furnace kept constant at 40° C. A calorimetry measurement of a blank cell was also conducted at 40° C. simultaneously as a hydrogen adsorption measurement of the blank cell. This was to determine the heat flow during warming of the gas when it is introduced into the cells at different pressures. The total heat of the blank run was subtracted from the total heat of the sample. To determine the hydrogen adsorption enthalpy this value was then divided by the total number of moles of hydrogen adsorbed by the material.

High Resolution Scanning Transmission Electron Microscopy (HRSTEM) was performed in a HD-2700 dedicated Scanning Transmission Electron Microscope (STEM) from Hitachi, with a cold field emitter equipped with a CEOS Cs corrector and operated at 200 kV. The powder samples were dry deposited in an argon filled glove box onto a Cu grid covered with a carbon film (Quantifoil) having periodical holes with diameter of 1.2 microns. Observation was made in three different modes: Bright Field (BF), High Angle Annular Dark Field (HAADF) and Secondary Electron (SE).

Example 1

Chromium (III) Hydride Samples

Synthesis
Preparation of Tetrakis(trimethylsilylmethyl) Chromium

To a stirred suspension of $CrCl_3(THF)_3$ (7.617 g, 20.33 mmol) in 40-60° C. petroleum ether, was added a solution of (trimethylsilyl)methyllithium (76.4 mmol, 76.64 mL of a 1.0 M solution in pentane). The colour of the slurry immediately changed to dark purple. The mixture was stirred at room temperature for 3 hours, and then filtered, and the residue was washed with three portions of petroleum ether (10 mL each). The dark purple filtrate was concentrated and dried at room temperature in vacuo for 24 hours to afford a dark purple crystalline solid (4.8 g, 96% yield). See Schulzk et al., *Organometallics*, 21, 3810, 2002.

Formation of Chromium (III) Hydride

A dark purple solution of tetrakis(trimethylsilylmethyl) chromium (IV) (1.2040 g, 5.22 mmol) in 50 mL of petroleum ether was placed in a 600 mL stirred hydrogenation vessel. The vessel was slowly heated to 100° C. and the reaction stirred for two days. The reaction mixture was filtered to give a black precipitate and a brown filtrate. The precipitate was dried in vacuo at 100° C. for four hours to afford a black air moisture sensitive solid (Cr-100). This material was placed in the stainless steel sample holder of the Hy-Energy PCT-Pro Sieverts apparatus and the sample holder was heated to 150° C. at a pressure of 85 bar $H_2$ for four hours. The material was then cooled to 100° C. and evacuated for two hours at this temperature to give sample Cr-150C—$H_2$. The material was then placed in the stainless steel 600 mL hydrogenation vessel and the vessel was pressurized to 70 bar $H_2$ at 25° C. for 2 days. After removal from the pressure vessel the material was dried in vacuo at 100° C. for four hours to give a black air and moisture sensitive solid (Cr-25C—$H_2$).

Sample Characterization

Figure 3:
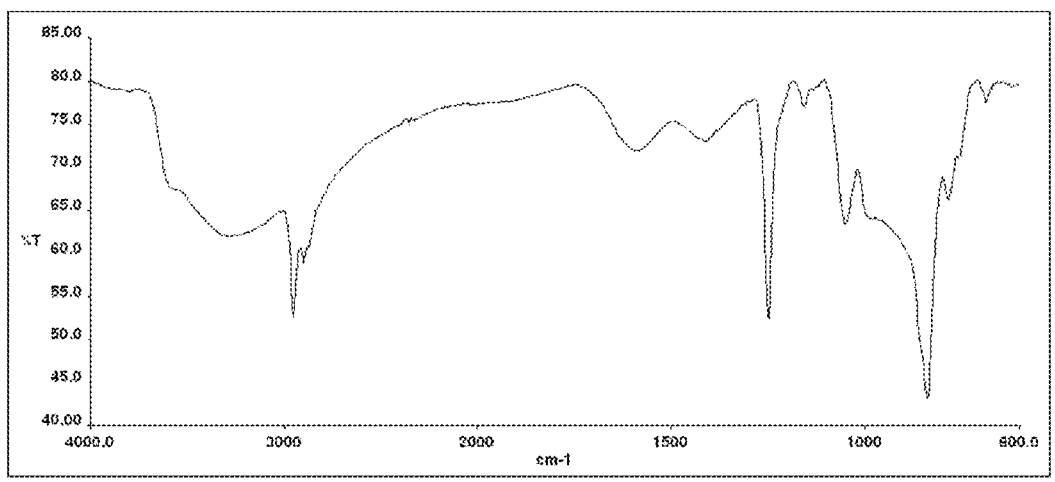
FIG. 3 depicts an IR spectrum of chromium hydride sample Cr-100.
Figure 4:
FIG. 4 depicts an IR spectrum of chromium hydride sample Cr-150C—$H_2$.
Figure 5:
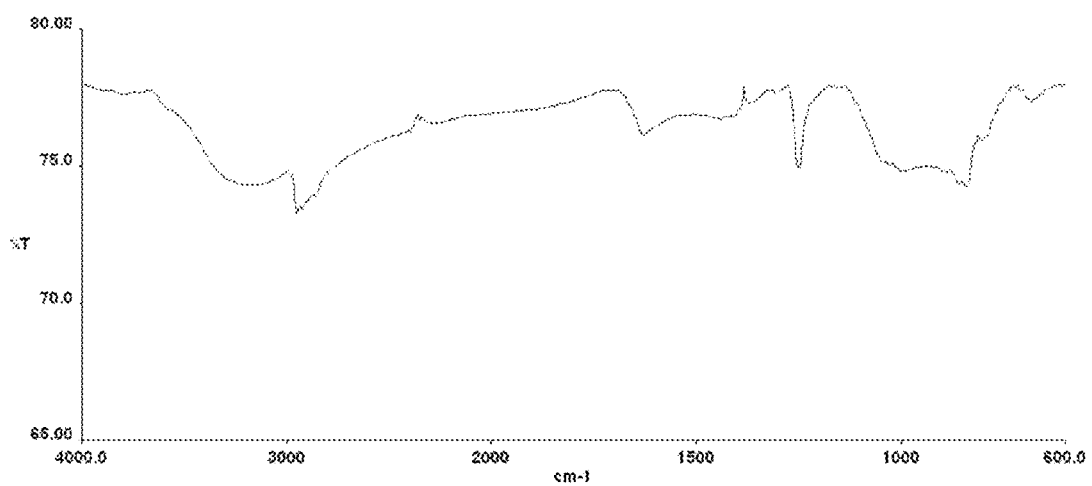
FIG. 5 depicts an IR spectrum of chromium hydride sample Cr-25C—$H_2$.

The Infra-Red (IR) spectrum for samples Cr-100, Cr-150-$H_2$ and Cr-25C—$H_2$ are shown in FIGS. 3, 4 and 5, respectively. For sample Cr-100, C—H stretches are observed at 2950 and 2897 $cm^{-1}$. The stretch at 1250 $cm^{-1}$ may be attributed to a C—Si stretch from (trimethylsilyl)methyl ligands present in the material. The intensity of both the C—H and C—Si stretches at 2950 $cm^{-1}$ and 1250 $cm^{-1}$ decreases after each hydrogenation treatment, as the hydrocarbon ligands are replaced by hydrides during hydrogenolysis.

Figure 6:
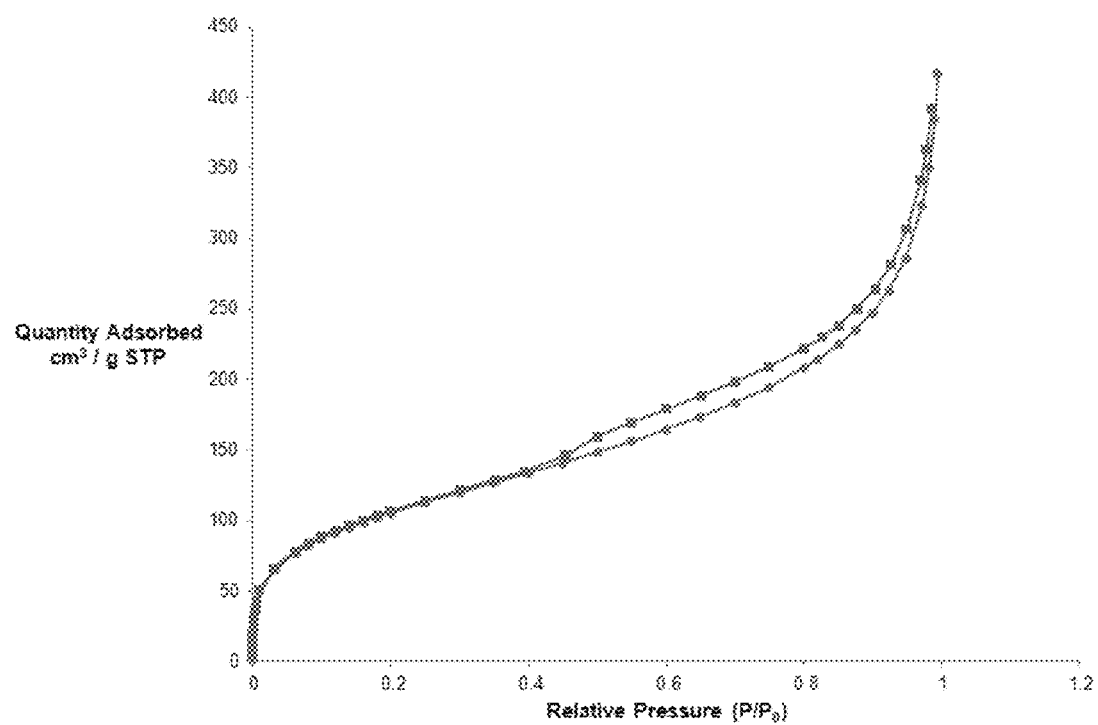
FIG. 6 depicts a nitrogen adsorption (lower trace)-desorption (upper trace) isotherm for chromium hydride sample Cr-100.
Figure 7:
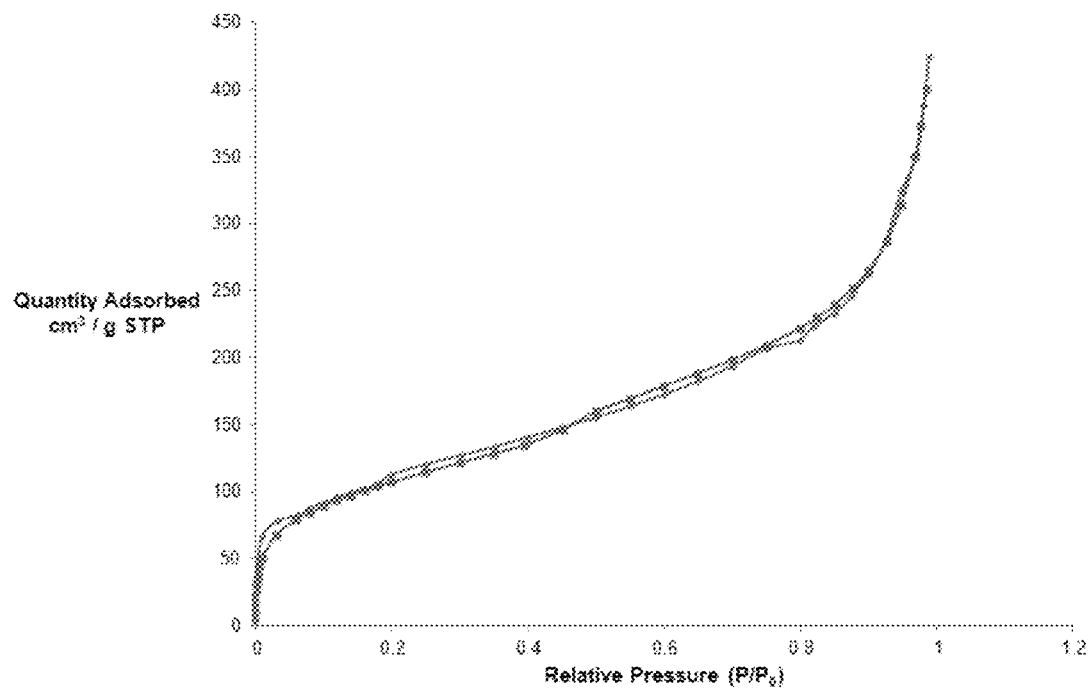
FIG. 7 depicts a nitrogen adsorption (lower trace)-desorption (upper trace) isotherm for chromium hydride sample Cr-25C—$H_2$.

Nitrogen adsorption-desorption isotherms for Samples Cr-100 and Cr-25C—$H_2$ recorded at 77K are shown in FIGS. 6 and 7, respectively. Both samples Cr-100 and Cr-25C—$H_2$ possess a type 2 isotherm. Sample Cr-100 has a BET surface area of 377 $m^2/g$. After room temperature hydrogenation, the BET surface area for sample Cr-25C—$H_2$ increased to 391 $m^2/g$. This may be due to the removal of hydrocarbon ligands creating new porous pathways in the structure facilitating gas diffusion through the structure. In both samples there is hysteresis between the adsorption and desorption isotherms, which means that the materials are porous. There is a fairly steep increase between 0 and 0.1 P/Po, which suggests that there may be some level of microporosity comprising approximately 20% of the total volume adsorbed. The moderate increase in slope between 0.1 and 0.8 P/Po arises from mesoporosity and the increasing slope between 0.8 and 1.0 P/Po arises from textural porosity.

Figure 8:
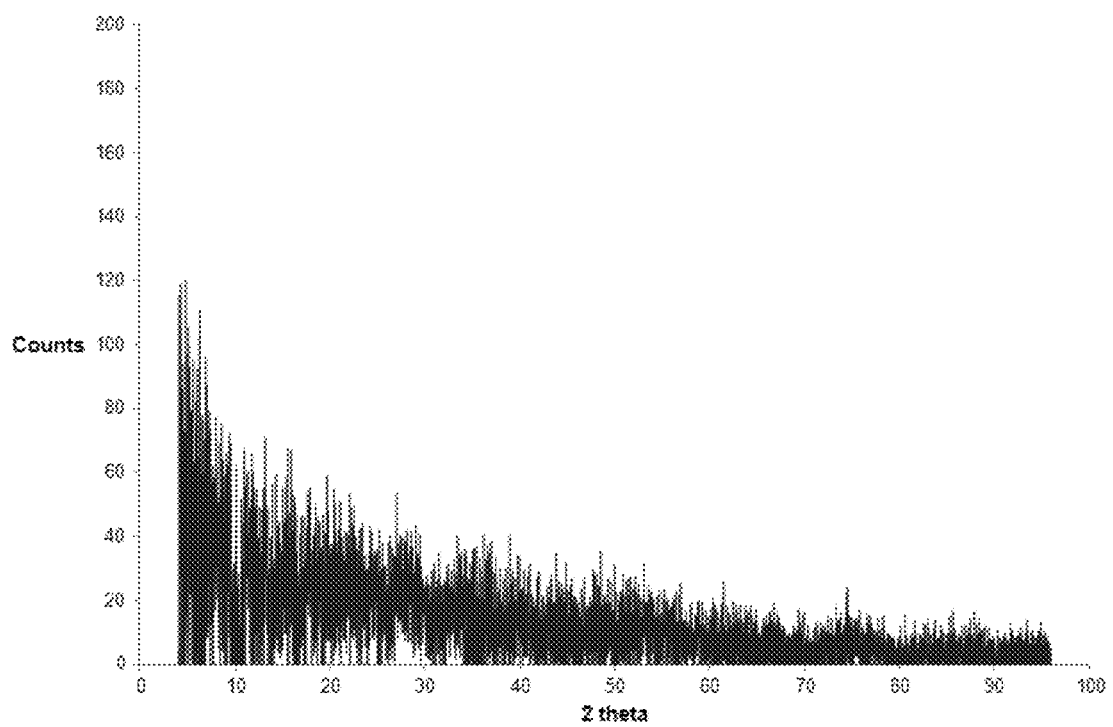
FIG. 8 depicts an X-ray powder diffraction (XRPD) pattern of chromium hydride sample Cr-100.
Figure 9:
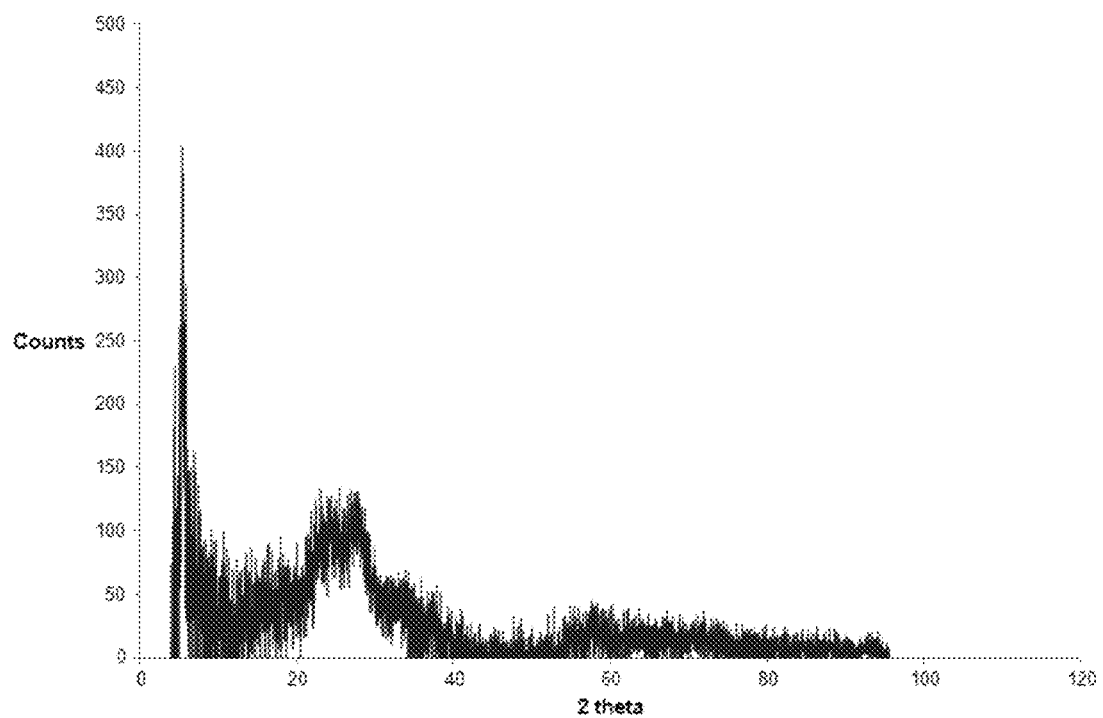
FIG. 9 depicts an X-ray powder diffraction (XRPD) pattern of chromium hydride sample Cr-150C—$H_2$.
Figure 10:
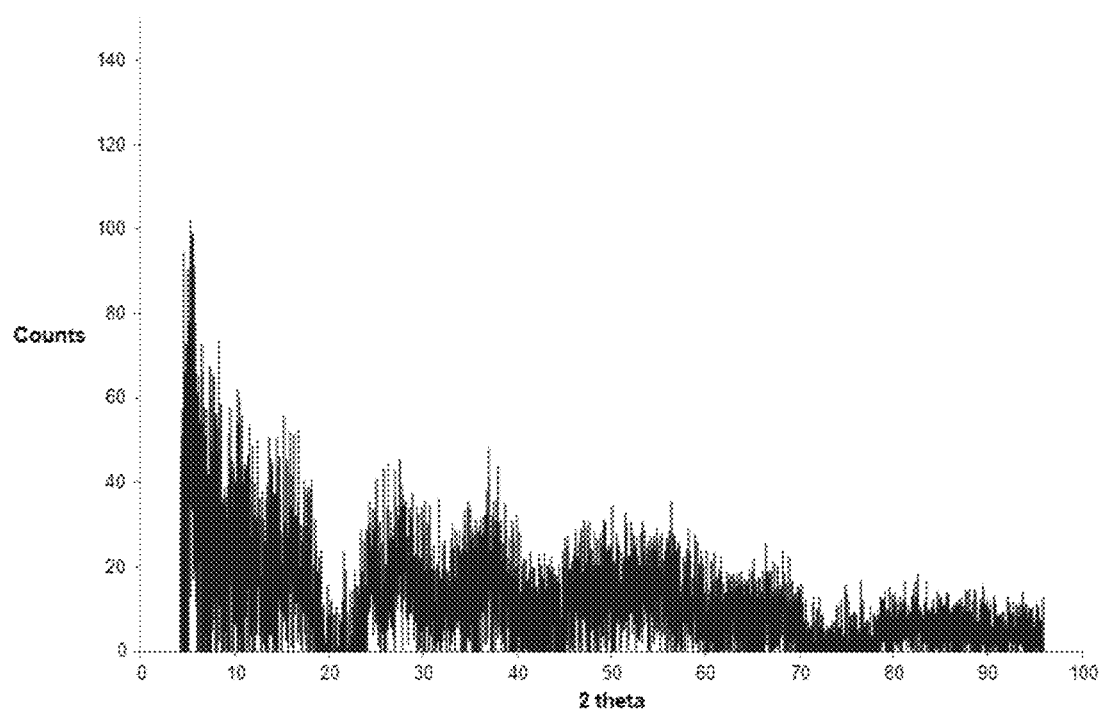
FIG. 10 depicts an X-ray powder diffraction (XRPD) pattern of chromium hydride sample Cr-25C—$H_2$.

The X-ray powder diffraction (XRPD) patterns for samples Cr-100, Cr-150C—$H_2$ and Cr-25C—$H_2$ are shown in FIGS. 8, 9 and 10, respectively. All three samples are largely amorphous. In FIGS. 9 and 10, a minor reflection can be seen in the 20-30° region, which corresponds to the glass capillaries.

Figure 10A:
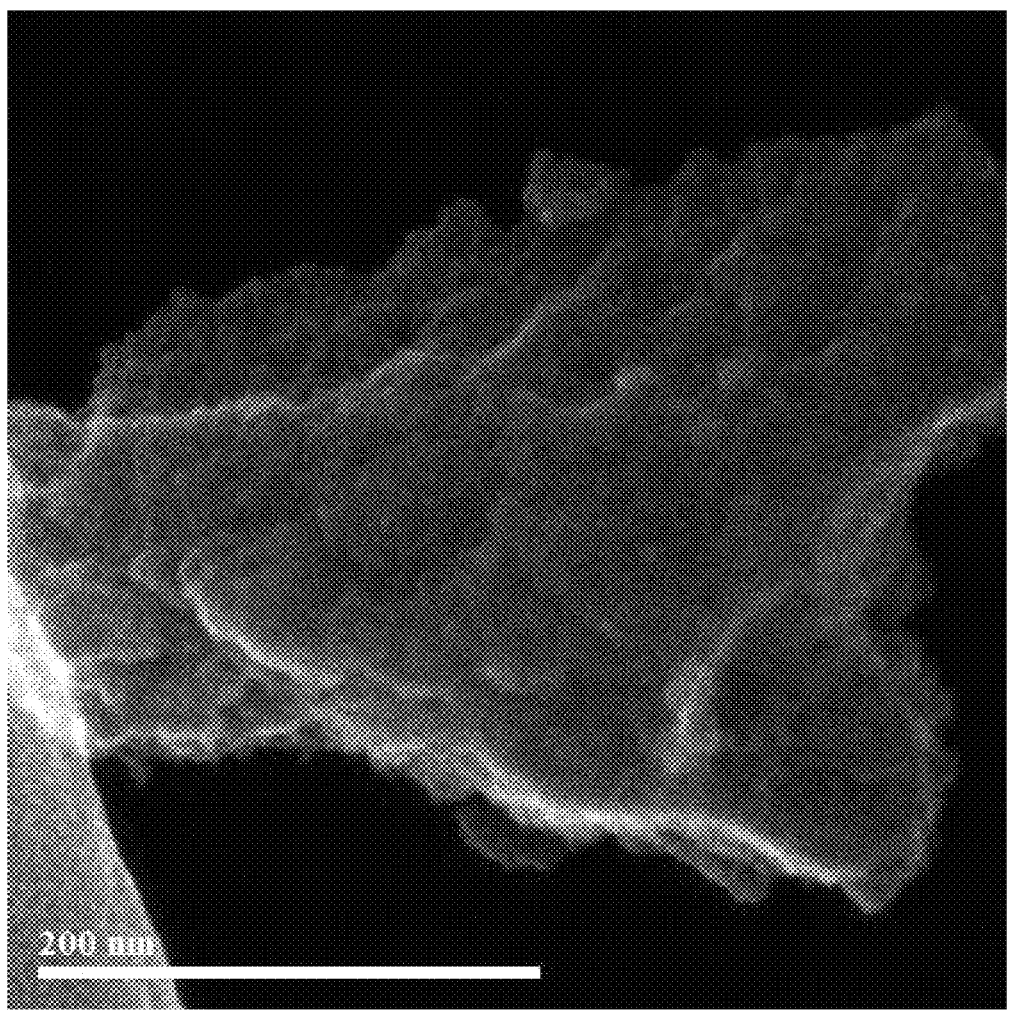
FIGS. 10A and 10B depict high resolution scanning transmission electron microscopy (HTSTEM) images for chromium hydride sample Cr-25C—$H_2$.
Figure 10B:
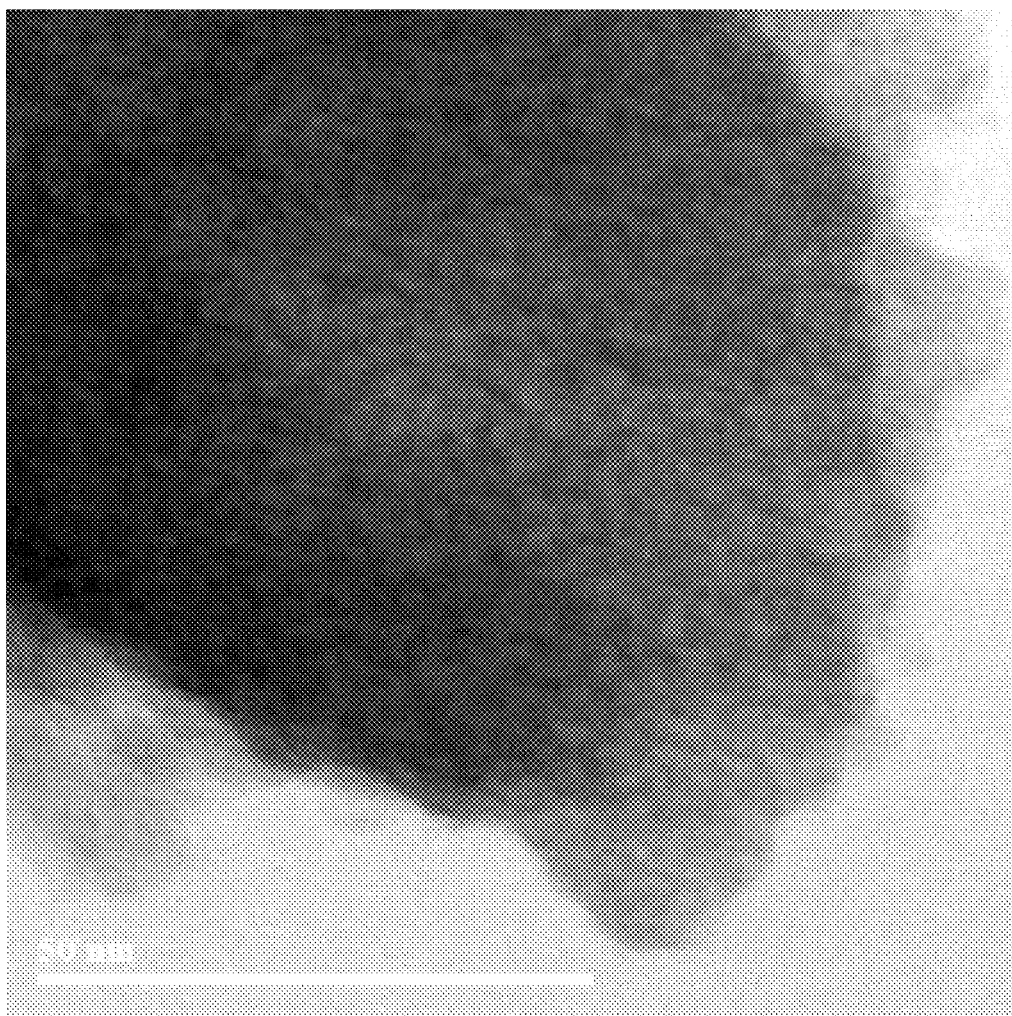

FIGS. 10A and 10B depict high resolution scanning transmission electron microscopy (HTSTEM) images for chromium hydride sample Cr-25C—$H_2$. FIG. 10A shows the powder morphology and FIG. 10B shows a pore structure of approximately 2 nm for the chromium hydride material. No crysalline regions for chromium hydride sample Cr-25C—$H_2$ were observed.

Figure 11:
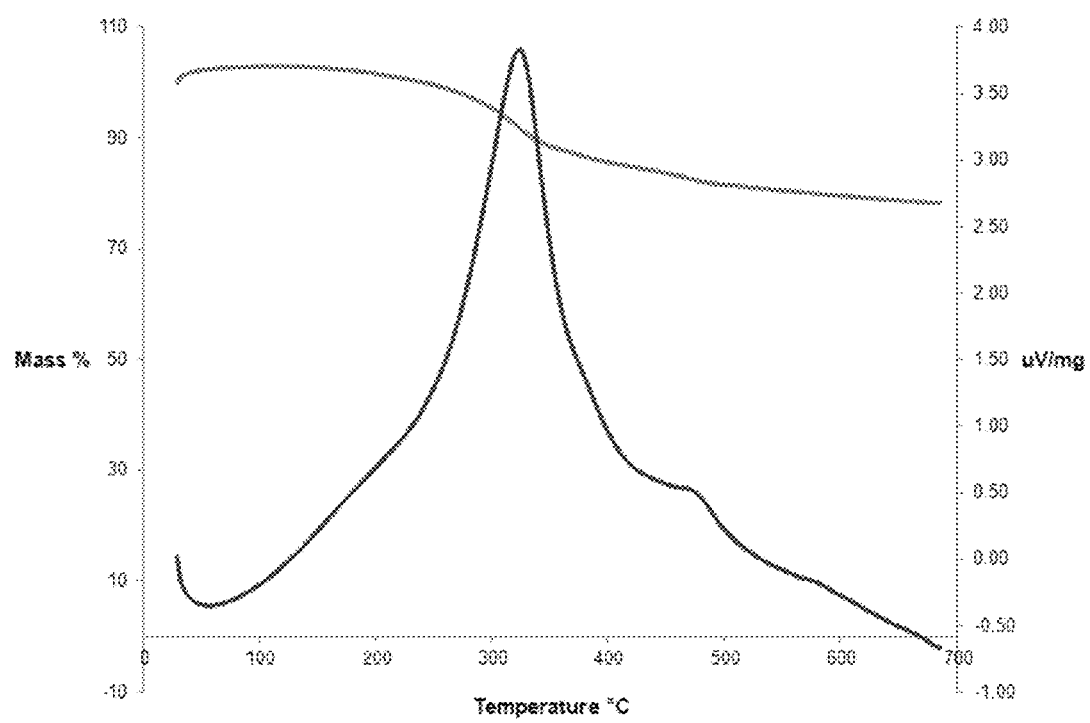
FIG. 11 depicts the differential thermal analysis (DTA) (bottom trace) and thermogravimetric analysis (TGA) (top trace) spectra for chromium hydride sample Cr-100.
Figure 12:
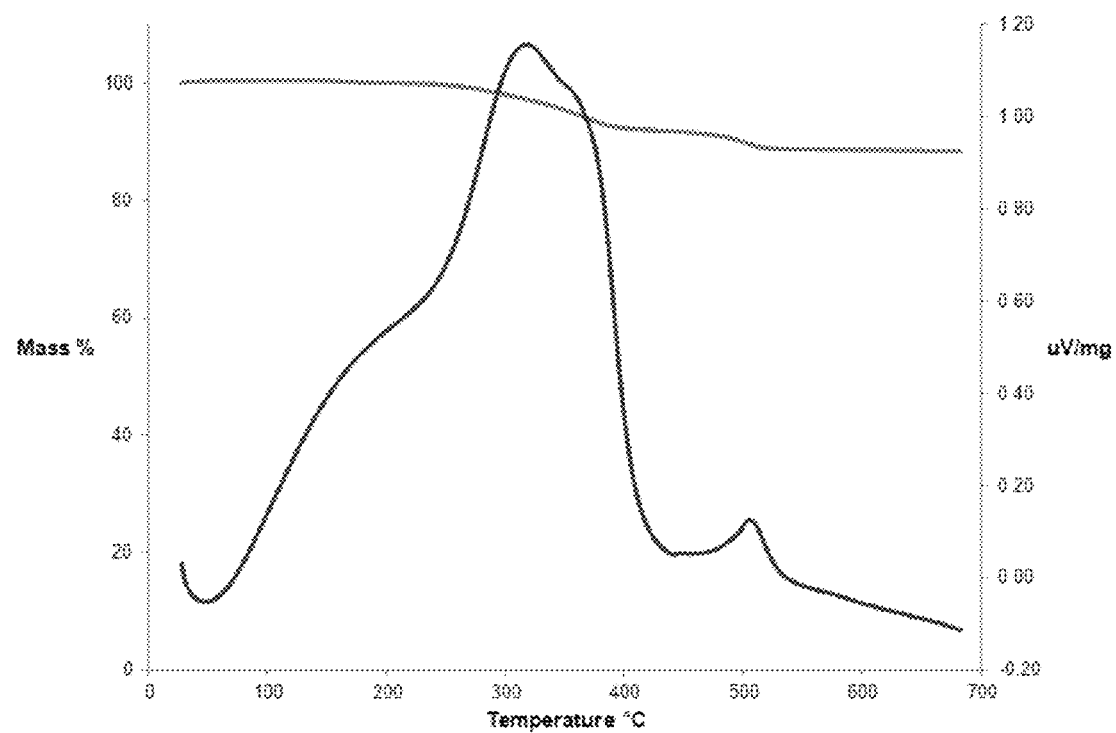
FIG. 12 depicts the differential thermal analysis (DTA) (bottom trace) and thermogravimetric analysis (TGA) (top trace) spectra for chromium hydride sample Cr-150C—$H_2$.
Figure 13:
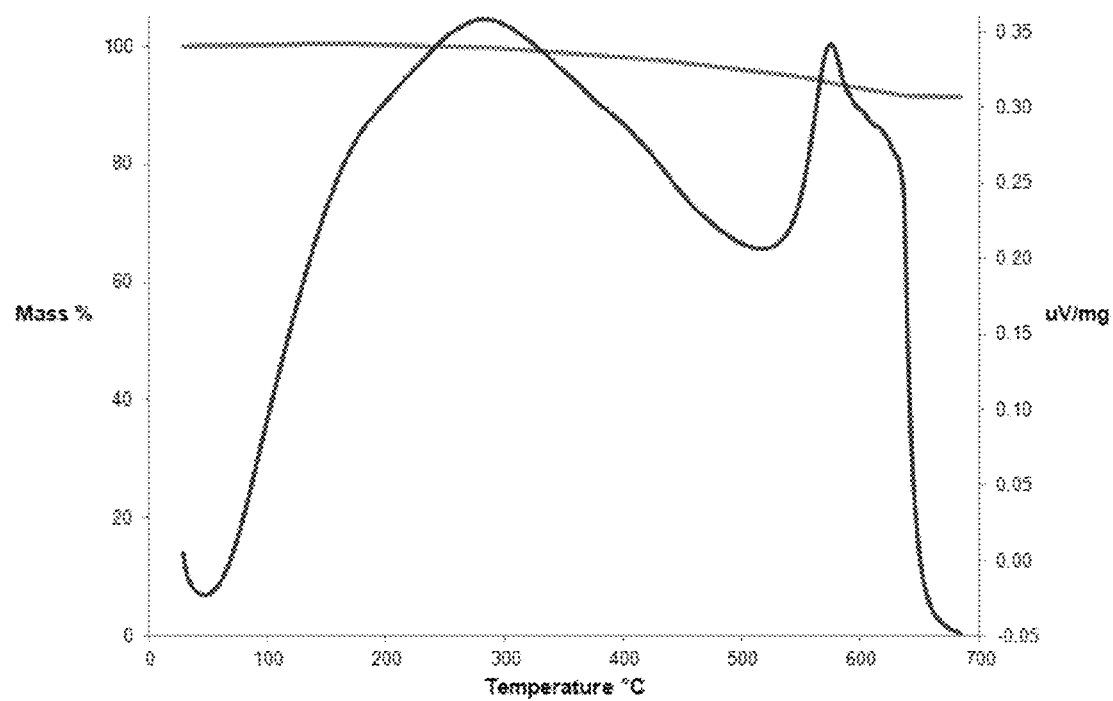
FIG. 13 depicts the differential thermal analysis (DTA) (bottom trace) and thermogravimetric analysis (TGA) (top trace) spectra for chromium hydride sample Cr-25C—$H_2$.
Figure 14:
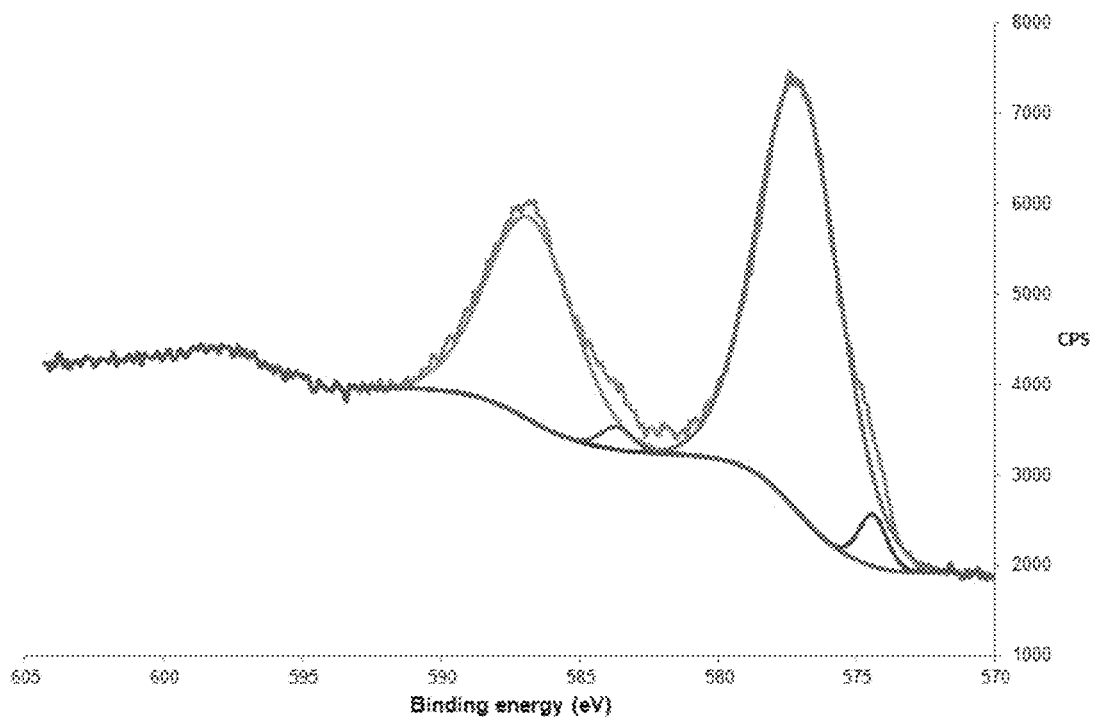
FIG. 14 depicts the peak fitting of chromium $2p_{1/2}$ and $2p_{3/2}$ region in the X-ray photoelectron spectrum (XPS) of sample Cr-100.
Figure 15:
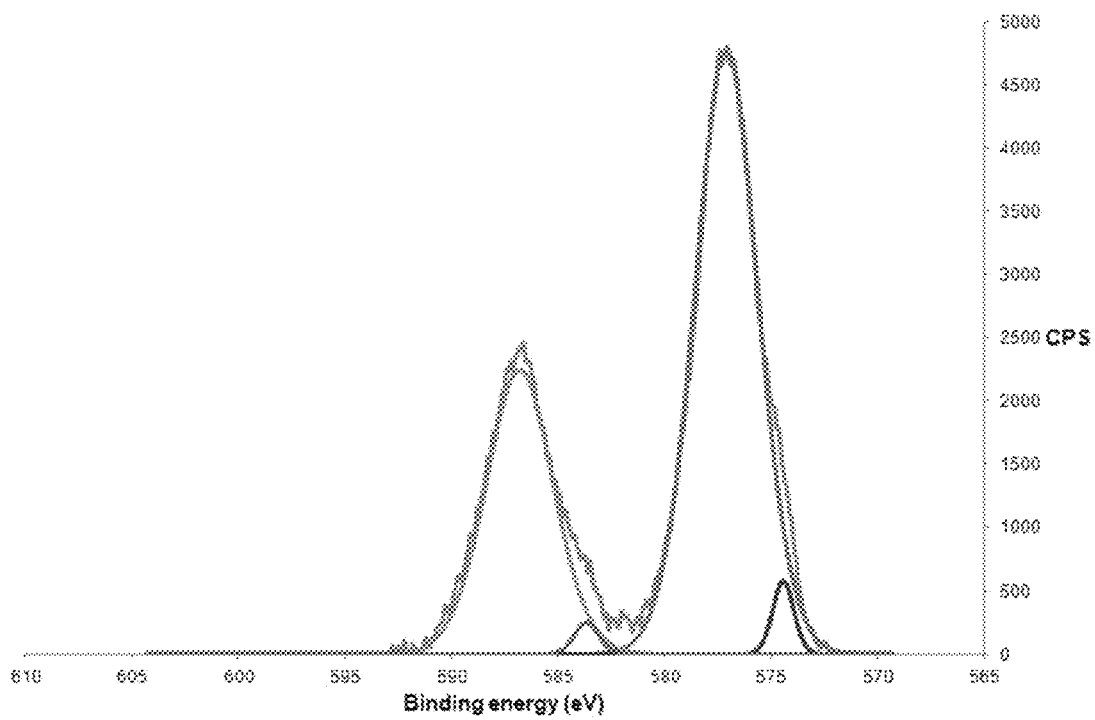
FIG. 15 depicts the baseline corrected peak fitting of chromium $2p_{1/2}$ and $2p_{3/2}$ region in the X-ray photoelectron spectrum (XPS) of sample Cr-100.
Figure 16:
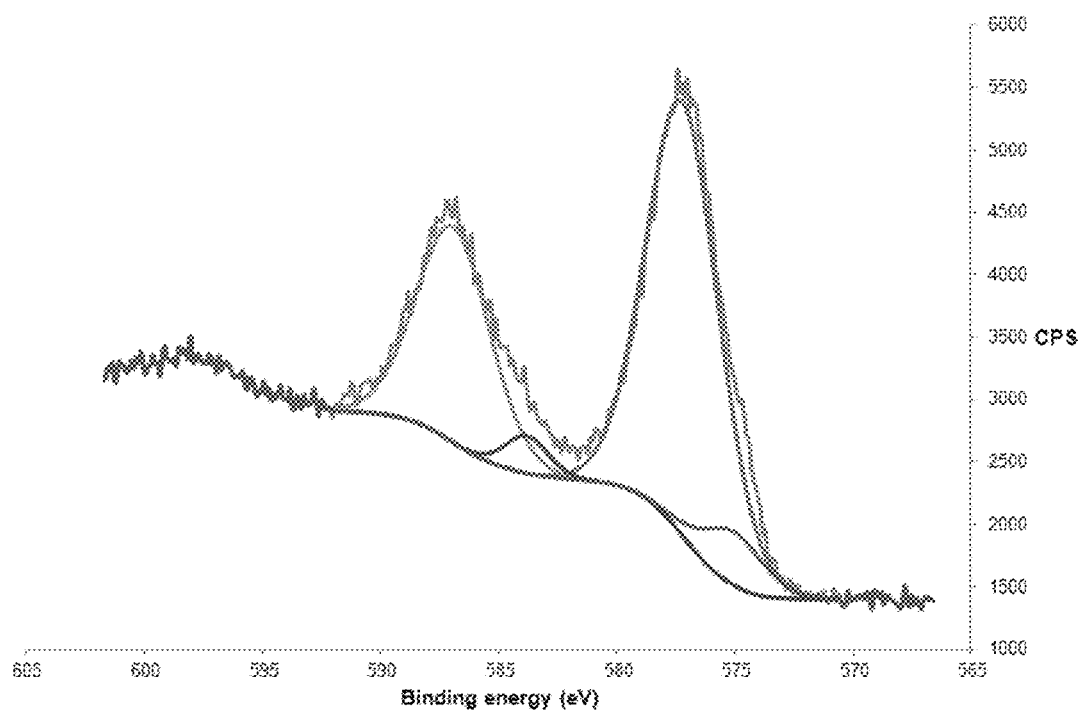
FIG. 16 depicts the peak fitting of chromium $2p_{1/2}$ and $2p_{3/2}$ region in the X-ray photoelectron spectrum (XPS) of sample Cr-150C—$H_2$.
Figure 17:
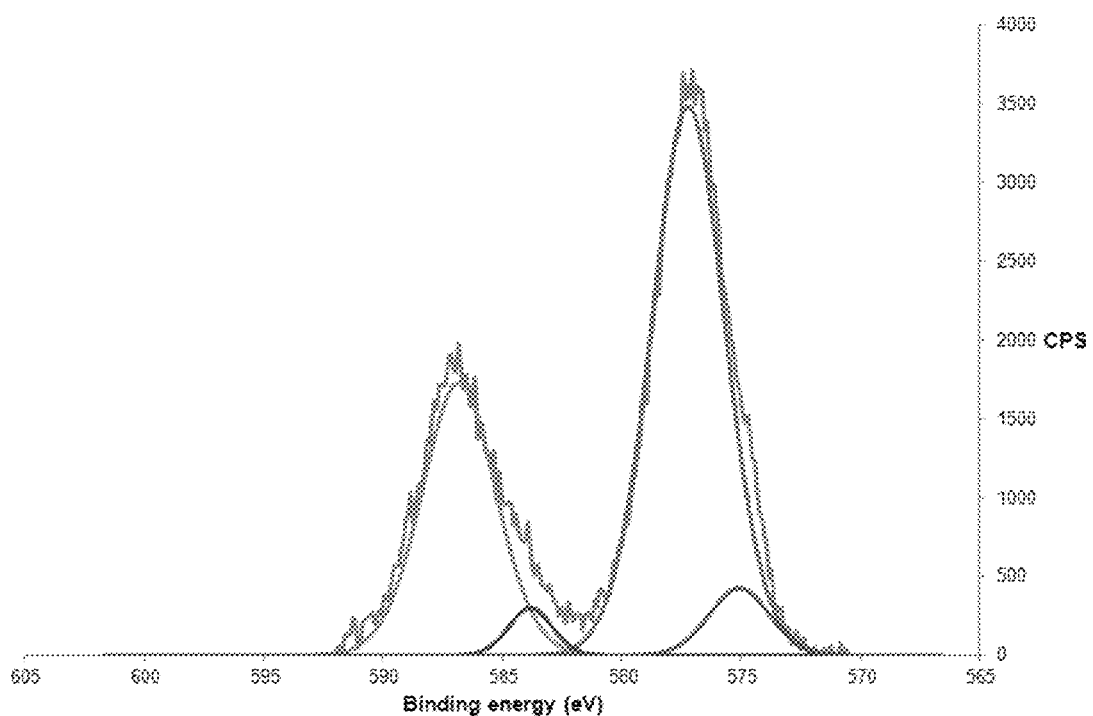
FIG. 17 depicts the baseline corrected peak fitting of chromium $2p_{1/2}$ and $2p_{3/2}$ region in the X-ray photoelectron spectrum (XPS) of sample Cr-150C—$H_2$.
Figure 18:
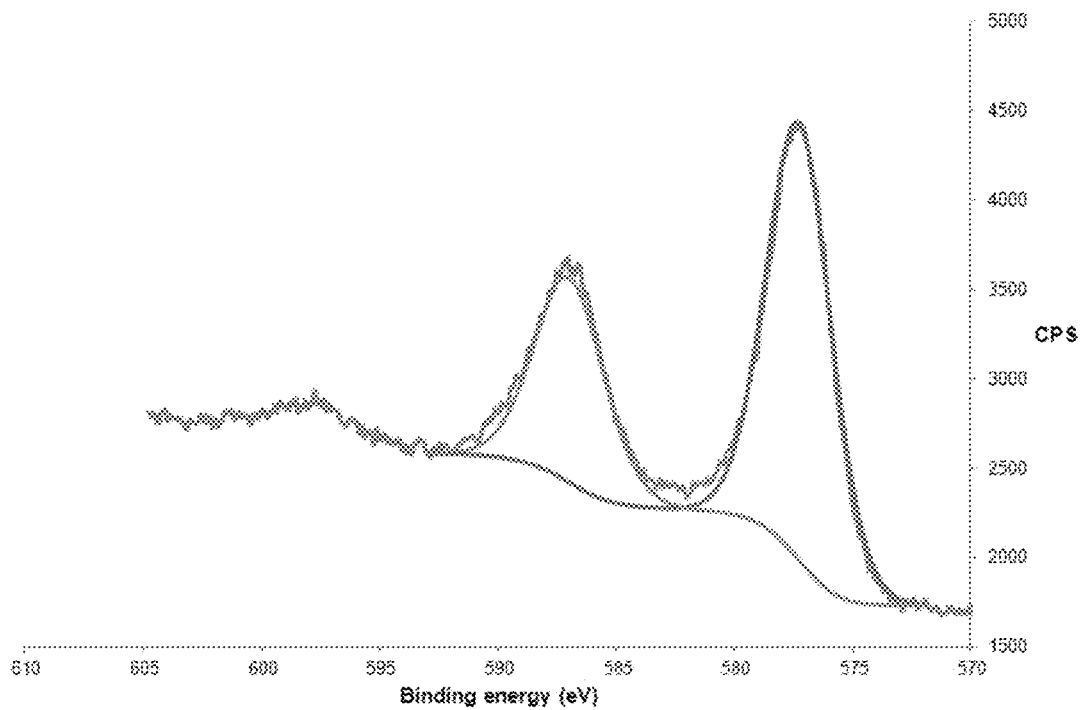
FIG. 18 depicts the peak fitting of chromium $2p_{1/2}$ and $2p_{3/2}$ region in the X-ray photoelectron spectrum (XPS) of sample Cr-25C—$H_2$.
Figure 19:
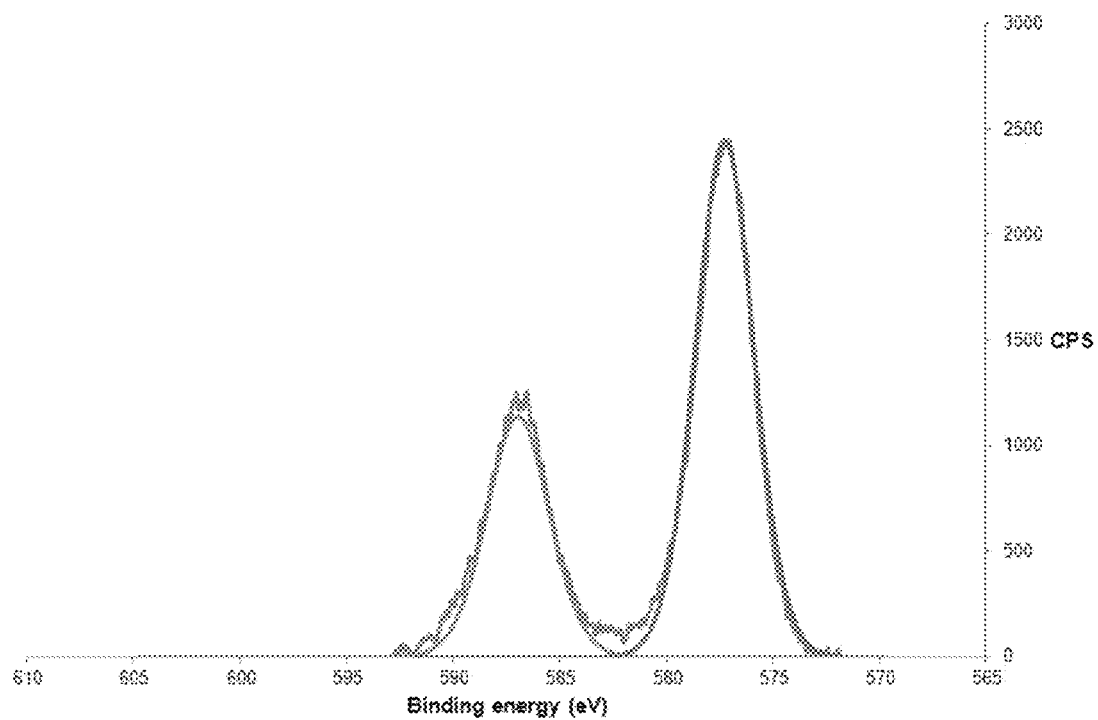
FIG. 19 depicts the baseline corrected peak fitting of chromium $2p_{1/2}$ and $2p_{3/2}$ region in the X-ray photoelecton spectrum (XPS) of sample Cr-25C—$H_2$.

Thermogravimetric analysis was carried out on samples Cr-100, Cr-150C—$H_2$ and Cr-25C—$H_2$ to establish the residual hydrocarbon content of each material after each heat and/or hydrogenation treatment. TGA (top trace) and DTA (bottom trace) spectra for samples Cr-100, Cr-150C—$H_2$ and Cr-25C—$H_2$ are shown in FIGS. 11, 12 and 13, respectively. Initially, sample Cr-100 gains 3% mass at the start of the TGA experiment, due to a slight oxidation of the material during the analysis. The mass then decreases steadily between 135° C. and 686° C. at which the material has retained 78% of its original weight. The loss of 22% in mass is likely due to the combustion of hydrocarbon either as (trimethylsilyl)methyl or bridging alkylidenes present in the material. The DTA curve for sample Cr-100 shows a sharp exothermic peak at 322° C. and a smaller exothermic peak at 470° C. After solid-state hydrogenation at 150° C. and 85 bar $H_2$, sample Cr-150C—$H_2$ demonstrates a clear loss in the amount of hydrocarbon present in the material. The TGA shows that the material looses only 11.5% of its original mass after complete combustion. The DTA curve displays a large, fairly broad exothermic peak at 316° C. and a minor exothermic peak at 506° C. Sample Cr-25C—$H_2$ retained 91.5% of its mass. The DTA curve shows a very broad exothermic peak at 285° C. and a sharper peak at 576° C. The remaining 8.5 wt % of hydrocarbon could not be removed by further hydrogenation for 24 hours at room temperature.

X-ray photoelectron spectroscopy was performed on all three samples and the chromium 2p region is shown in FIGS. 14-19. For samples Cr-100 and Cr-150C—$H_2$ shown in FIGS. 14-17, major $2p_{1/2}$ emissions at 586.9 and 587.3 eV can be assigned to Cr(III) by comparison to the emission at 586.8 eV for Cr(OH)$_3$ (see Desimoni et al., *Surface and Interface Analysis*, 13, 173, 1998). The simulated peak fitting for samples Cr-100 and Cr-150C—$H_2$ also show a minor emission in the $2p_{1/2}$ region at 584 eV which can be assigned to a lower valent Cr species, as the emissions for chromium metal appear at 583.5 eV. Without wishing to be bound by theory, the inventor theorizes that the thermal precipitation of sample Cr-100 from the Cr(IV) tetra alkyl precursor may cause a reduction of the oxidation state to +3, suggesting that reductive Cr—C bond homolysis occurs in addition to the α-hydrogen abstraction necessary to form a polymer. After hydrogenation of sample Cr-100 to form sample Cr-150C—$H_2$, the +3 oxidation state was retained, indicating that the hydrogen does not act as a reducing agent, but replaces the hydrocarbon ligands with hydrides. For sample Cr-25C—$H_2$ in FIGS. 18 and 19, one major emission in the $2p_{1/2}$ region is observed at 586.9 eV, which can be assigned to a chromium (III) species by comparison to Cr(OH)$_3$.

Figure 20:
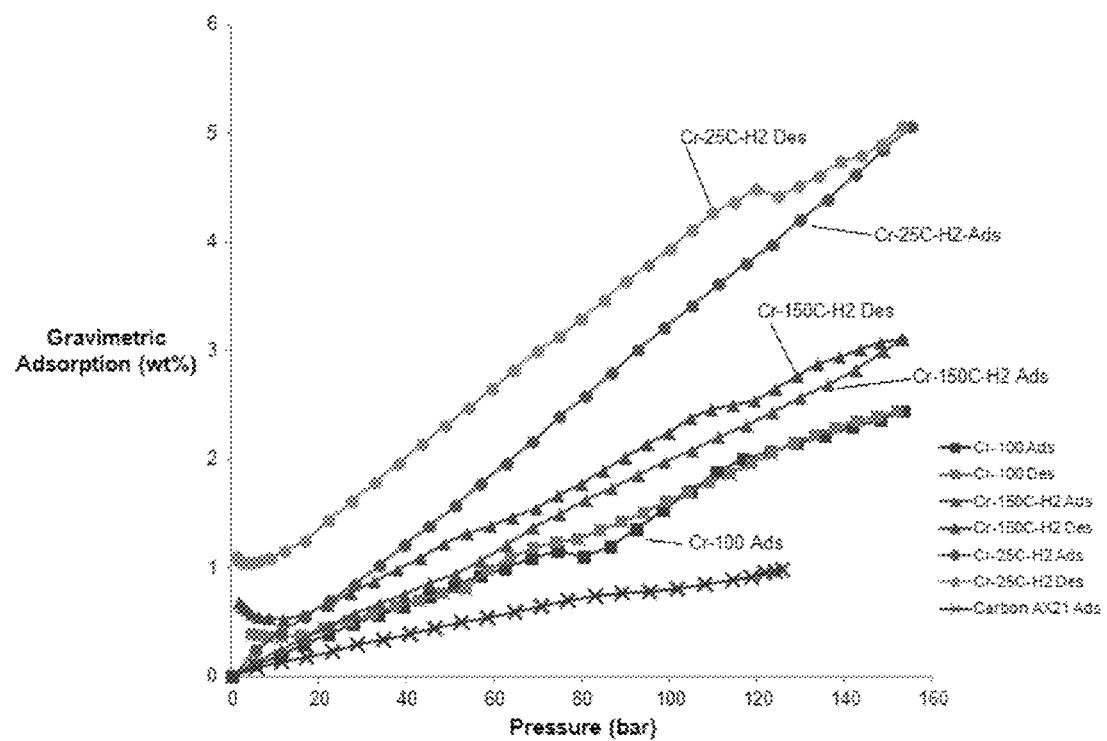
FIG. 20 depicts the hydrogen adsorption-desorption isotherm at 298 K for chromium hydride samples Cr-100, Cr-150C—$H_2$ and Cr-25C—$H_2$.

The gravimetric hydrogen adsorption-desorption isotherms for samples Cr-100, Cr-150C—$H_2$ and Cr-25C—$H_2$ are shown in FIG. 20. For all three materials, the isotherms increase linearly with increasing pressure without saturation at 150 bar. For sample Cr-100 the material reached 2.44 wt % at 150 bar. There is no hysteresis between the adsorption and desorption isotherms showing reversibility of hydrogen adsorption. After hydrogenation in the solid state at 150° C. and 85 bar $H_2$, the performance of the material increased slightly to 3.1 wt % at 150 bar without saturation. Sample Cr-25C—$H_2$ reached a maximum of 5.07 wt % at 150 bar. Although some loss of performance may be expected on incorporation into a system, this value is very close to the U.S. DOE's gravimetric system adsorption goal of 5.5 wt %. As saturation of hydrogen adsorption was not seen at 150 bar it is possible that gravimetric performance could be improved at pressures above 150 bar. To ensure accuracy, carbon AX-21 was used as a standard.

Figure 21:
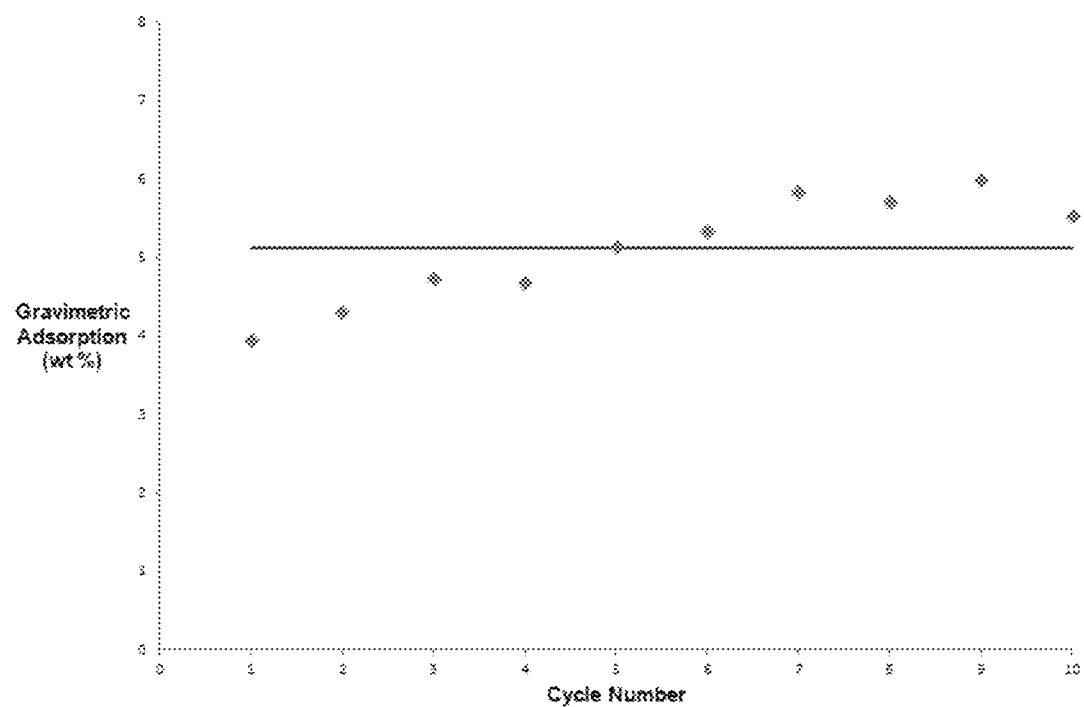
FIG. 21 depicts the life cycle hydrogen adsorption (wt. %) for 10 absorption-desorption cycles between 0 and 150 bar $H_2$ for chromium hydride sample Cr-25C—$H_2$.

FIG. 21 shows the PCT hydrogen adsorption-desorption isotherm for Cr-25C—$H_2$ after 10 adsorption-desorption cycles. Errors are estimated at ±0.07 wt %. Cycling repeated adsorption and desorption of Cr-25C—$H_2$ between 0 and 150 bar demonstrated that the material does not lose activity over 10 cycles. This is an important property for commercialization of hydrogen storage materials for vehicle applications. The average adsorption at 150 bar over the 10 cycles was 5.12 wt %.

Figure 22:
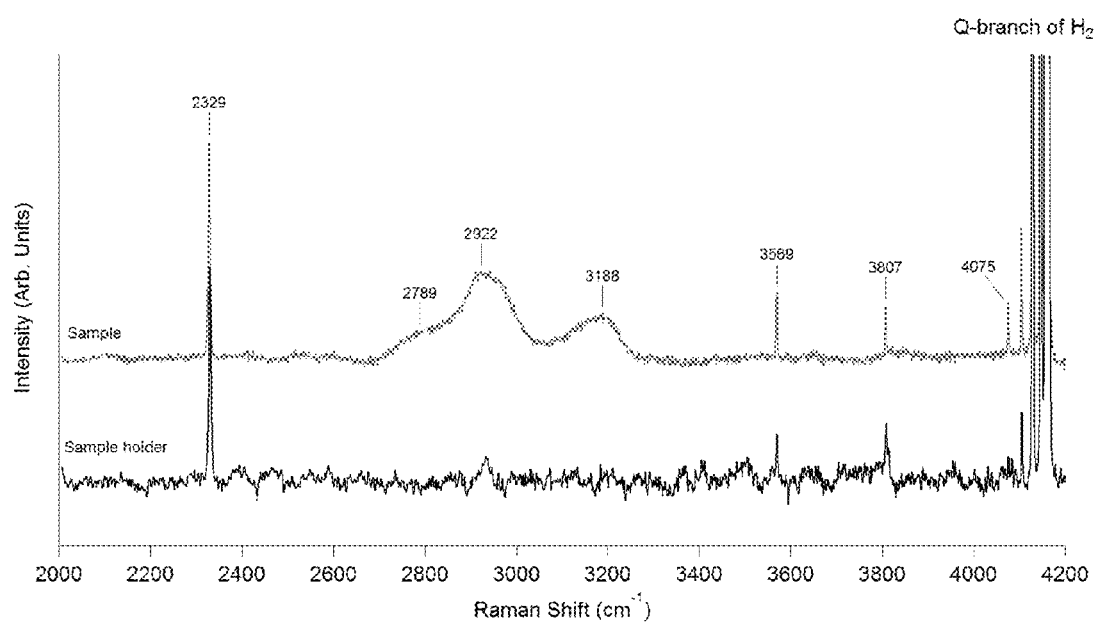
FIG. 22 depicts the Raman spectra of sample Cr-25C—$H_2$ under 50 bar $H_2$ (top trace) and the empty sample holder pressurized at 50 bar $H_2$ (bottom trace).
Figure 23:
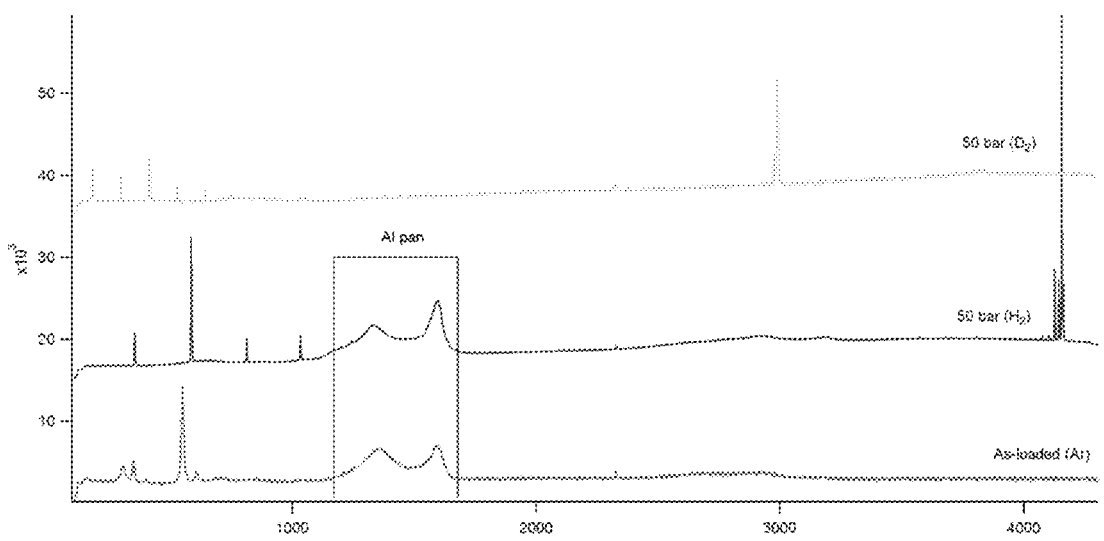
FIG. 23 depicts the full Raman spectrum of sample Cr-25C—$H_2$ under 50 bar $D_2$ (top trace), 50 bar $H_2$ (middle trace) and under argon (bottom trace).

High pressure Raman spectroscopy was employed to study the binding mechanism of sample Cr-25C—$H_2$ with hydrogen. FIG. 22 shows an expanded region of the Raman spectra of sample Cr-25C—$H_2$ at 50 bar hydrogen and also the blank sample holder at 50 bar $H_2$. The full spectra are shown in FIG. 23. In both the empty sample holder and the spectra of sample Cr-25C—$H_2$ signals are observed at 3568 and 3807 cm$^{-1}$, which are due to a system effect. The signal at 4075 cm$^{-1}$ is observed in the spectrum of sample Cr-25C—$H_2$ only and arises from physisorbed $H_2$. The Q-branch for free hydrogen also appears in both spectra between approx. 4128 and 4163 cm$^{-1}$. Calculations indicate that the H—H stretching frequency for a Kubas bound $H_2$ to a chromium (III) hydrazine species should be observed between 3847 and 3936 cm$^{-1}$ (see Skipper et al., *J. Phys. Chem. C*, 116, 19134, 2002). In the spectrum of sample Cr-25C—$H_2$ under hydrogen there are 3 signals at 2789, 2922 and 3188 cm$^{-1}$, which can be assigned as Kubas bound $H_2$. These signals are similar to those observed for Kubas bound $H_2$ on Ti(III) hydride gels (see Hoang et al., *Chem. Mater.*, 25, 4765, 2013), but are broader, possibly due to a greater dispersion of binding sites in the amorphous Cr material. Raman spectra were also obtained under $D_2$. See FIG. 23. Most noticeably, the Q-branch moved to a lower frequency as expected from the isotope effect. The bands at 2789 and 3188 cm$^{-1}$ are no longer present, while the band at 2922 cm$^{-1}$ is now obscured by the Q-branch.

Figure 24:
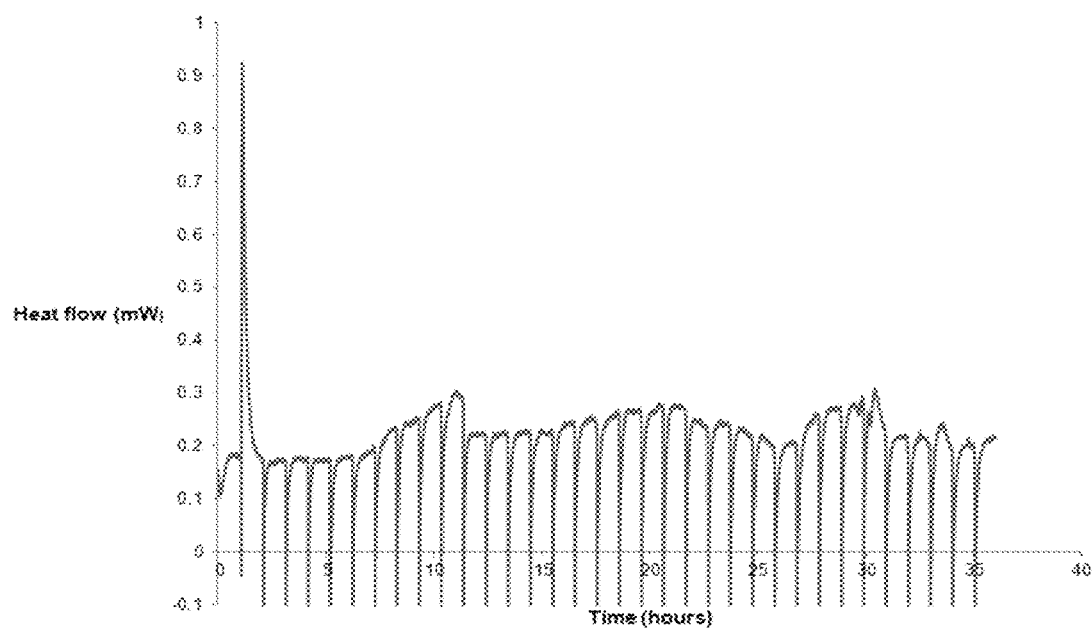
FIG. 24 depicts the calorimetric curves for sample Cr-25C—$H_2$ during each addition of $H_2$ in a PCT hydrogen adsorption measurement.

Calorimetric curves for sample Cr-25C—$H_2$ during each dose of hydrogen addition during the PCT absorption measurement are shown in FIG. 24. In contrast to the calorimetric curves for carbon AX-21 that are exothermic, it can be seen from FIG. 24 that the adsorption process for sample Cr-25C—$H_2$ is slightly endothermic, apart from the first dose of hydrogen which is exothermic. The first exothermic dose may arise from physisorption of $H_2$ or due to the availability of some Kubas binding sites. The enthalpy of hydrogen adsorption for sample Cr-25C—$H_2$ is +0.37 kJ mol$^{-1}$ $H_2$.

Example 2

Vanadium (IV) Hydride Samples

Synthesis
Preparation of Tetraphenyl Vanadium (IV)

Figure 25:
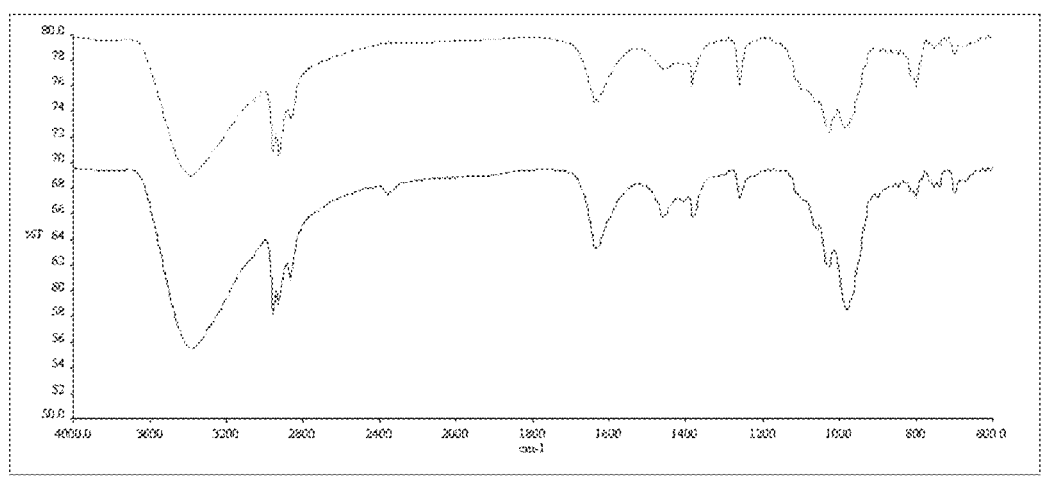
FIG. 25 depicts the IR spectrum of vanadium hydride samples V(IV)-100 (bottom trace) and V(IV)-25-$H_2$ (top trace).

Phenyllithium (50 mmol, 25 mL of a 2.0M solution in dibutylether) was stirred at room temperature. VCl$_4$ (2.03 mL, 12.5 mmol) was then added dropwise via syringe. The reaction mixture turned dark brown in colour, increased in temperature and bubbled fairly vigorously. Stirring was continued for fifteen minutes until it had stopped bubbling and had cooled back to room temperature. The mixture was then filtered to afford a dark brown precipitate and a brown filtrate. The resulting tetraphenyl vanadium (IV) complex was used without further purification.
Formation of Vanadium (IV) Hydride The filtrate was immediately transferred to a stainless steel PARR pressure vessel and stirred under an inert atmosphere for 48 hours at 100° C. The mixture was then filtered to afford a black precipitate. The precipitate was dried in vacuo for four hours at 100° C. to afford 228 mg of a fine black powder (V(IV)-100). The black powder was hydrogenated in the PARR vessel at a pressure of 70 bar for 48 hours at 25° C. The resulting material was then dried in vacuo for 4 hours at 100° C. and allowed to cool to room temperature to give 109.3 mg of a black powder (V(IV)-25C—$H_2$).
Sample Characterization The Infra-Red (IR) spectra for samples V(IV)-100 and V(IV)-25C—$H_2$ are shown in FIG. 25. For sample V(IV)-100, C—H stretches are observed at 2958 cm$^{-1}$, 2919 cm$^{-1}$ and 2868 cm$^{-1}$. The intensity of the C—H stretches decrease slightly after room temperature hydrogenation at 70 bar (sample V(IV)-25C—$H_2$) as the hydrocarbon ligands are replaced by hydrides during hydrogeneolysis. Typically transition metal-hydride bonds are observed in the region of 1900±300 cm$^{-1}$ region however they can be weak in intensity (see Kaesz et al., *Chem. Rev.*, 72, 231, 1972). There is a stretch in this region at 1633 cm$^{-1}$ for sample V(IV)-

25C—H$_2$. In KBr, water displays bands at 3300 and 1647 cm$^{-1}$, so the V—H stretch in the spectrum of V(IV)-25C—H$_2$ at 1633 cm$^{-1}$ may possibly be obscured by an O—H stretch from water absorbed by the KBr disc during the rapid transfer step from the glove box to IR apparatus.

Figure 26:
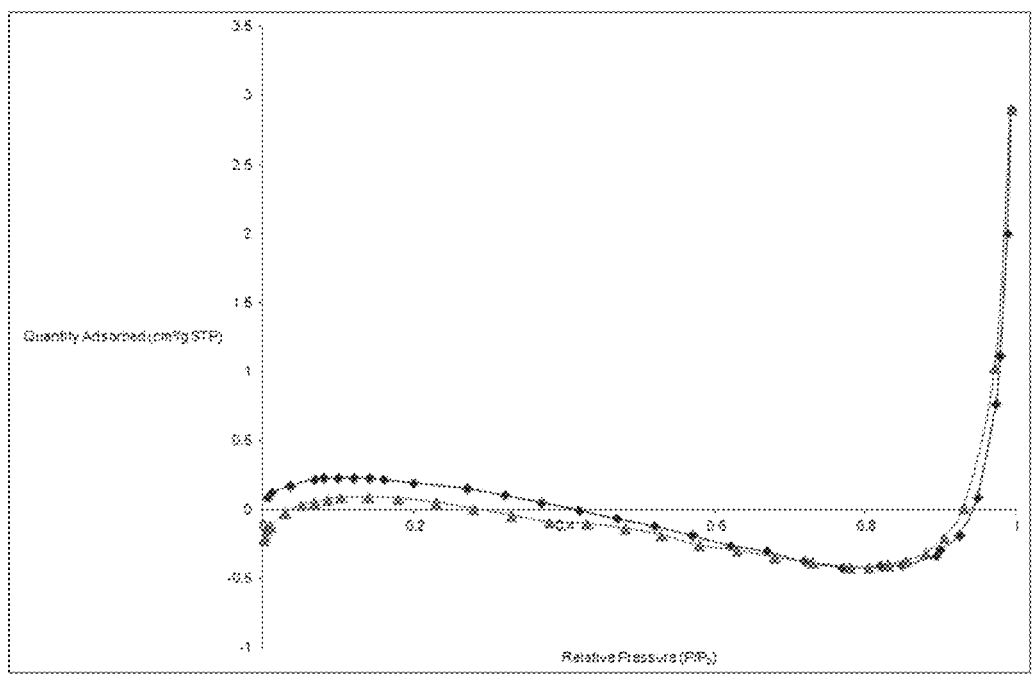
FIG. 26 depicts a nitrogen adsorption (lower trace)-desorption (upper trace) isotherm for vanadium hydride sample V(IV)-100.
Figure 27:
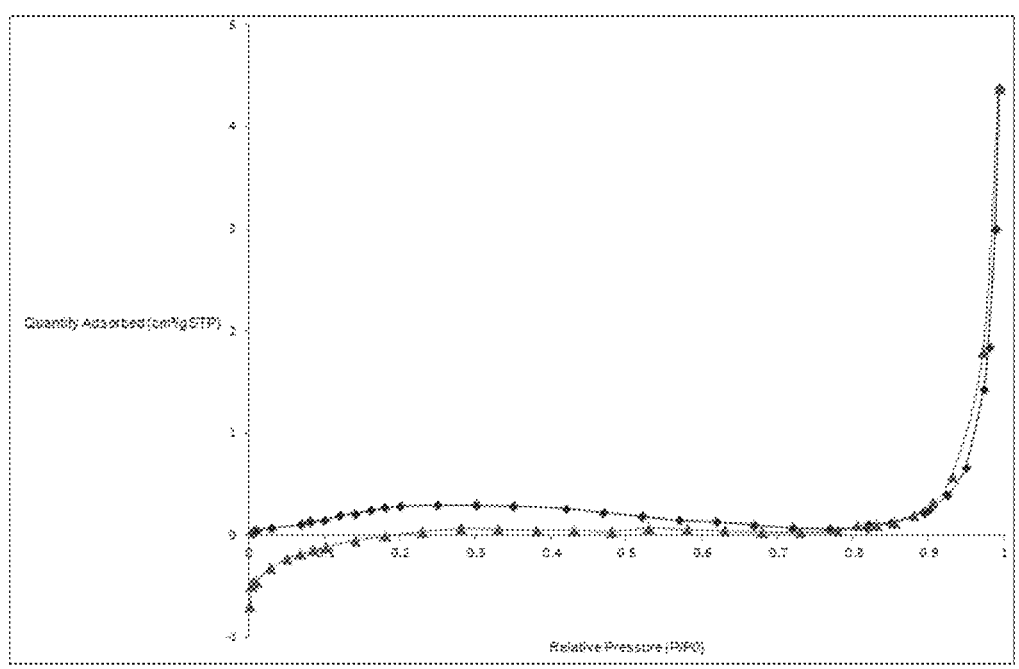
FIG. 27 depicts a nitrogen adsorption (lower trace)-desorption (upper trace) isotherm for vanadium hydride sample V(IV)-25-$H_2$.

Nitrogen adsorption-desorption isotherms for Samples V(IV)-100 and V(IV)-25C—H$_2$ recorded at 77K are shown in FIGS. 26 and 27, respectively. Both samples possess a type 2 isotherm. The BET surface area of sample V(IV)-100 is 0.6 m$^2$/g. After hydrogenation, the surface area of sample V(IV)-25C—H$_2$ increased to 2.2 m$^2$/g. The increase in surface area may be due to loss of hydrocarbon from the material creating new pathways in the material. There is no significant increase in slope between 0 and 0.1 P/Po indicating that there is no microporosity in both materials. The increasing slope between 0.8 and 1.0 P/Po arises from textural porosity.

Figure 28:
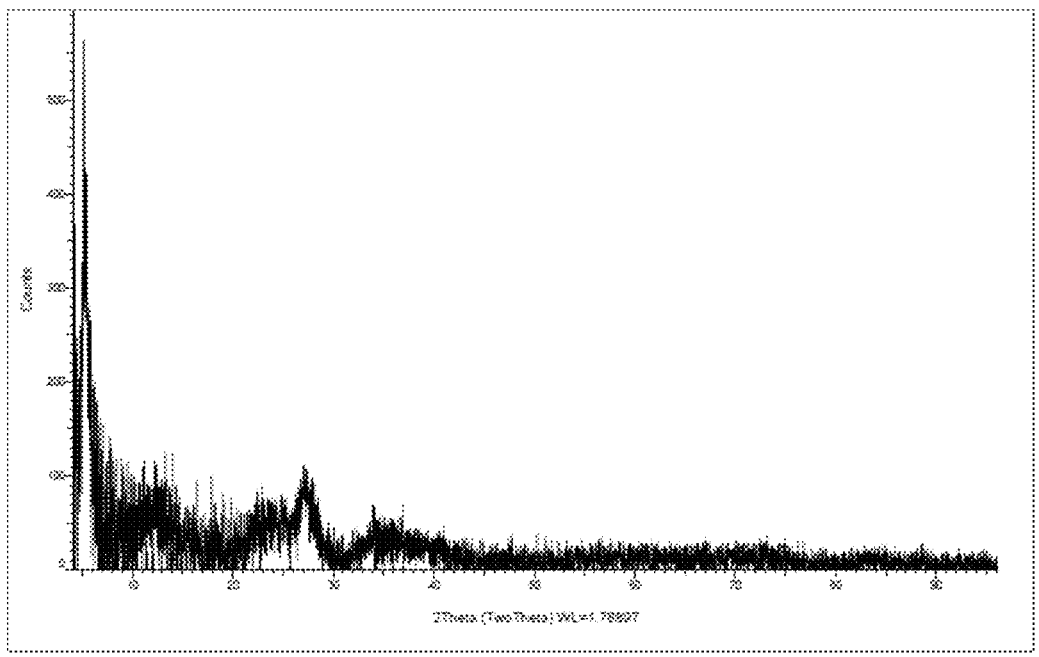
FIG. 28 depicts an X-ray powder diffraction (XRPD) pattern of vanadium hydride sample V(IV)-25-$H_2$.

The X-ray powder diffraction (XRPD) pattern for sample V(IV)-100 is shown in FIG. 28. The material is largely amorphous. The minor reflections in the 0-30° 2θ region may be attributed to the glass capillaries used during analysis.

Hydrogen Adsorption-Desorption Studies

Figure 29:
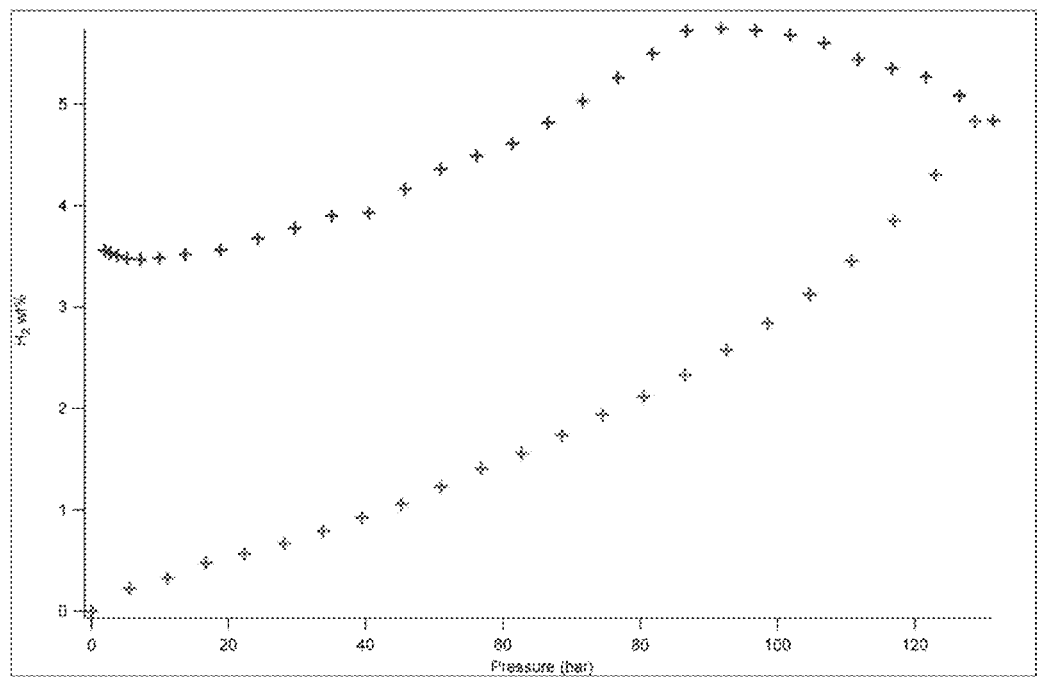
FIG. 29 depicts the hydrogen adsorption (lower trace)-desorption (upper trace) isotherm at 298 K for vanadium hydride sample V(IV)-100.
Figure 30:
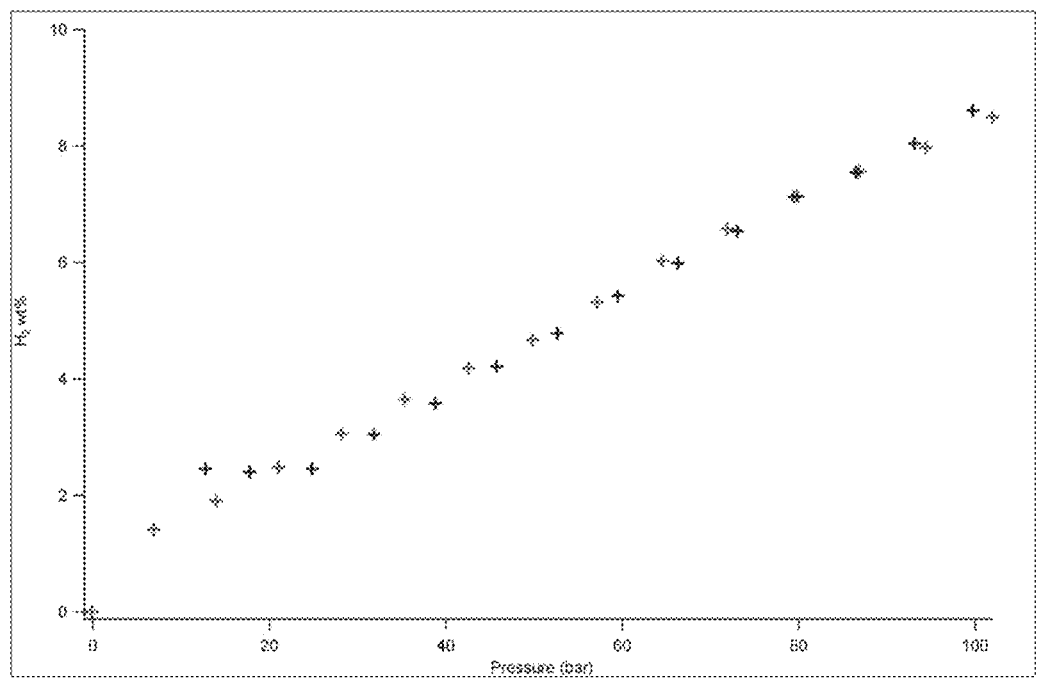
FIG. 30 depicts the hydrogen adsorption (lower trace)-desorption (upper trace) isotherm at 298 K for vanadium hydride sample V(IV)-25-$H_2$.

The gravimetric hydrogen adsorption-desorption isotherms for samples V(IV)-100 and V(IV)-25C—H$_2$ are shown in FIGS. 29 and 30, respectively. The isotherms increase linearly with increasing pressure without saturation at the pressures tested. For sample V(IV)-100, the material reached 3.2 wt % at 141 bar. There is hysteresis in the isotherm, without complete reversibility. Applying vacuum for five minutes at 10$^{-3}$ torr, however, completed desorption so that a second run of adsorption reached 3.2 wt % at 141 bar. Sample V(IV)-25C—H$_2$ reached a maximum of 8.5 wt % at 100 bar. This surpasses the U.S. DOE's gravimetric adsorption goal of 5.5 wt %. To ensure accuracy, carbon AX-21 was used as a standard.

Figure 31:
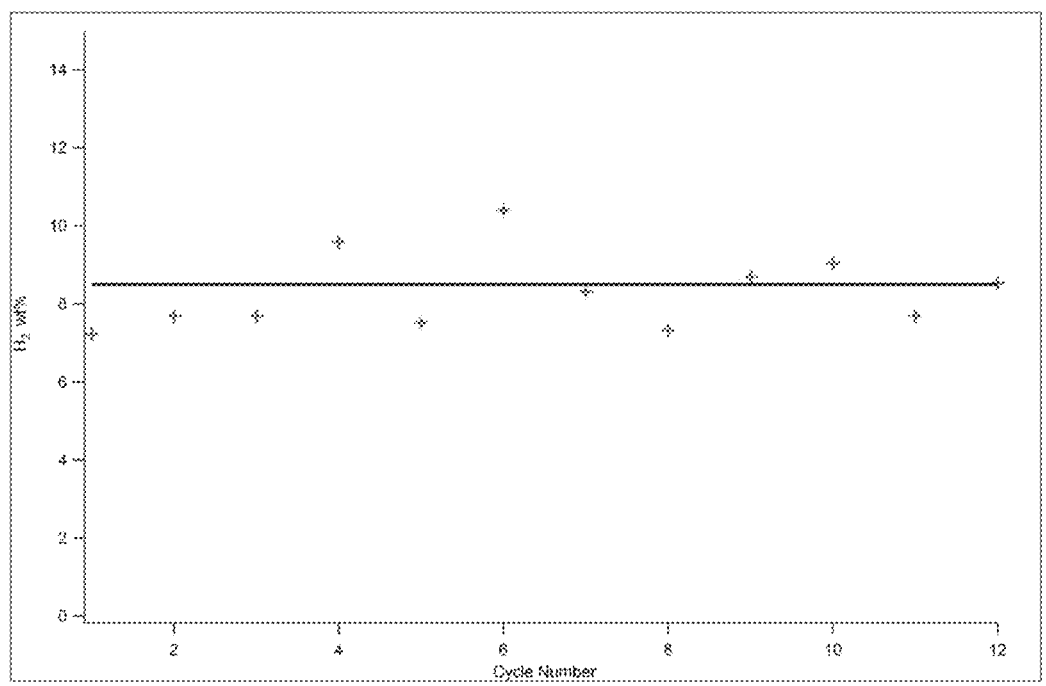
FIG. 31 depicts the life cycle hydrogen adsorption (wt. %) for 12 absorption-desorption cycles between 0 and 100 bar $H_2$ for vanadium hydride sample V(IV)-25-$H_2$.

FIG. 31 shows the PCT hydrogen adsorption-desorption isotherm for V(IV)-25C—H$_2$ after 12 adsorption-desorption cycles. Cycling repeated adsorption and desorption of V(IV)-25C—H$_2$ between 0 and 100 bar demonstrated that the material does not lose activity over the 12 cycles. The average adsorption at 100 bar over the 12 cycles was 8.5 wt %.

Example 3

Manganese (II) Hydride Samples

Synthesis
Preparation of Bis(Mesityl) Manganese (II)

Manganese (II) chloride (5.0043 g, 39.77 mmol) was stirred with 1,4-dioxane (13.6 mL, 159.08 mmol) at room temperature for 1 hour to afford a pale pink paste. Diethyl ether was then added (50 mL) to afford a pale pink suspension. To this, mesitylmagnesium bromide (79.54 mmol, 79.54 mL of a 1.0 M solution in diethyl ether) was added dropwise at room temperature and the suspension changed from pale pink to brown. The brown suspension was stirred at room temperature for 24 hours, then filtered to afford a red-brown filtrate and a light beige precipitate. The precipitate was rinsed three times with diethyl ether. The washings and filtrate were combined and concentrated in vacuo to afford a red-brown solid. The solid was then extracted into petroleum ether (100 mL) and filtered to give a red-brown filtrate and light brown precipitate. The filtrate was concentrated in vacuo to afford a dark red-brown solid, which was dried in vacuo at room temp to give a red-brown powder (1.95 g, 30%).

Formation of Manganese (II) Hydride

Bis(mesityl) manganese(II) (1.9 g, 6.5 mmol) was stirred in 50 mL of warm petroleum ether to give a red-brown solution. The solution was transferred to a stainless steel PARR hydrogenation vessel under an inert atmosphere which was heated at 100° C. for 48 hours with stirring. The reaction mixture was filtered, and the resulting dark brown precipitate was dried at 100° C. in vacuo for 4 hours to afford a dark brown air-moisture sensitive solid (Mn(II)-100) (120 mg). This material was then reacted with hydrogen gas by placing the powder in the PARR vessel at room temperature and pressurizing the vessel at 100 bar. After 48 hours the material was dried in vacuo at 100° C. for four hours to afford a dark brown fine powder (Mn(II)-25C—H$_2$) (58 mg).

Sample Characterization

Figure 32:
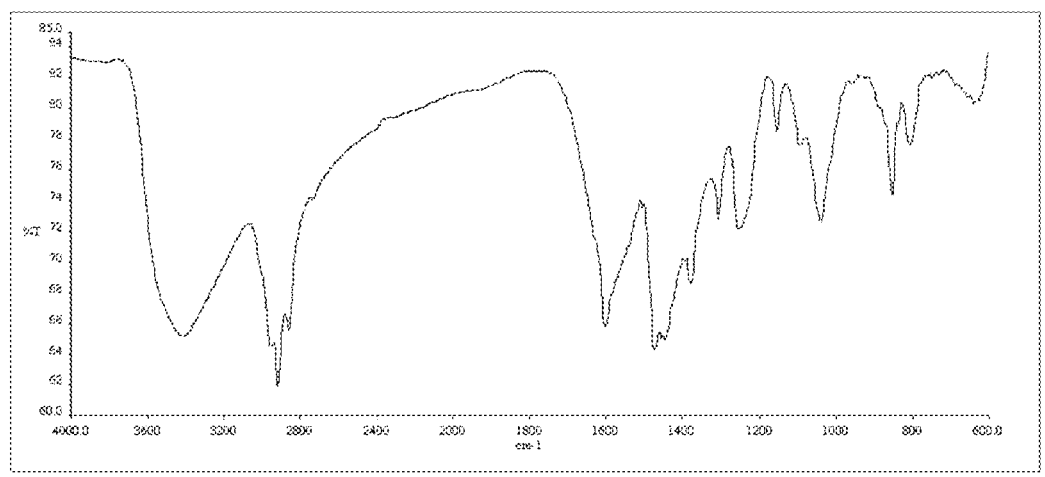
FIG. 32 depicts an IR spectrum of manganese hydride sample Mn(II)-100.
Figure 33:
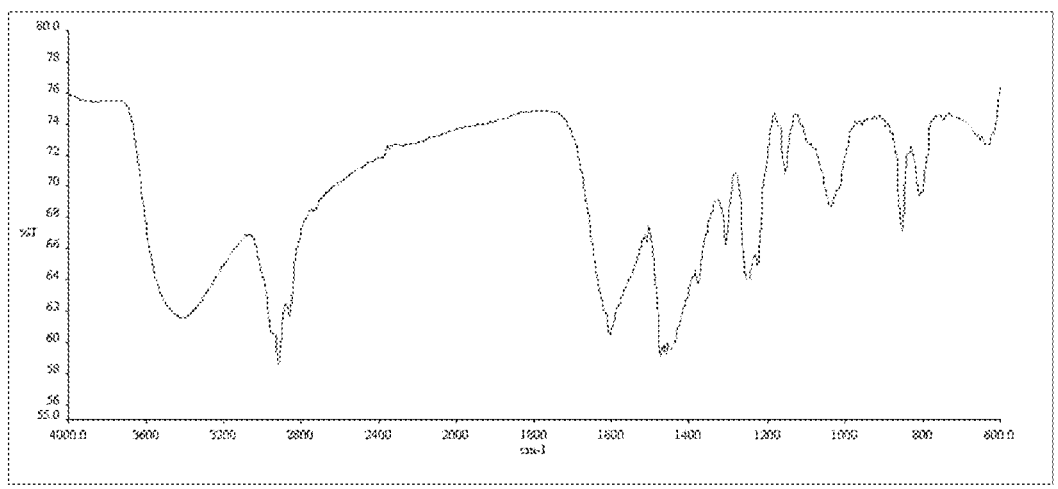
FIG. 33 depicts an IR spectrum of manganese hydride sample Mn(II)-25C—H$_2$.

The Infra-Red (IR) spectra for samples Mn(II)-100 and Mn(II)-25C—H$_2$ are shown in FIGS. 32 and 33, respectively. For sample Mn(II)-100, C—H stretches are observed at 2966 cm$^1$, 2917 cm$^{-1}$ and 2857 cm$^{-1}$. The intensity of the C—H stretches decrease slightly after room temperature hydrogenation at 70 bar (sample Mn(II)-25C—H$_2$) as the hydrocarbon ligands are replaced by hydrides during hydrogenolysis. There is also a stretch at 1740 cm$^{-1}$ in both spectra, partially obscured by a water stretch at 1640 cm$^{-1}$, which falls into the 1900±300 cm$^{-1}$ region for transition metal-hydride stretches. See, e.g., Kaesz et al. *Chem. Rev.*, 72, 231, 1972.

Figure 34:
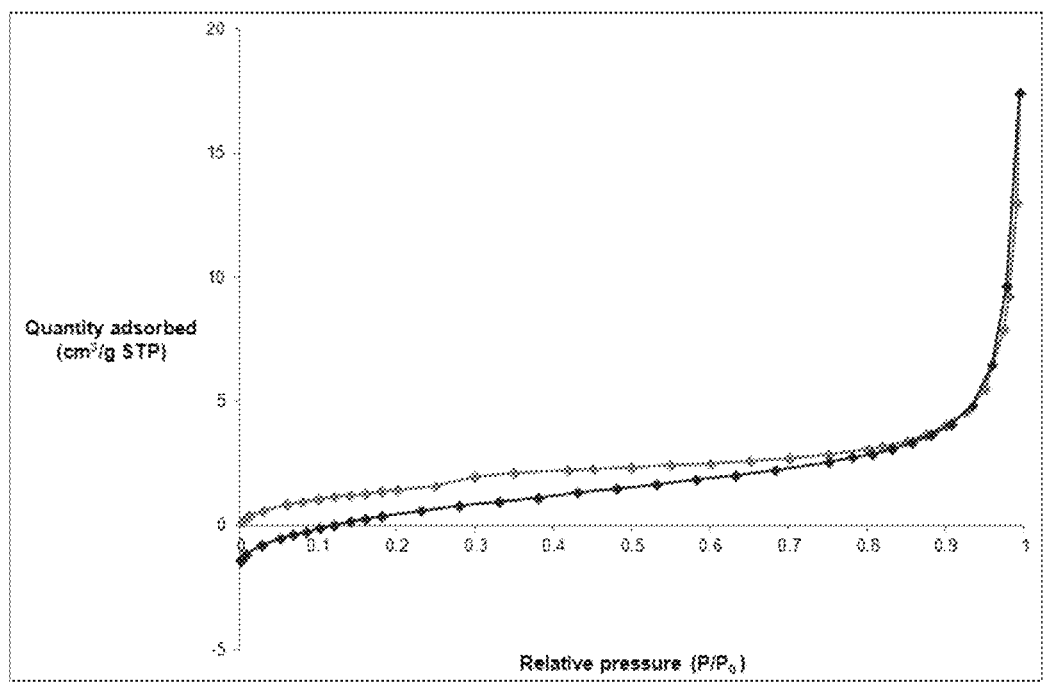
FIG. 34 depicts a nitrogen adsorption (lower trace)-desorption (upper trace) isotherm for manganese hydride sample Mn(II)-100.
Figure 35:
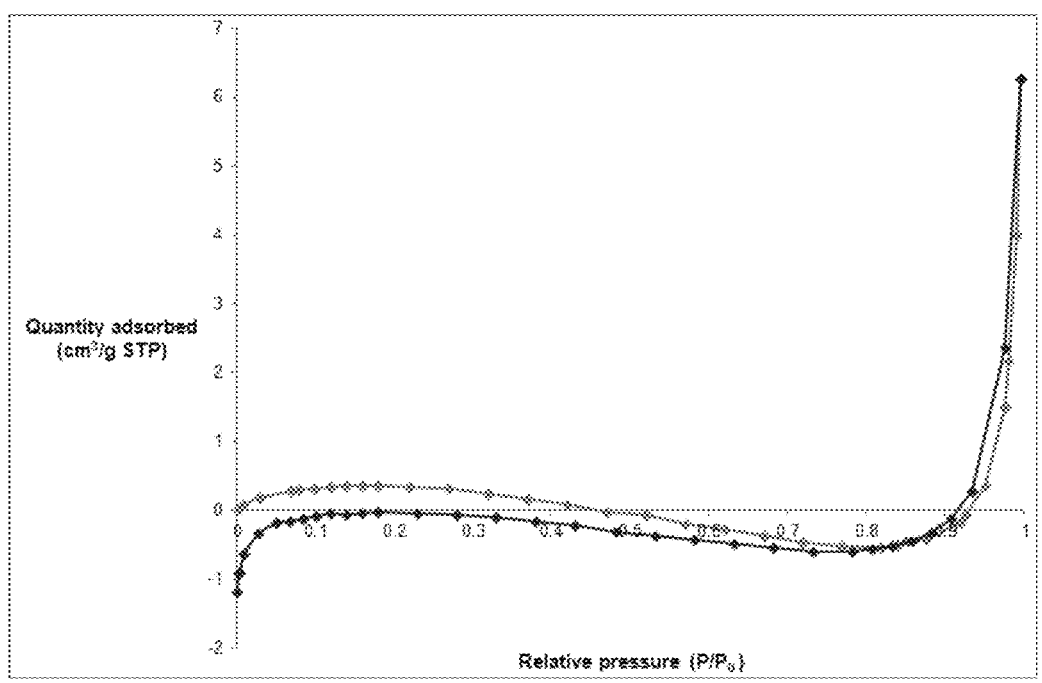
FIG. 35 depicts a nitrogen adsorption (lower trace)-desorption (upper trace) isotherm for manganese hydride sample Mn(II)-25C—H$_2$.
Figure 36:
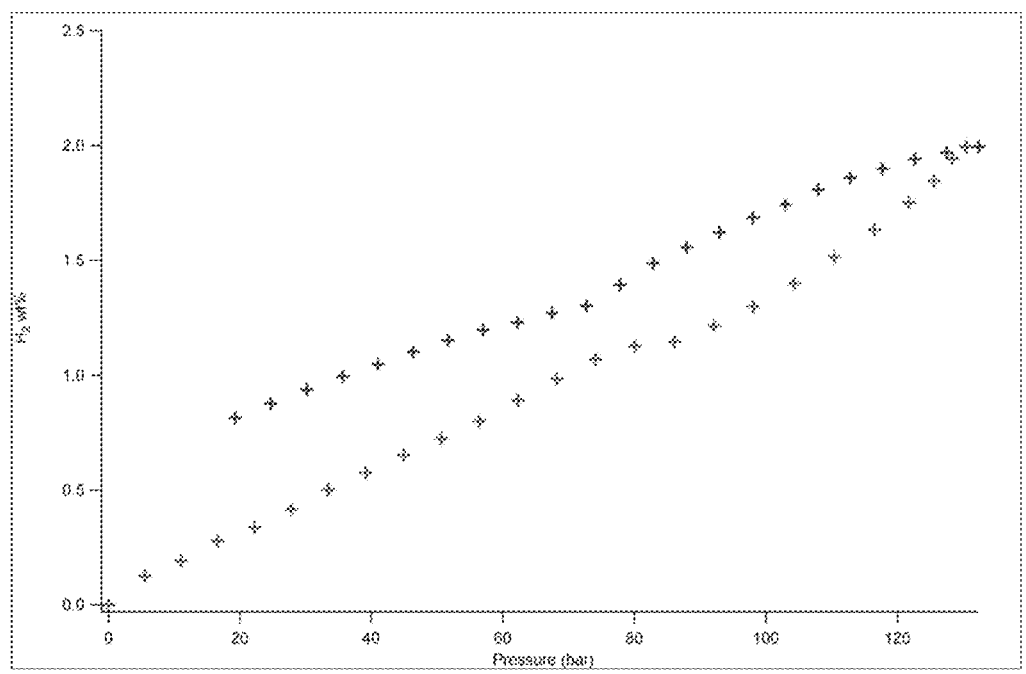
FIG. 36 depicts the hydrogen adsorption (lower trace)-desorption (upper trace) isotherm at 298 K for manganese hydride sample Mn(II)-100.
Figure 37:
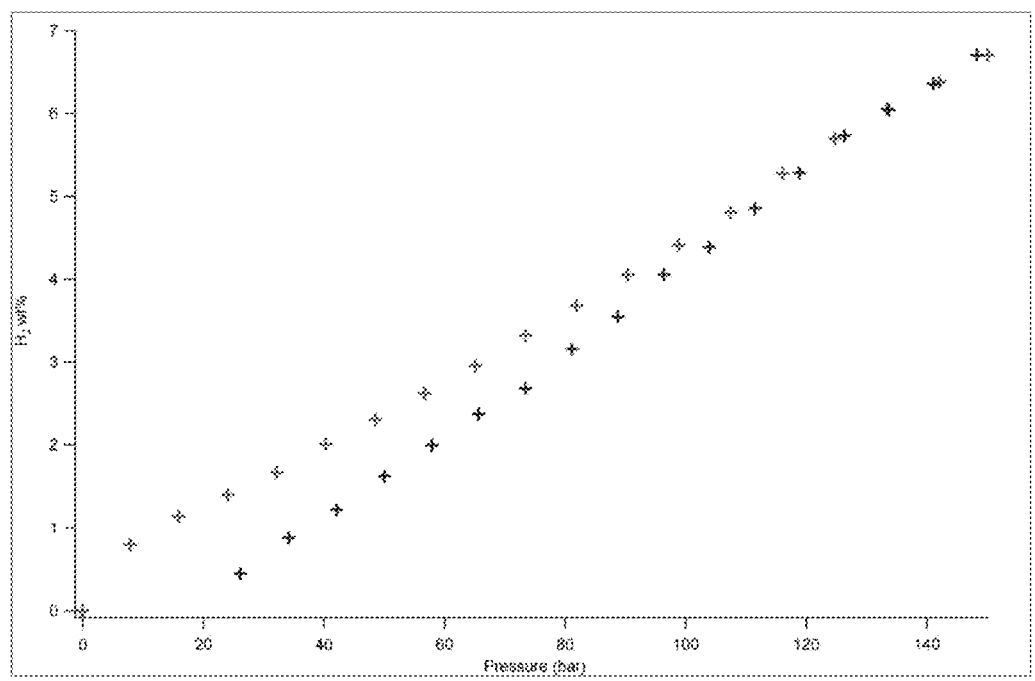
FIG. 37 depicts the hydrogen adsorption (lower trace)-desorption (upper trace) isotherm at 298 K for manganese hydride sample Mn(II)25C—H$_2$.

Nitrogen adsorption-desorption isotherms for Samples Mn(II)-100 and Mn(II)-25C—H$_2$ recorded at 77K are shown in FIGS. 34 and 35, respectively. Sample Mn(II)-100 exhibits a BET surface area of 6 m$^2$/g. After room temperature hydrogenation the BET surface area for sample Mn(II)-25C—H$_2$ decreased to 1.2 m$^2$/g. In both samples there is some hysteresis between the adsorption and desorption isotherms which means that the materials are not nonporous. There is a very little increase in slope between 0 and 0.1 P/Po suggesting that there is no or very little microporosity. The moderate increase in slope between 0.1 and 0.8 P/Po for sample Mn(II)-100 arises from mesoporosity and the increasing slope between 0.8 and 1.0 P/Po arises from textural porosity Hydrogen Adsorption-Desorption Studies The gravimetric hydrogen adsorption-desorption isotherms for samples Mn(II)-100 and Mn(II)-25C—H$_2$ are shown in FIGS. 36 and 37, respectively. The isotherms increase linearly with increasing pressure without saturation. For sample Mn(II)-100, the material reached 2 wt % at 130 bar and there is some small hysteresis between the adsorption and desorption isotherms.

Sample Mn(II)-25C—H$_2$ reached a maximum of 6.7 wt % at 150 bar. This surpasses the U.S. DOE's gravimetric adsorption goal of 5.5 wt %. As saturation of hydrogen adsorption was not seen at 150 bar it is possible that gravimetric performance could be improved at pressures above 150 bar. To ensure accuracy, carbon AX-21 was used as a standard.

Example 4

Manganese (II) Hydride Samples

Series 1

Manganese (II) chloride was stirred with 2 equivalents of neopentyl magnesium chloride in diethylether and with 4 equivalents of dioxane, and the solution stirred for 24 hours at room temperature. The resulting product was isolated by filtration and washed with 100 mL of diethylether. The solvent removed in vacuo and the product was dried at 40° C. for 1 day (86% yield). The resulting product was then dissolved in 40 mL of petroleum ether, filtered and washed with 100 mL of petroleum ether. Solvents were removed in vacuo and the product was dried in vacuo for 4 hours (24% yield). 0.8 g of the product was then dissolved in 100 mL of petroleum ether and placed in the PARR vessel for 2 days at 100° C. (not under an atmosphere of hydrogen). 188 mg of solid was recovered and dried in vacuo for 2 hours to afford 146 mg of a solid (18.2% yield). The Infra-Red (IR) spectra of the resulting product is shown in FIG. 38.

Figure 39:
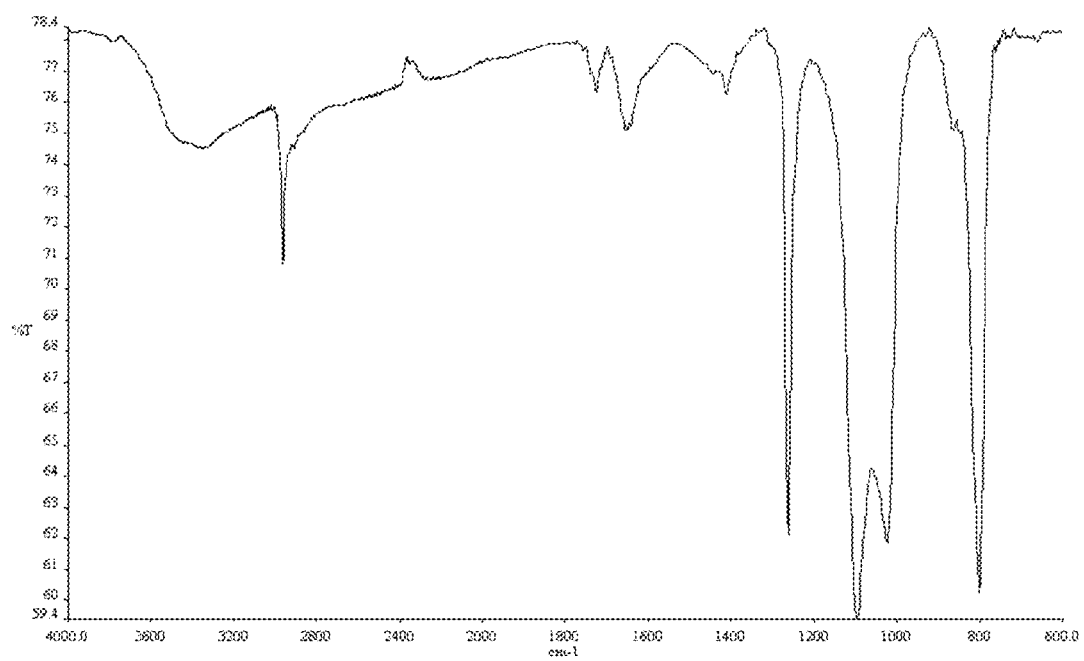
FIG. 39 depicts an IR spectrum of a maganese (II) sample described in Example 4, Series 1.
Figure 40:
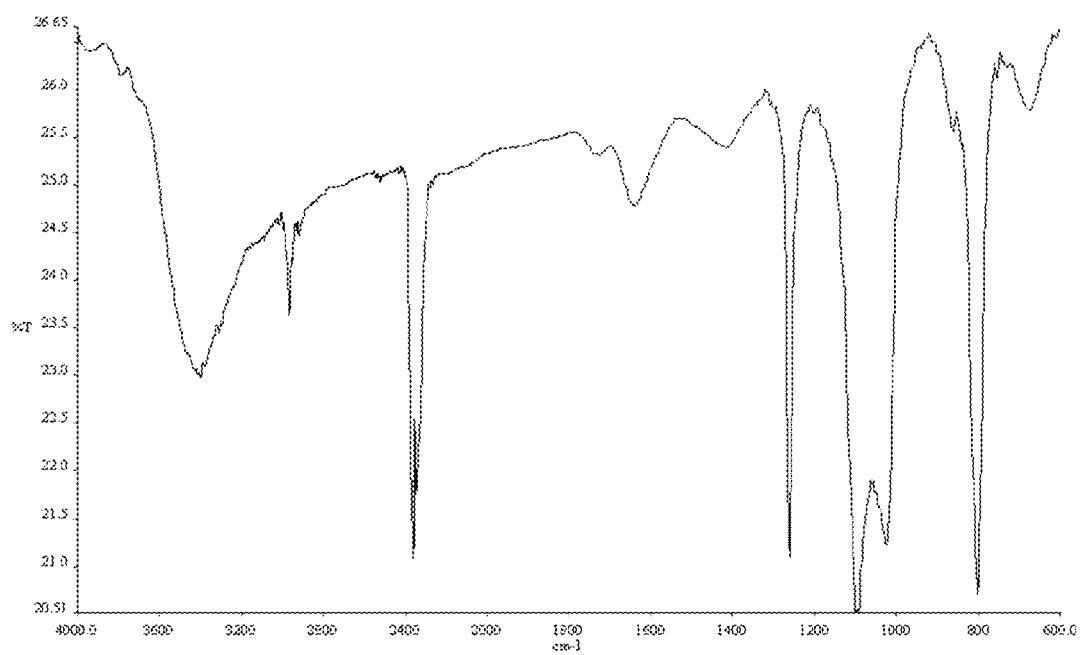
FIG. 40 depicts an IR spectrum of a maganese (II) sample described in Example 4, Series 1, upon exposure to air for 2 minutes.
Figure 41:
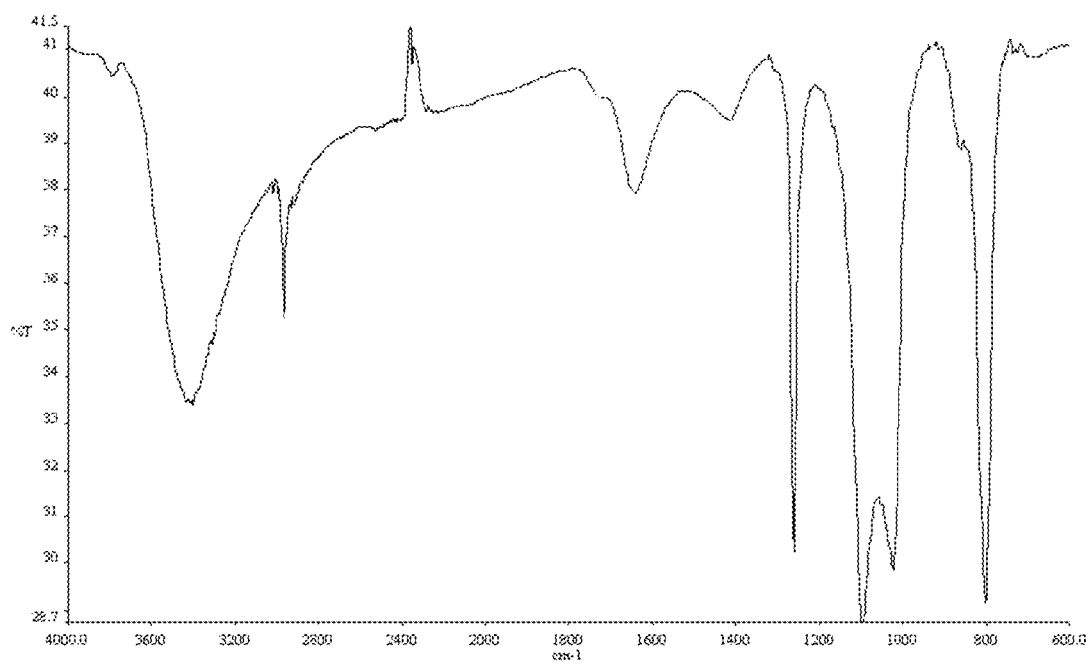
FIG. 41 depicts an IR spectrum of a maganese (II) sample described in Example 4, Series 1, upon exposure to air for 5 minutes.

The product was then hydrogenated at 150° C. and 85 bar $H_2$ for 4 hours. The temperature was reduced to 100° C. and the sample was dried in vacuo for 2 hours. The Infrared (IR) spectrum of the resulting product is shown in FIG. 39. The Infrared (IR) spectra of this same sample taken 2 and 5 minutes after the initial spectrum of FIG. 39 are shown in FIGS. 40 and 41, respectively.

Figure 38:
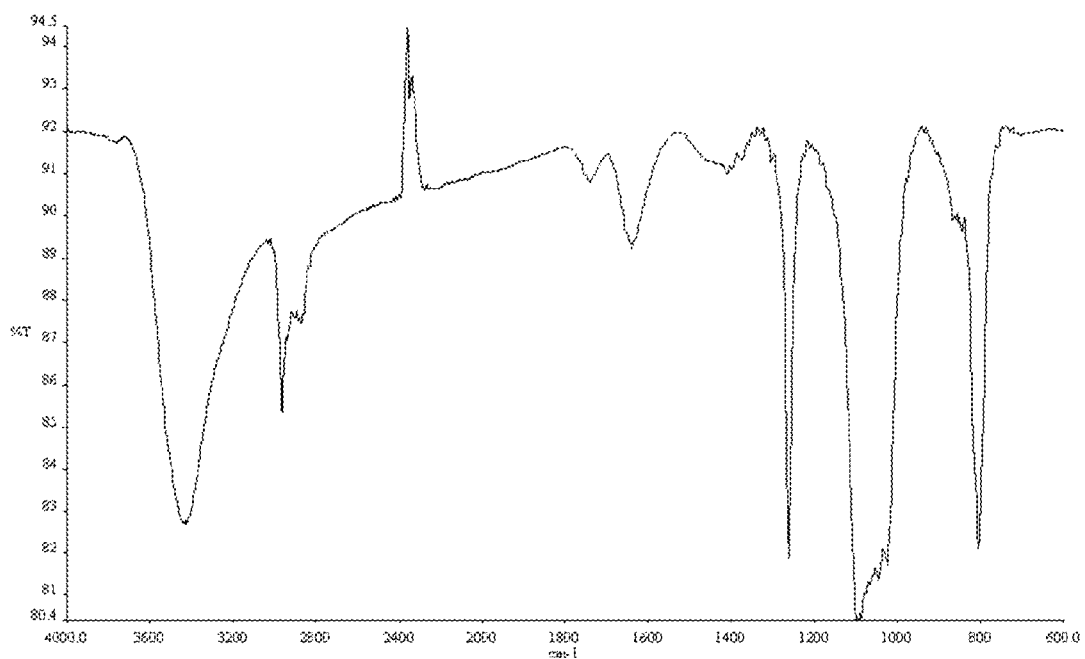
FIG. 38 depicts an IR spectrum of a maganese (II) sample described in Example 4, Series 1.

As can be seen from FIG. 38, a metal-hydride (Mn—H) stretch is observed at 1740 cm$^{-1}$. This Mn—H stretch grows in intensity upon treatment with hydrogen (FIG. 39) and decreases upon exposure to air for 2 and 5 minutes (FIGS. 40 and 41). Without wishing to be bound by theory, the inventor theorizes that the presence of the Mn—H stretch in FIG. 38 (i.e., the product formed by thermal precipitation but before hydrogenation) suggests a sigma-bond metathesis process has occurred in which a neopentyl ligand coordinated to the manganese atom is replaced by an n-hexyl ligand (from the petroleum ether) which then undergoes β-hydride elimination to form the Mn—H bond and 1-hexene. This likely occurs when the solvent used (petroleum ether) contains β-hydrogen atoms and is prone to C—H activation.

As seen in FIG. 39, treatment with hydrogen leads to an increase in the intensity of the Mn—H stretch at 1740 and a decrease in the intensity of the C—H stretch. As shown in FIGS. 40 and 41, exposure of the hydrogenated product to air results in formation of a hydroxyl stretch, presumably by absorption of water into the sample and/or by conversion of the Mn—H bond into an Mn—OH bond.

Series 2

Manganese (II) chloride was stirred with 2 equivalents of neopentyl magnesium chloride in diethylether and with 4 equivalents of dioxane, and the solution stirred for 24 hours at room temperature. The resulting product was isolated by filtration and washed with 100 mL of diethylether. The solvent removed in vacuo and the product was dried at 40° C. for 1 day. The resulting product was then dissolved in 40 mL of petroleum ether, filtered and washed with 100 mL of petroleum ether. Solvents were removed and the product was dried in vacuo for 4 hours. 0.8 g of the product was then dissolved in 100 mL of petroleum ether and placed in the PARR vessel for 2 days at 298K under 73 bar of $H_2$. 193 mg of solid was recovered and dried in vacuo for 2 hours to afford 173 mg of a solid (21.6% yield). The Infra-Red (IR) spectra for the sample of the resulting product is shown in FIG. 42.

Figure 43:
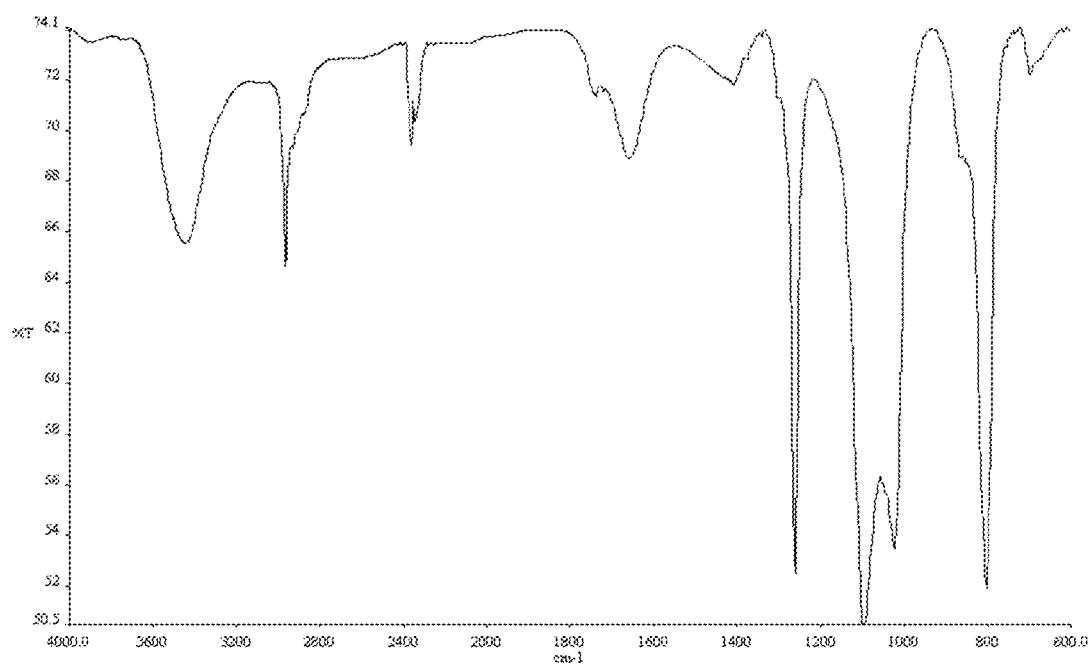
FIG. 43 depicts an IR spectrum of a maganese (II) sample described in Example 4, Series 2.
Figure 44:
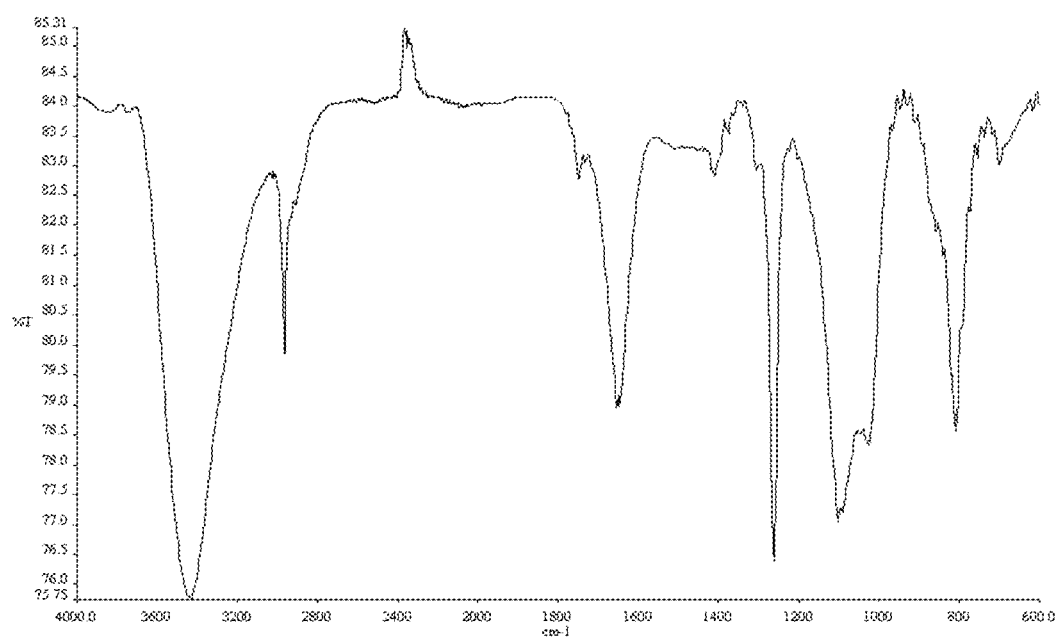
FIG. 44 depicts an IR spectrum of a maganese (II) sample described in Example 4, Series 2, upon exposure to air for 5 minutes.

The product was then hydrogenated at 150° C. and 85 bar $H_2$ for 4 hours. The temperature was reduced to 100° C. and the sample was dried in vacuo for 2 hours. The Infrared (IR) spectra for the resulting product is shown in FIG. 43. The Infrared (IR) spectra for this same sample taken 5 minutes after the initial spectrum of FIG. 43 is shown in FIG. 44.

Figure 42:
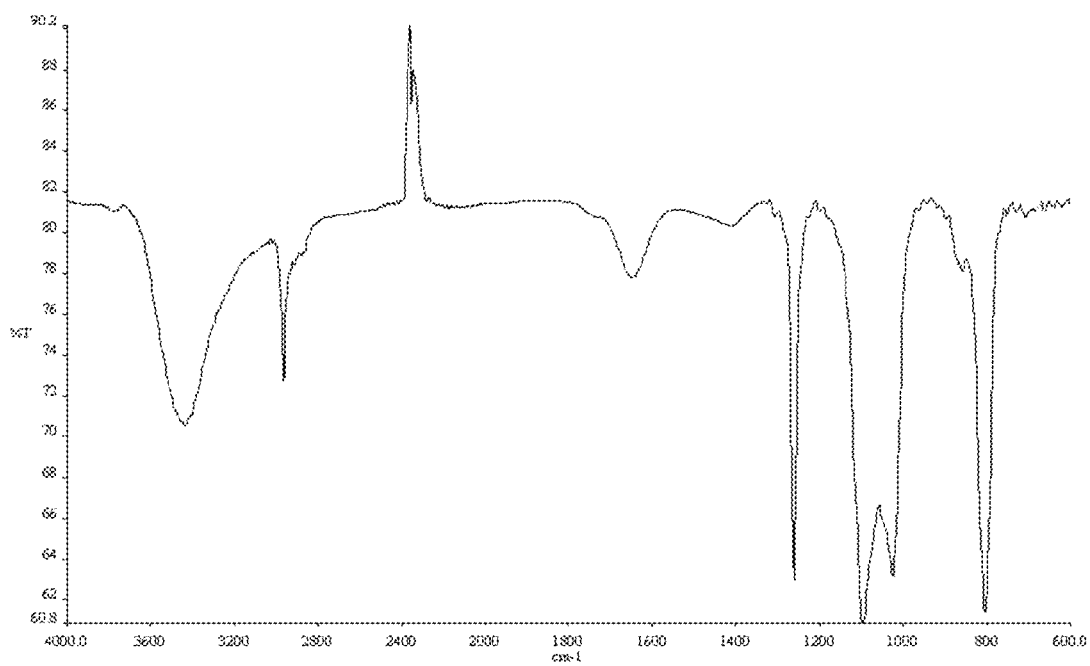
FIG. 42 depicts an IR spectrum of a maganese (II) sample described in Example 4, Series 2.

As can be seen from FIG. 42, a metal-hydride (Mn—H) stretch is observed at 1740 cm$^{-1}$, suggesting that the processes described in Series 1 (thermal precipitation of the manganese dialkyl without hydrogenation) and Series 2 (formation of the manganese dialkyl with hydrogenation) afford similar products.

Series 3

Manganese (II) chloride was stirred with 2 equivalents of neopentyl magnesium chloride in diethylether and with 4 equivalents of dioxane, and the solution stirred for 24 hours at room temperature. The resulting product was isolated by filtration and washed with 100 mL of diethylether. The solvent removed in vacuo and the product was dried at 40° C. for 1 day. The resulting product was then dissolved in 40 mL of petroleum ether, filtered and washed with 100 mL of petroleum ether. Solvents were removed and the product was dried in vacuo for 4 hours. 0.8 g of the product was then dissolved in 100 mL of cyclohexane and placed in the PARR vessel for 2 days at 100° C. (not under an atmosphere of hydrogen). 155 mg of solid was recovered and dried in vacuo for 2 hours to afford 148 mg of a solid (18.5% yield). The Infrared (IR) spectra for the sample of the resulting product is shown in FIG. 45.

Figure 46:
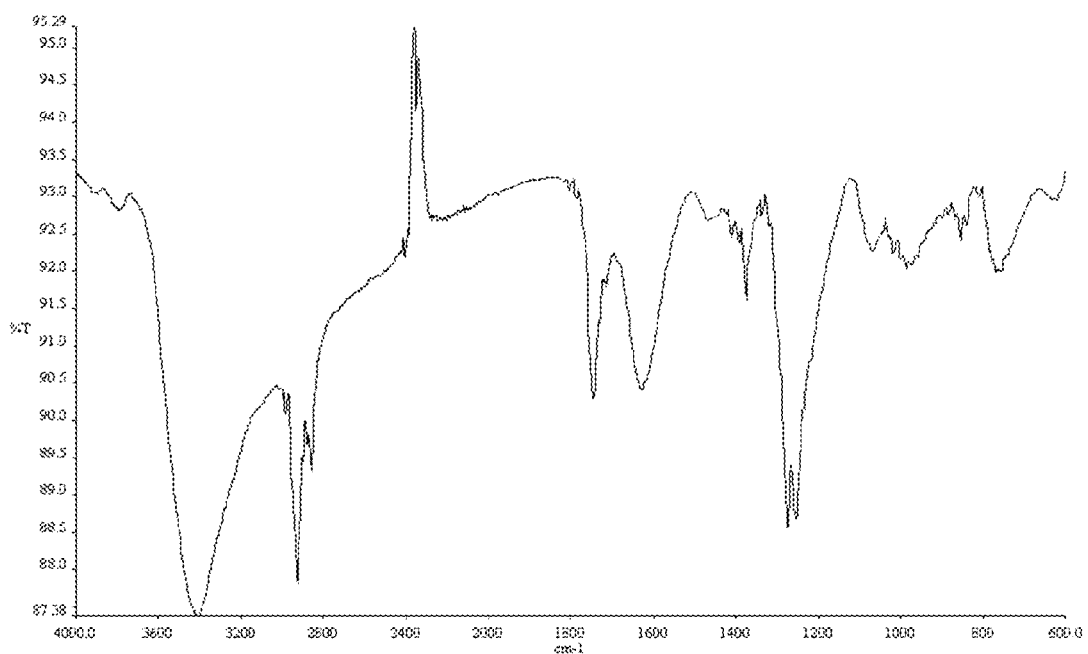
FIG. 46 depicts an IR spectrum of a maganese (II) sample described in Example 4, Series 3.
Figure 47:
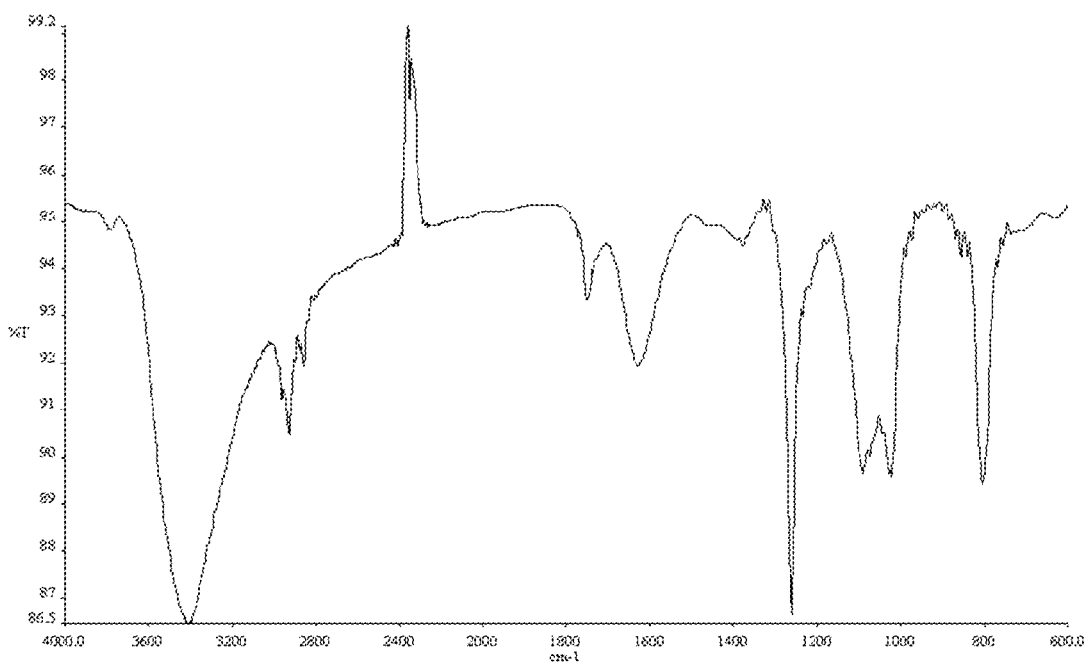
FIG. 47 depicts an IR spectrum of a maganese (II) sample described in Example 4, Series 3, upon exposure to air for 2 minutes.
Figure 48:
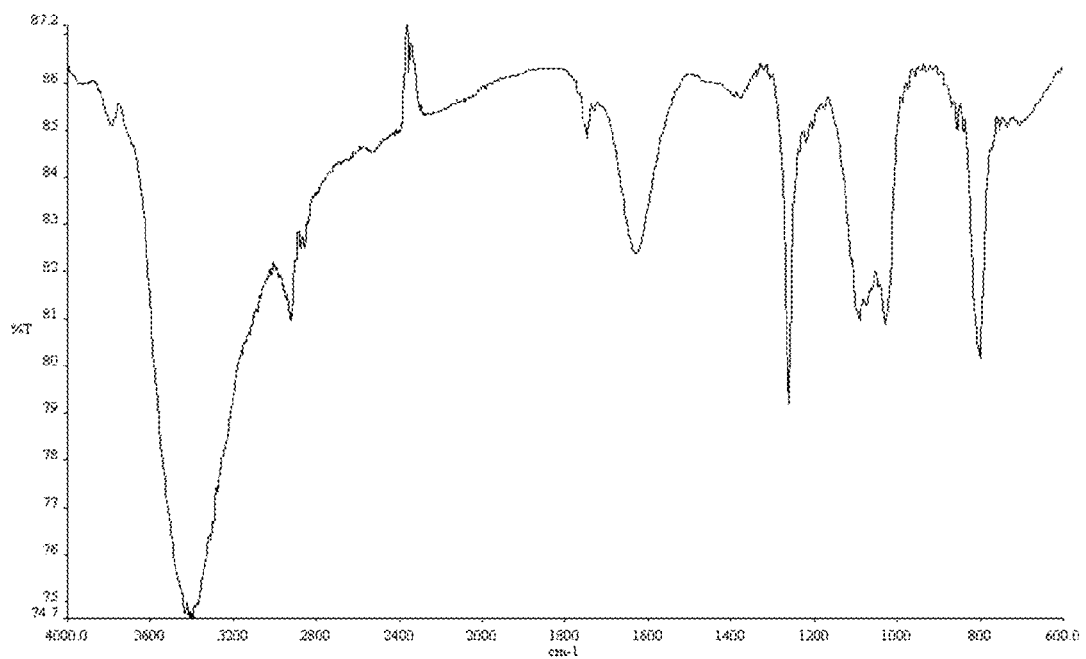
FIG. 48 depicts an IR spectrum of a maganese (II) sample described in Example 4, Series 3, upon exposure to air for 5 minutes.

The product was then hydrogenated at 150° C. and 85 bar $H_2$ for 4 hours. The temperature was reduced to 100° C. and the sample was dried in vacuo for 2 hours. The Infrared (IR) spectra of the resulting product is shown in FIG. 46. The Infrared (IR) spectra of this same sample taken 2 and 5 minutes after the initial spectrum of FIG. 46 are shown in FIGS. 47 and 48, respectively.

Figure 45:
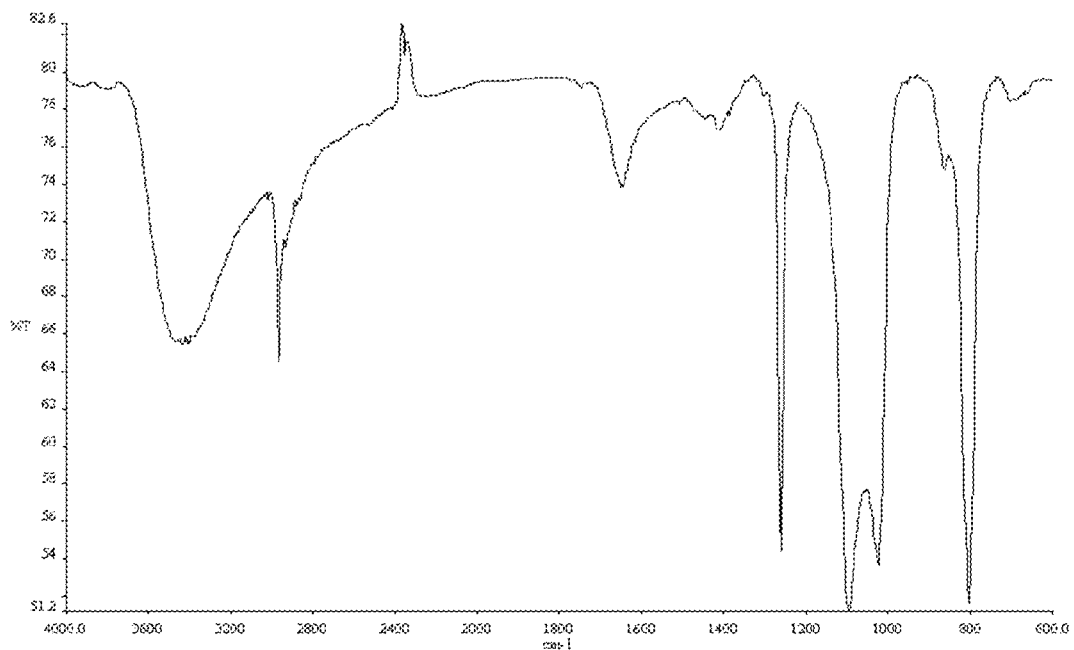
FIG. 45 depicts an IR spectrum of a maganese (II) sample described in Example 4, Series 3.

As can be seen from FIG. 45, thermal precipitation of the initial product from cyclohexane (a solvent inert to C—H activation) affords a product that does not exhibit a stretch at 1740 cm$^{-1}$, but exhibits C—H stretch, suggesting that in the absence of C—H activation of the solvent, a mechanisms involving C—H activation via α- or γ-hydride extraction to afford an organometallic polymer with bridging alkyl groups may occur. FIG. 46 shows that hydrogenation of the product leads to a decrease in the intensity of the C—H stretch and the appearance of the Mn—H stretch at 1740 cm$^{-1}$. As shown in FIGS. 47 and 48, exposure of the hydrogenated product to air results in a decrease in the intensity of the band at 1740 cm$^{-1}$.

Example 5

Direct Measurement of the Enthalpy of $H_2$ Adsorption by a Mn(II) Hydride Sample Bis(neopentyl) manganese(II) was prepared from neopentyl magnesium chloride using the dioxane method described in U.S. patent application Ser. No. 14/304,317, filed Jun. 13, 2014, (published as U.S. Publication No. 2014/0370406) which is hereby incorporated by reference in its entirety. This compound is extremely air sensitive and reacts spontaneously with even trace amounts of oxygen to form a green compound, the presence of which adversely affects downstream hydrogen storage performance.

(1.09 g, 5.53 mmol) was stirred in 100 mL of petroleum ether to afford a brown solution. The solution was placed in a PARR pressure vessel and stirred for two days at 100° C. under an inert atmosphere of argon. After cooling to room temperature, the reaction mixture was filtered to give a black precipitate and a colourless filtrate. The black precipitate was dried in vacuo at 100° C. for four hours to afford a black air moisture sensitive powder (105 mg) (Mn-Cal-100). This material was then reacted with hydrogen gas by placing the powder in a stainless steel sample holder. The sample holder was attached to the PCT-Pro instrument. The sample was charged with 20 bar $H_2$ and then the temperature of the sample holder was increased to 150° C. The sample was then charged with 85 bar $H_2$. After cooling the sample to 100° C., the sample was dried in vacuo for 2 hours before being allowed to cool to room temperature to afford a black air moisture sensitive powder (53.7 mg) (Mn-Cal-150-$H_2$).

Sample Characterization

Figure 49:
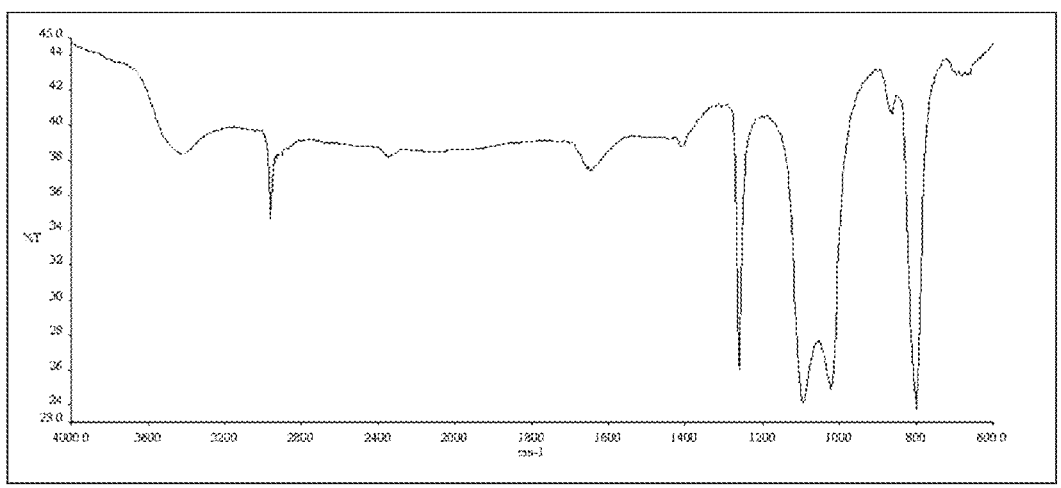
FIG. 49 depicts an IR spectrum of manganese hydride sample Mn-Cal-150-H$_2$.

The Infrared (IR) spectra for sample Mn-Cal-150-$H_2$ is shown below in FIG. 49. The stretch at 2964 $cm^{-1}$ corresponds to a C—H stretch due to hydrocarbon still remaining in the material. The stretches at 1021 $cm^{-1}$ and 1094 $cm^{-1}$ arise from C—O and may be due to diethyl ether being carried over to the final material from the synthesis of the precursor, Mn(neopentyl)$_2$. There is also a stretch at 1646 $cm^{-1}$ which is likely due to atmospheric water picked up by the KBr disc during rapid transfer of the disc from the glovebox to the IR spectrometer.

Hydrogen Adsorption Studies

Figure 50:
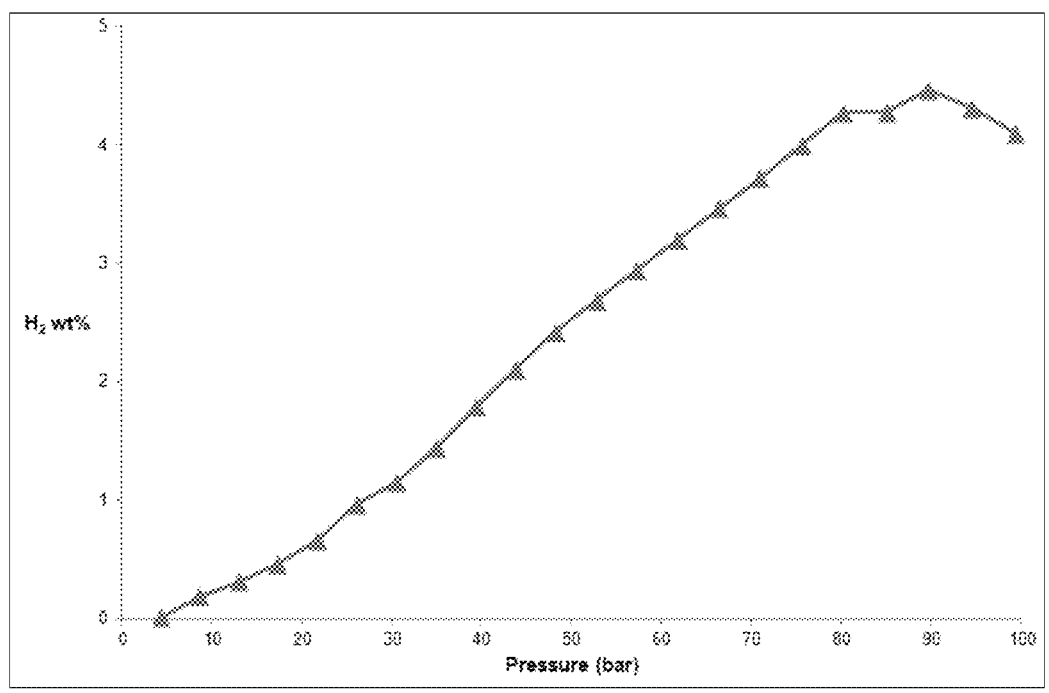
FIG. 50 depicts the hydrogen adsorption isotherm at 40° C. for manganese hydride sample Mn-Cal-150-H$_2$.

The gravimetric hydrogen adsorption-desorption isotherms for sample Mn-Cal-150-$H_2$ is shown in FIG. 50. The material reached a maximum gravimetric hydrogen adsorption of 4.47 wt % at 90 bar and 40° C. As shown in FIG. 50, the isotherm increases linearly with increasing pressure until 90 bar where the hydrogen adsorption reaches a plateau. It can be seen from FIG. 49 that there is still hydrocarbon remaining in the material. Unless oxidation has occurred, upon removal of the hydrocarbon by further hydrogenation, the hydrogen storage performance is expected to surpass 4.47 wt %.

Calorimetry

Figure 51:
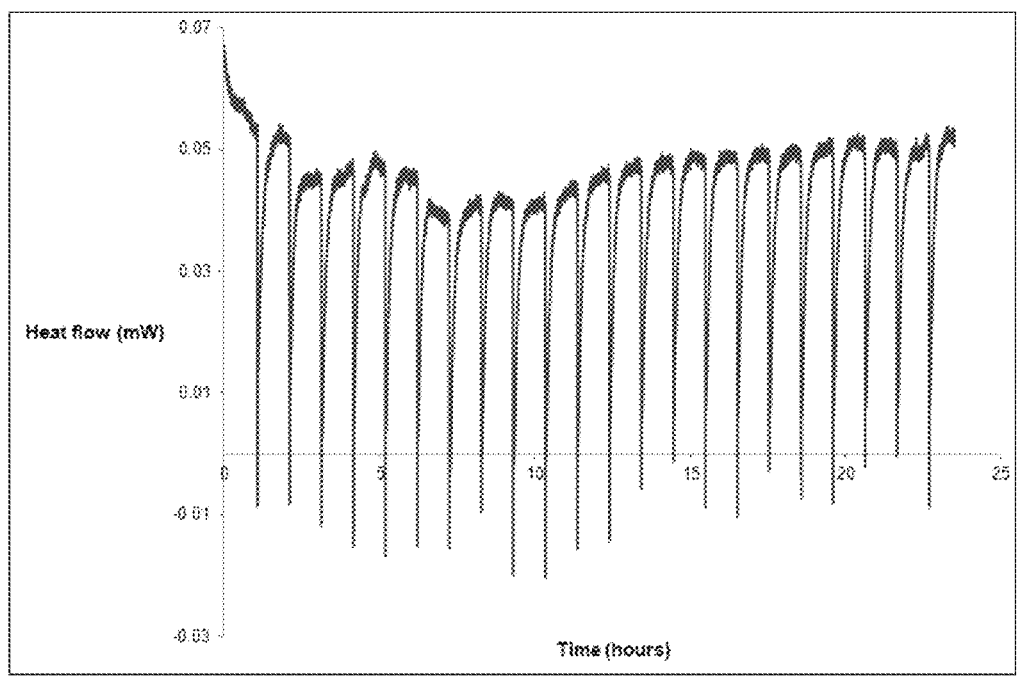
FIG. 51 depicts the calorimetric curves for manganese hydride sample Mn-Cal-150-H$_2$ during each addition of H$_2$ in a PCT hydrogen adsorption measurement

The calorimetric curves for sample Mn-Cal-150-$H_2$ are shown below in FIG. 51. To determine the heat flow in joules, each peak corresponding to the change in heat flow during a dose of hydrogen gas at a specific pressure was intergrated using the Calisto data processing software for the C80 calorimeter, supplied by Setaram. To obtain the total heat in joules at 100 bar, the heat in joules for each hydrogen dose was added together to give 0.513 J. To account for the effect of warming the gas when hydrogen is introduced to the C80 cells in the furnace, the heat at 100 bar from the blank measurement was subtracted (0.513 J–0.625 J=–0.112 J). The enthalpy of $H_2$ adsorption is then calculated by dividing the heat in joules by the number of moles of hydrogen adsorbed. In this example, the enthalpy of hydrogen adsorption for sample Mn-Cal-150-$H_2$ is –0.11 kJ $mol^{-1}$ $H_2$ The enthalpy of hydrogen adsorption for a material that stores hydrogen by the Kubas interaction is typically –20-40 kJ $mol^{-1}$ $H_2$. As the value obtained by direct measurement for sample Mn-Cal-150-$H_2$ is outside this range and is close to zero, a second process may be involved which could be due to twisting of the material to create new Kubas hydrogen binding sites.

Example 6

Synthesis of Cr(II) Hydride Sample

Preparation of $CrCl_2(THF)_{1.13}$

Chromium(II) chloride (5.353 g, 43.55 mmol) was stirred 80 mL of THF to give a green suspension. The suspension was then stirred under reflux for 72 hours. The excess THF was then removed in vacuo and the pale green solid thus obtained was dried in vacuo at 50° C. for 3 hours to afford a pale green powder (8.8914 g).

Preparation of Bis[(trimethylsilyl)methyl] Chromium II

To a stirred suspension of $CrCl_2(THF)_{1.13}$ (5.1095 g, 25 mmol) in 200 mL of 40-60° C. petroleum ether was added a solution of (trimethylsilyl)methyllithium (50 mmol, 50 mL of a 1.0 M solution in pentane). The colour of the slurry immediately changed to dark brown. The mixture was stirred at room temperature for 12 hours then filtered, and the residue was washed petroleum ether (3×20 mL). The dark brown filtrate was concentrated and dried at room temperature in vacuo for 48 hours to afford a dark brown solid (5 g, 89% yield). See also Schulzke et al., *Organometallics*, 21, 3810, 2002.

Preparation of Chromium(II) Hydride Sample

Bis[(trimethylsilyl)methyl]chromium(II) (5 g, 22.1 mmol) was stirred in 250 mL of 30-60° petroleum ether to give a dark brown solution. The solution was placed in the PARR pressure vessel and the vessel was pressurized at 10 bar $H_2$ for 72 hours. The pressure was then increased to 70 bar for 48 hours. The vessel was then heated at 100° C. under an atmosphere of argon for 72 hours, followed by the reaction being heated at 100° C. and 80 bar $H_2$ for 72 hours. The reaction was filtered to give a black precipitate and a black filtrate. The precipitate was rinsed with petroleum ether (3×10 mL). The precipitate was then dried at 100° C. in vacuo for 4 hours to give a black air moisture sensitive powder Cr(II)-100 (0.3155 g).

Sample Characterization

Figure 52:
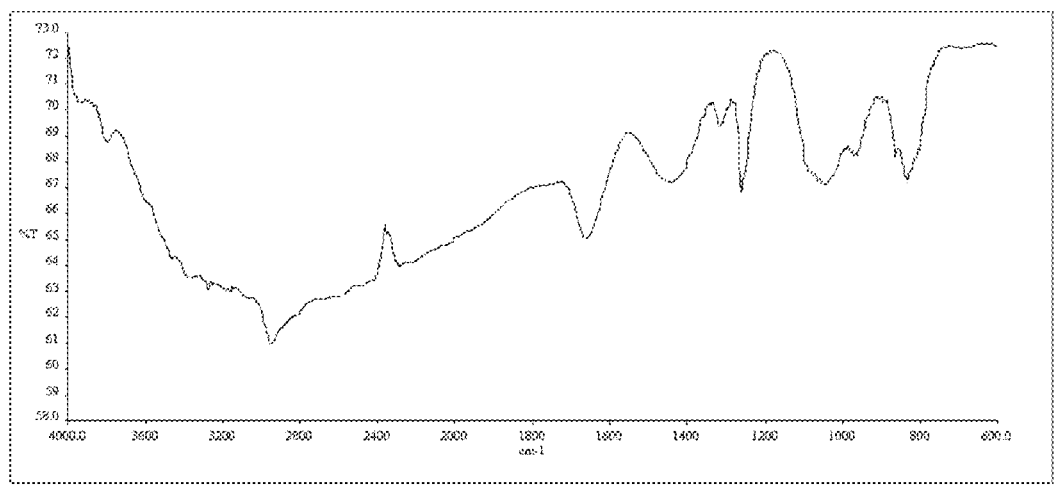
FIG. 52 depicts an IR spectrum of chromium hydride sample Cr(II)-100.

The Infrared (IR) spectra for sample Cr(II)-100 is shown in FIG. 52. The stretch at 2950 $cm^{-1}$ can be attributed to a C—H stretch arising from trimethylsilyl ligands that have not been removed from the material. The stretch at 1261 $cm^{-1}$ is from C—Si present in the trimethylsilyl group. There is a broad C—O stretch that may be due to residual THF present in the material from the precursor. There is a medium-intensity absorbance at 1664 $cm^{-1}$, which is close to the Cr—H stretches observed for matrix isolated $CrH_2$. In KBr however, water displays stretches at 3300 and 1647 $cm^{-1}$. Therefore it is possible that the stretch at 1664 $cm^{-1}$ arises from atmospheric water picked up by the KBr disc and the Cr—H stretch is obscured by an O—H stretch.

Figure 53:
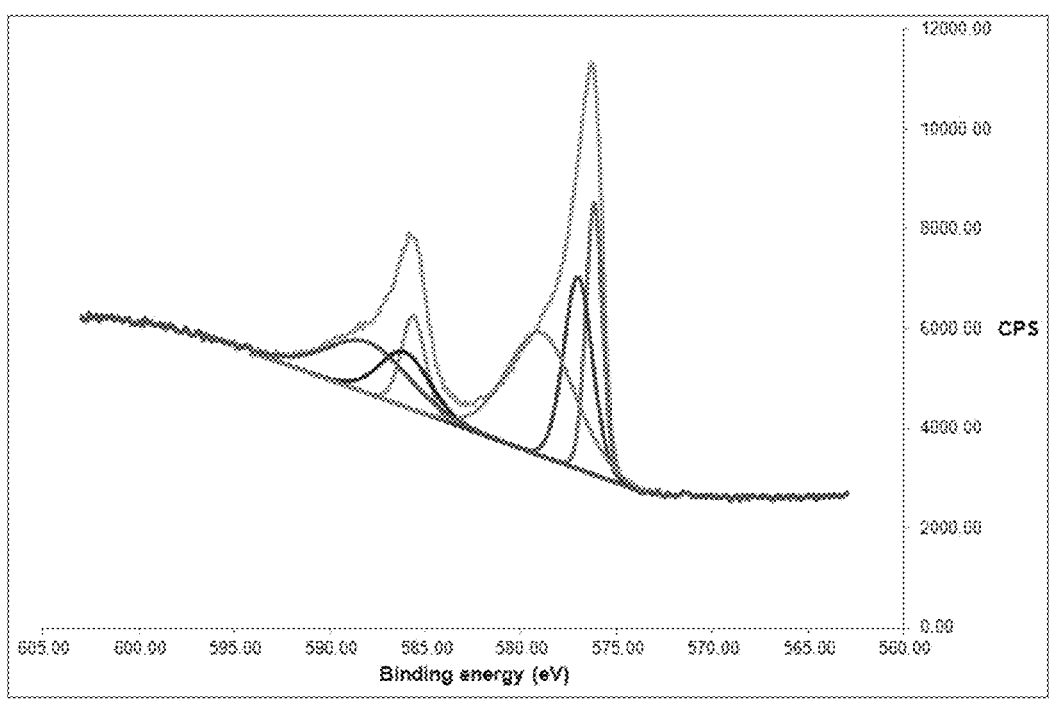
FIG. 53 depicts the peak fitting of chromium $2p_{1/2}$ and $2p_{3/2}$ region in the X-ray photoelecton spectrum (XPS) of chromium hydride sample Cr(II)-100.

X-ray photoelectron spectroscopy was carried out on sample Cr(II)-100 to determine the oxidation state of chromium present in the material. The Cr 2p region is shown in FIG. 53. Peak fitting shows that there are three different oxidation states present contributing to the Cr 2p 3/2 emission. The major emission at 576.4 eV can be attributed to Cr(II) as it is similar to the emission at 575.4 eV for bis(benzene)chromium (see Pignataro et al., *Chemical Physics Letters*, 20, 35, 1973). The emission at 577.3 eV can be attributed to Cr(III) as it is close to the emission at 577.3 eV for $CrCl_3$. The less intense emission at 579.4 eV can be attributed to Cr(IV) as it is in the same region as the emission at 579.7 eV for Cr(IV) in $Cr_2(CrO_4)_3$ (see Volkov et al., *Zhurnal Neorganicheskoi Khimii*, 39, 877, 1994).

Hydrogen Adsorption Studies

Figure 54:
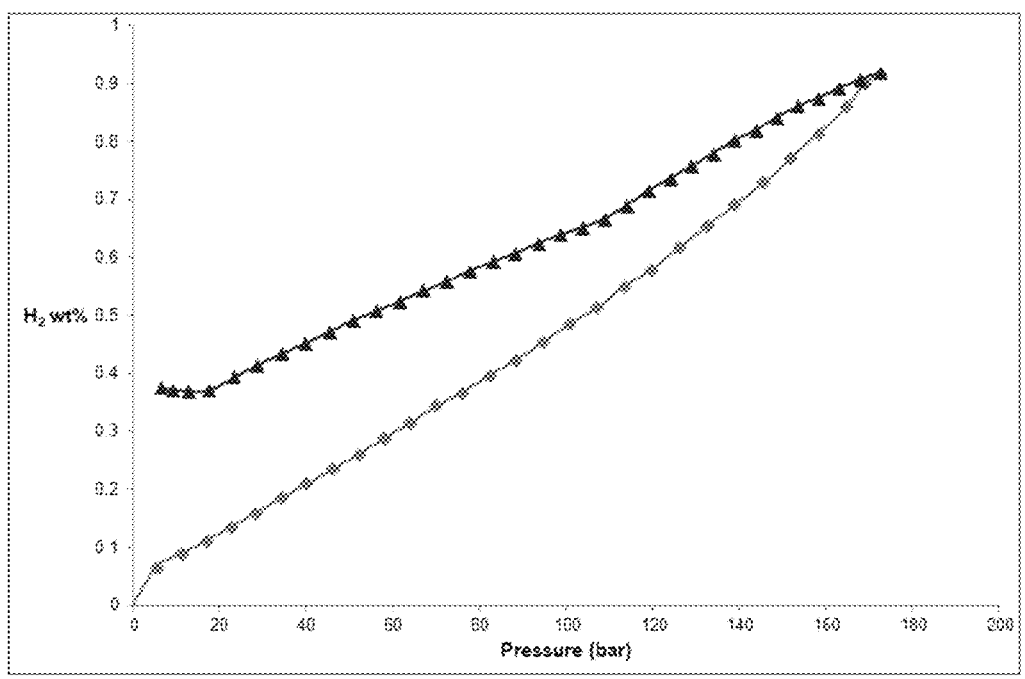
FIG. 54 depicts a hydrogen adsorption-desorption isotherm for chromium hydride sample Cr(II)-100.

The gravimetric hydrogen adsorption (bottom trace)-desorption (top trace) isotherms for sample Cr(II)-100 is shown in FIG. 54. The isotherm increases linearly with increasing pressure without saturation at 170 bar. The material has a gravimetric hydrogen storage capacity of 0.92 wt % at 170 bar and 298 K. There is some hysteresis between the adsorption and desorption isotherms. The performance of this material is lower than material Cr-100, which reached 2.44 wt % at 150 bar and 298 K. The difference between the two materials is likely that the chromium alkyl precursors were made using different synthetic procedures. In this example, the route reported by Gambarotta (see Gambarotta et al., *Organometallics*, 221, 3810, 2002) starting with $CrCl_2(THF)_{1.13}$ and two equivalents of the alkyl lithium was followed. This produced the dark brown Cr(II) alkyl. Hydrogenation of the Cr(II) alkyl gave a material with poor hydrogen storage properties compared to the material that was made from decomposition of the dark purple Cr(IV) alkyl tetrameric complex.

Thus, starting with the dark purple Cr(IV) alkyl (as in Example 1) gave a hydrogen storage material Cr-100 (where decomposition of the Cr(IV) alkyl caused a reduction to give a Cr(III) species). Starting out with the Cr(II) alkyl precursor (as in Example 6) gave a material of mixed oxidation state with there being Cr(II), Cr(III) and (Cr(IV) present. The mixed valent Cr material (Cr(II)-100) has a lower hydrogen storage capacity than sample Cr-100.

Example 7

Alternate Synthesis of Manganese (II) Hydride Sample 2.96 g (23.5 mmol) of $MnCl_2$ (previously dried over thionyl chloride) was ground in a pestle and mortar to a fine powder and stirred in 50 mL of diethyl ether. Neopentyl magnesium chloride (47 mmol in 20 mL diethyl ether) was added and the reaction mixture was stirred for 20 minutes. 8.01 ml, (94 mmol) of dioxane was then added dropwise over 5 hours and the colour of the reaction changed from pink to grey/green as it thickened. 20 mL of additional diethyl ether was then added and the reaction was stirred for 24 hours at room temperature. The reaction was then filtered to afford a brown/green filtrate and a white precipitate. The precipitate was washed with 3×30 mL of diethyl ether (the filtrate changed from dark brown to a pale orange). After filtration, the solvent was removed in vacuo to afford a dark brown solid, which was subsequently dried at 45° C. for 2 hours in vacuo to give a pale brown solid 3.7 g (81%). The solid was then dissolved in 40 mL of petroleum ether, stirred for 20 minutes and filtered to give a white precipitate and a brown filtrate. The solvents were removed in vacuo to afford a brown solid 2.925 g (62%). Thermal precipitation of this solid out of petroleum ether for 48 hours at 100° C. gave 900 mg of a fine black solid.

Figure 55:
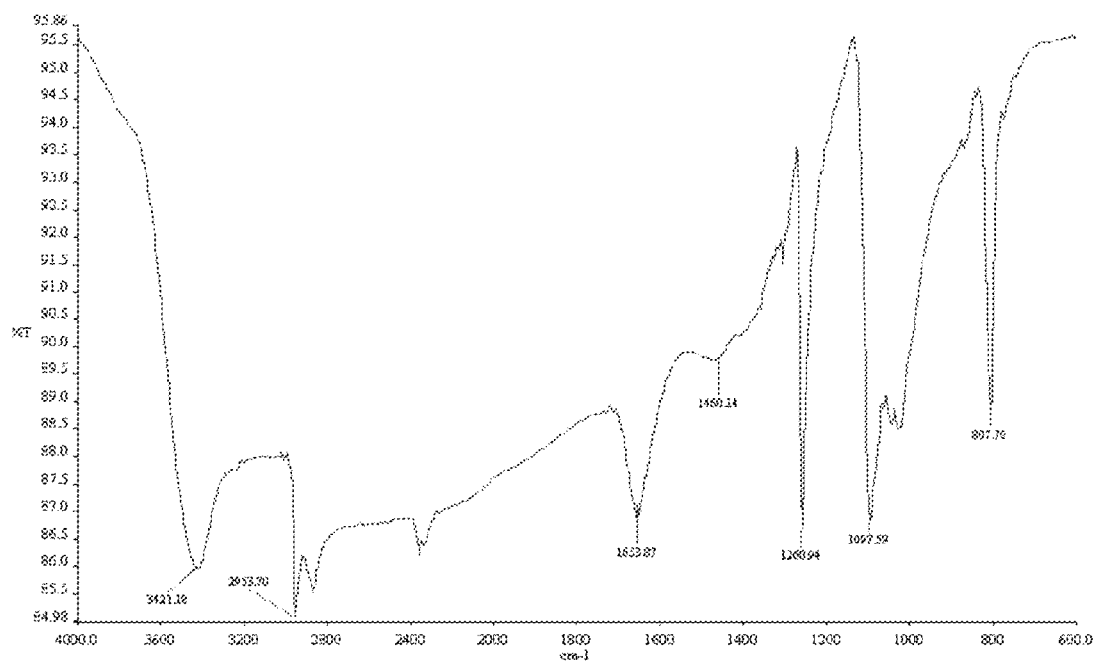
FIG. 55 depicts an IR spectrum of chromium hydride sample Cr(II)-100.

The Infrared (IR) spectra for this manganese hydride (II) sample is shown in FIG. 55.

Example 8

Alternate Synthesis of Vanadium (IV) Hydride Sample

This example describes an improved process for the preparation of a V(IV) alkyl precursor (tetramesitylvanadium (IV)) that utilizes a Grignard reagent (mesitylMgBr), thereby avoiding the use of expensive lithium reagents.
Synthesis
Preparation of TetramesitylVanadium (IV)

Figure 56:
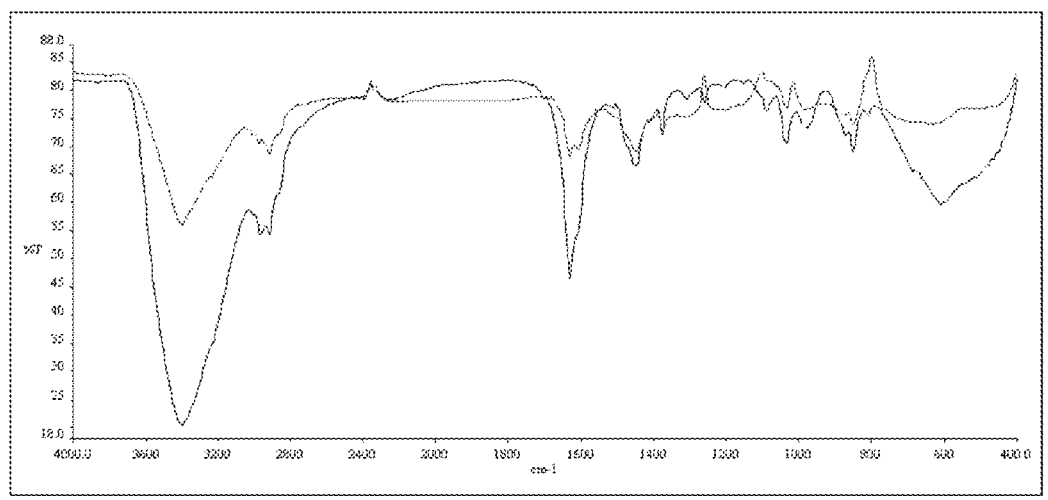
FIG. 56 depicts the IR spectra for samples V(Mes)-100 and V(Mes)-100H$_2$.
Figure 57:
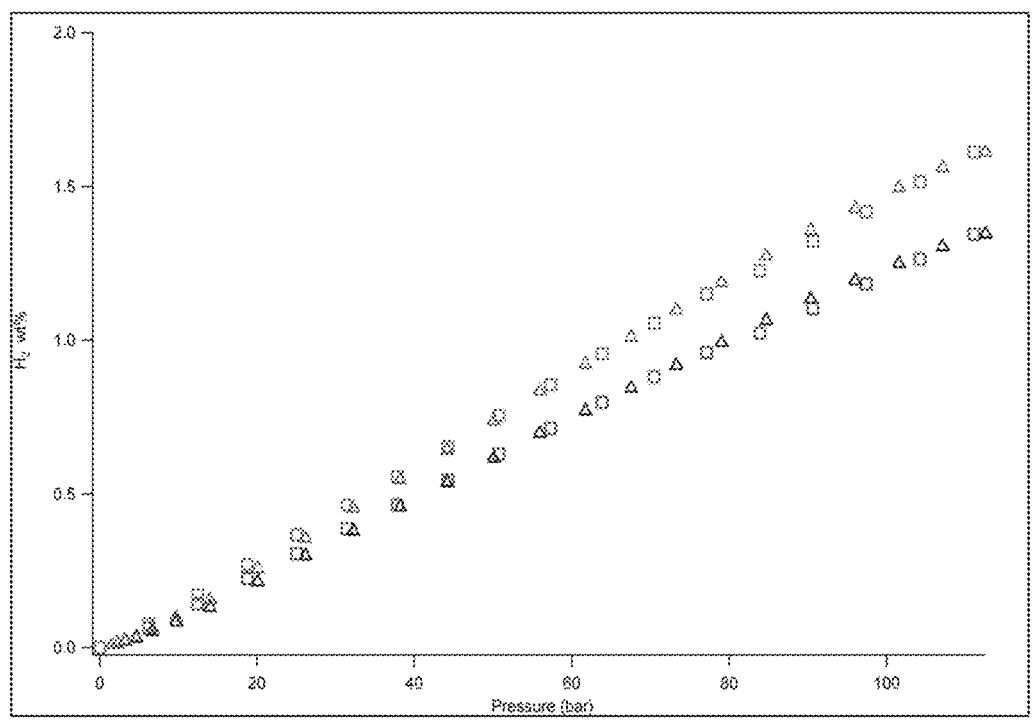
FIG. 57 depicts hydrogen adsorption-desorption isotherms for samples V(Mes)-100 and V(Mes)-100H$_2$.

Vanadium tetrachloride (2 g, 10.38 mmol) was stirred in diethyl ether (40 mL) at 25° C. to afford a dark red solution. Mesitylmagnesium bromide (41.52 mL of a 1.0 M solution in diethyl ether) was then added dropwise. The reaction mixture effervesced upon addition of the Grignard reagent and turned from dark red to black. After stirring for 24 hours, the reaction mixture was filtered to give a grey precipitate (2.1 g) and a black filtrate. The filtrate was concentrated in vacuo to give a black oil. The oil was extracted with petroleum ether (50 mL) to give a brown precipitate and a dark red/purple filtrate. The filtrate was concentrated in vacuo and dried to afford a dark red/purple oil (4.6 g, 84%).
Thermal Precipitation 2.3 g (4.35 mmol) of tetramesityl vanadium(IV) was stirred in 50 mL of petroleum ether to give a dark brown solution. The solution was then placed in a stainless steel PARR pressure vessel under an atmosphere of argon. The vessel was stirred at 100° C. for 48 hours. After cooling to room temperature, the reaction mixture was filtered to give a dark brown filtrate and a black precipitate. The black precipitate was dried for 4 hours in vacuo at 100° C. to afford a dark brown air sensitive solid V(Mes)-100 (360 mg).
Preparation of Vanadium(IV) Hydride Sample The brown air sensitive solid V(Mes)-100 was then hydrogenated at 100 bar $H_2$ and 25° C. in the absence of solvent to afford vanadium hydride sample V(Mes)-$100H_2$.
Sample Characterization The Infra-Red (IR) spectra for samples V(Mes)-100 (bottom trace) and V(Mes)-$100H_2$ (top trace) are shown in FIG. 56. For sample V(mes)-100 C—H stretches are observed at 2917 and 2968 $cm^{-1}$. The intensity of the C—H stretches decreases slightly after room temperature hydrogenation at 110 bar (sample V(Mes)-$100H_2$) as the hydrocarbon ligands are replaced by hydrides during hydrogenolysis. Typically transition metal-hydride bonds are observed in the region of 1900±300 $cm^{-1}$ region however they can be weak in intensity (Kaesz et al., *Chemical Reviews*, 72, 231-281, 1972). A stretch in this region at 1630 $cm^{-1}$ and a shoulder at 1625 $cm^{-1}$ are observed for sample V(Mes)-$110H_2$. In KBr, water displays bands at 3300 and 1647 $cm^{-1}$. The shoulder in the spectrum of V(Mes)-$110H_2$ at 1625 $cm^{-1}$ which could be attributed to a V—H stretch is possibly obscured slightly by an O—H stretch at 1630 $cm^{-1}$ from water absorbed by the KBr disc during the rapid transfer step from the glove box to IR apparatus.
Hydrogen Adsorption-Desorption Studies The gravimetric hydrogen adsorption-desorption isotherms for samples V(Mes)-100 (bottom trace, adsorption (square), desorption (triangle)) and V(Mes)-$100H_2$ (top trace, adsorption (square), desorption (triangle)) are shown in FIG. 57

The isotherms increase linearly with increasing pressure without saturation at the pressures tested. For sample V(Mes)-100, the material reached 1.3 wt % at 110 bar. There is no hysteresis in the isotherm indicating that there is no significant kinetic barrier to overcome to fully desorb the hydrogen. After room temperature hydrogenation, sample V(Mes)-100 lost significant weight and hydrogen storage performance increased. Sample V(Mes)-$110H_2$ reached a maximum of 1.7 wt % at 110 bar. To ensure accuracy, carbon AX-21 was used as a standard.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

Patents, patent applications, publications, product descriptions, and protocols are cited throughout this application, the disclosures of which are incorporated herein by reference in their entireties for all purposes.

What is claimed is:

1. A process for preparing a metal hydride comprising
    (i) heating an alkyl or aryl transition metal compound, or a combination thereof, in a solvent in the absence of hydrogen to form a precipitate;

(ii) optionally isolating the precipitate;
(iii) hydrogenating the precipitate; and
(iv) optionally isolating the hydrogenated precipitate.

2. The process according to claim 1, wherein the alkyl or aryl transition metal compound has the formula $M^1R$, $M^1R_2$, $M^1R_3$ or $M^1R_4$, or a combination thereof, wherein:
  $M^1$ is a transition metal selected from titanium, vanadium, chromium, manganese, iron, cobalt, nickel and copper, and combinations thereof; and
  each R group is, independently, selected from alkyl, silylated alkyl, alkenyl, arylalkyl, heteroaryl and aryl.

3. The process according to claim 2, wherein each R group does not contain a β-hydrogen substituent.

4. The process according to claim 1, wherein the product of step (i) contains greater than about 10% by weight of residual hydrocarbon.

5. The process according to any one of claims 1, wherein step (i) is conducted at a temperature of from about 50° C. to about 250° C., from about 50° C. to about 200° C., from about 75° C. to about 150° C., from about 80° C. to about 120° C., from about 90° C. to about 110° C. or from about 95° C. to about 105° C., optionally for a period time between about 12 hours and about 72 hours, between about 24 hours and about 36 hours, or for about 24 hours.

6. The process according to claim 1, wherein step (i) is conducted in a solvent selected from pentane, hexane, heptane, octane, petroleum ether, toluene and combinations thereof.

7. The process according to of claims 1, wherein the hydrogenation in step (iii) is conducted at a hydrogen pressure of between about 1 bar and about 200 bar, between about 25 bar and about 150 bar, between about 50 bar and about 125 bar, between about 50 bar and about 100 bar, or between about 60 bar to about 80 bar, optionally, at a temperature of from about 10° C. to about 200° C., from about 10° C. to about 100° C., from about 15° C. to about 50° C., from about 20° C. to about 40° C., or from about 20° C. to about 30° C., further optionally, step (iii) is conducted for a period of time between about 12 hours and about 72 hours, between about 24 hours and about 60 hours, or for about 48 hours.

8. A metal hydride of formula (I):

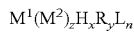  (I)

wherein
  $M^1$ is a first metal selected from titanium, vanadium, chromium, iron, cobalt, nickel, copper, and mixtures thereof;
  $M^2$ is one or more additional metals, which have a total content of z;
  R, if present, is an organic group;
  L is a Lewis base;
  n is 0 to about 1;
  y is 0 to about 0.5, and
  z is 0 to about 0.5;
wherein
  when $M^1$ is Ti or V, x is about 4.6 to about 13;
  when $M^1$ is Cr, x is about 4.6 to about 12;
  when $M^1$ is Fe, x is about 4.6 to about 10
  when $M^1$ is Ni or Co, x is about 4.6 to about 8;
  when $M^1$ is Cu, x is about 4.6 to about 6;
wherein the metal hydride is prepared by a process according to claim 1.

9. A metal hydride of the formula (I):

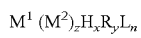  (I)

wherein
  $M^1$ is a first metal selected from titanium, vanadium, chromium, iron, cobalt, nickel, copper, and mixtures thereof;
  $M^2$ is one or more additional metals which have a total content of z;
  R, if present, is an organic group;
  L is a Lewis base;
  n is 0 to about 1;
  y is 0 to about 0.5, and
  z is 0 to about 0.5;
wherein
  when $M^1$ is Ti or V, x is about 4.6 to about 13;
  when $M^1$ is Cr, x is about 4.6 to about 12;
  when $M^1$ is Fe, x is about 4.6 to about 10
  when $M^1$ is Ni or Co, x is about 4.6 to about 8;
  when $M^1$ is Cu, x is about 4.6 to about 6.

10. The metal hydride according to claim 9, wherein x is about 8.6 to about 13.

11. The metal hydride according to claim 9, wherein
  (a) when $M^1$ is Ti, x is about 7.5 to about 13;
  (b) when $M^1$ is V, x is about 7.5 to about 13;
  (c) when $M^1$ is Cr, x is about 6.5 to about 12;
  (d) when $M^1$ is Fe, x is about 6.5 to about 10;
  (e) when $M^1$ is Co, x is about 6.5 to about 8; or
  (f) when $M^1$ is Ni, x is about 6.5 to about 8.

12. A metal hydride of the formula (II):

$$M^1(M^2)_z H_x R_y L_n (H_2)_a \quad (II)$$

wherein
  $M^1$ is a first metal selected from titanium, vanadium, chromium, iron, cobalt, nickel, copper, and, optionally, mixtures thereof;
  $M^2$ is one or more additional metals, which have a total content of z;
  R, if present, is an organic group;
  L is a Lewis base;
  n is 0 to about 1;
  x is about 0.5 to about 4.5;
  a is greater than 1;
  y is 0 to about 0.5, and
  z is 0 to about 1.

13. The metal hydride according to claim 12, wherein a is about 3, about 4 or about 5.

14. The metal hydride according to claim 12, wherein
  (a) $M^1$ is Ti, x is about 3 and a is about 3 to about 5;
  (b) $M^1$ is V, x is about 3 and a is about 3 to about 5;
  (c) $M^1$ is Cr, x is about 2 and a is about 3 to about 5;
  (d) $M^1$ is Fe, x is about 2 and a is about 3 to about 5;
  (e) $M^1$ is Co, x is about 2 and a is about 3; or
  (f) $M^1$ is Ni, x is about 2 and a is about 3.

15. The metal hydride according to claim 9, wherein y is less than about 0.4.

16. The metal hydride according to claim 9, wherein y is 0 to about 0.4.

17. The metal hydride according to claim 9, wherein R, if present, is, independently selected from alkyl, silylated alkyl, alkenyl, arylalkyl, heteroaryl and aryl.

18. The metal hydride according to claim 9, wherein the metal hydride is free or substantially free of metal ions other than titanium, vanadium, chromium, iron, cobalt, nickel, and copper and, optionally, the metal hydride is free or substantially free of organic residue.

19. The metal hydride according to claim 9, wherein the metal hydride has a pore diameter of between about 0.5 and about 50 nm.

20. The metal hydride according to claim 9, wherein hydrogenation and/or dehydrogenation of the metal hydride is thermodynamically neutral.

21. A composition comprising one or more metal hydrides according to claim 9.

22. A metal hydride storage material comprising one or metal hydrides according to claim 8.

23. A method of storing hydrogen comprising:
(i) providing a metal hydride according to claim 9;
(ii) adding hydrogen to the metal hydride; and
(iii) allowing the hydrogen to coordinate to the metal hydride;
optionally wherein the hydrogen is stored in a storage system, such that the method comprises
(i) providing a metal hydride according to claim 9 in the storage system;
(ii) adding hydrogen to the metal hydride in the storage system; and
(iii) allowing the hydrogen to coordinate to the metal hydride in the storage system.

24. The method according to claim 23, further comprising releasing the hydrogen from the metal hydride.

25. The method according to claim 24, wherein the hydrogen is released from the metal hydride by reducing the pressure of the hydrogen in the storage system, increasing the temperature of the storage system, or a combination thereof.

26. The method according to claim 23, wherein adsorption of hydrogen to the metal hydride and/or desorption of hydrogen from the metal hydride is thermodynamically neutral.

27. A hydrogen storage system comprising a storage system and a metal hydride according to claim 9 within the storage system.

28. A battery or fuel cell comprising a metal hydride according to claim 9.

29. A storage system for a gas selected from hydrogen, methane and compressed natural gas comprising a storage system and a metal hydride according to claim 9 within the storage system.

30. A storage system for producing electricity using a fuel-cell or heat using an oxidant, comprising a storage system and a metal hydride according to claim 9 within the storage system.

31. The process according to claim 1, wherein step (i) is conducted in an aromatic solvent.

32. The process according to claim 31, wherein the aromatic solvent is toluene.

33. The process according to claim 1, wherein the alkyl or aryl transition metal compound has the formula $M^1R_2$.

34. The process according to claim 33, wherein $M^1$ is manganese and R is silylated alkyl.

35. The process according to claim 34, wherein R is trimethylsilylmethyl.

36. The process according to claim 35, wherein step (i) is conducted in toluene.

37. The metal hydride according to claim 9, wherein
(a) when $M^1$ is Ti, x is about 8 to about 13, about 9 to about 13, about 10 to about 13, about 11 to about 13, about 12 to about 13, about 7.5 to about 8.5, about 8.5 to about 9.5, about 9.5 to about 10.5, about 10.5 to about 11.5, about 11.5 to about 12.5 or about 12.5 to about 13;
(b) when $M^1$ is V, x is about 8 to about 13, about 9 to about 13, about 10 to about 13, about 11 to about 13, about 12 to about 13, about 7.5 to about 8.5, about 8.5 to about 9.5, about 9.5 to about 10.5, about 10.5 to about 11.5, about 11.5 to about 12.5 or about 12.5 to about 13;
(c) when $M^1$ is Cr, x is about 7 to about 12, about 8 to about 12, about 9 to about 12, about 10 to about 12 or about 11 to about 12, about 6.5 to about 7.5, about 7.5 to about 8.5, about 8.5 to about 9.5, about 9.5 to about 10.5, about 10.5 to about 11.5 or about 11.5 to about 12;
(d) when $M^1$ is Fe, x is about 7 to about 10, about 8 to about 10, about 9 to about 10, about 6.5 to about 7.5, about 7.5 to about 8.5, about 8.5 to about 9.5 or about 9.5 to about 10;
(e) when $M^1$ is Co, x is about 7 to about 8, about 6.5 to about 7.5 or about 7.5 to about 8; or
(f) when $M^1$ is Ni, x is about 7 to about 8, about 6.5 to about 7.5 or about 7.5 to about 8.

38. The metal hydride according to claim 9, wherein y is less than about 0.3, less than about 0.2, less than about 0.1 or less than about 0.05.

39. The metal hydride according to claim 9, wherein y is 0 to about 0.3, 0 to about 0.25, 0 to about 0.2, 0 to about 0.1, or 0 to about 0.05.

40. The metal hydride according to claim 9, wherein x is about 8.6 to about 12, about 8.6 to about 11 or about 8.6 to about 10.

41. The metal hydride according to claim 9, wherein $M^2$ is a period 4, 5, 6, 7, 8, 9, 10, 11 or 12 transition metal, or a lanthanide.

42. The metal hydride according to claim 9, wherein $M^2$ is selected from the group consisting of niobium, molybdenum, technetium, ruthenium, rhodium, palladium, silver, iron, zirconium, zinc, gallium, cadmium, hafnium, tantalum, tungsten, rhenium, osmium, iridium, platinum, gold, mercury, and any combination thereof.

43. The metal hydride according to claim 9, wherein the first metal $M^1$ is in more than one oxidation state.

44. The metal hydride according to claim 12, wherein the first metal $M^1$ is in more than one oxidation state.

45. A metal hydride of the formula (I):

$$M^1(M^2)_zH_xR_yL_n \qquad (I)$$

wherein
$M^1$ is a first metal selected from titanium, vanadium, chromium, iron, cobalt, nickel, copper, and mixtures thereof;
$M^2$ is one or more additional metals other than manganese, which have a total content of z;
R, if present, is an organic group;
L is a Lewis base;
n is 0 to about 1;
y is 0 to about 0.5, and
z is 0 to about 1;
wherein
when $M^1$ is Ti or V, x is about 4.6 to about 13;
when $M^1$ is Cr, x is about 4.6 to about 12;
when $M^1$ is Fe, x is about 4.6 to about 10
when $M^1$ is Ni or Co, x is about 4.6 to about 8;
when $M^1$ is Cu, x is about 4.6 to about 6.

46. A metal hydride of the formula (III):

$$M^1(M^2)_zH_xR_yL_n \qquad (III)$$

wherein
$M^1$ is a first metal selected from titanium, vanadium, chromium, iron, cobalt, nickel, copper, and mixtures thereof;
$M^2$ is one or more additional metals, which have a total content of z;
R, if present, is an organic group;

L is a Lewis base;
n is 0 to about 1;
y is 0 to about 0.5, and
z is about 0.25 to about 0.9; and
x is about 0.5 to about 4.5;
wherein the metal hydride is capable of storing molecular hydrogen in an amount of at least 2% (based upon 100% total weight of the metal hydride without hydrogen stored in it) and reversibly releasing the hydrogen.

47. The metal hydride according to claim 9, wherein the metal hydride is capable of storing molecular hydrogen in an amount of at least 2% (based upon 100% total weight of the metal hydride without hydrogen stored in it) and reversibly releasing the hydrogen.

48. The metal hydride according to claim 9, wherein the metal hydride is substantially amorphous.

49. The metal hydride according to claim 9, wherein the metal hydride is stable as a bulk solid at room temperature.

50. The metal hydride according to claim 12, wherein the metal hydride is capable of storing molecular hydrogen in an amount of at least 2% (based upon 100% total weight of the metal hydride without hydrogen stored in it) and reversibly releasing the hydrogen.

51. The metal hydride according to claim 12, wherein the metal hydride is substantially amorphous.

52. The metal hydride according to claim 12, wherein hydrogenation and/or dehydrogenation of the metal hydride is thermodynamically neutral.

53. The metal hydride according to claim 12, wherein the metal hydride is stable as a bulk solid at room temperature.

54. The metal hydride according to claim 12, wherein the $H_2$ is coordinated with a metal center via a Kubas interaction.

55. The metal hydride according to claim 45, wherein the metal hydride is capable of storing molecular hydrogen in an amount of at least 2% (based upon 100% total weight of the metal hydride without hydrogen stored in it) and reversibly releasing the hydrogen.

56. The metal hydride according to claim 45, wherein the metal hydride is substantially amorphous.

57. The metal hydride according to claim 45, wherein hydrogenation and/or dehydrogenation of the metal hydride is thermodynamically neutral.

58. The metal hydride according to claim 45, wherein the metal hydride is stable as a bulk solid at room temperature.

59. The metal hydride according to claim 46, wherein the metal hydride is substantially amorphous.

60. The metal hydride according to claim 46, wherein hydrogenation and/or dehydrogenation of the metal hydride is thermodynamically neutral.

61. The metal hydride according to claim 46, wherein the metal hydride is stable as a bulk solid at room temperature.

62. The metal hydride according to claim 46, wherein $M^1$ is selected from vanadium, chromium, cobalt, copper, and mixtures thereof.

63. A metal hydride of the formula (III):

$$M^1(M^2)_zH_xR_yL_n \quad \text{(III)}$$

wherein
 $M^1$ is a first metal selected from titanium, vanadium, chromium, iron, cobalt, nickel, copper, and mixtures thereof;
 $M^2$ is one or more additional metals, which have a total content of z;
 R, if present, is an organic group;
 L is a Lewis base;
 n is 0 to about 1;
 y is 0 to about 0.5, and
 z is about 0.25 to about 0.9; and
 x is about 0.5 to about 4.5;
wherein the metal hydride is substantially amorphous.

64. The metal hydride according to claim 63, wherein hydrogenation and/or dehydrogenation of the metal hydride is thermodynamically neutral.

65. The metal hydride according to claim 63, wherein the metal hydride is stable as a bulk solid at room temperature.

66. The metal hydride according to claim 63, wherein the metal hydride is capable of storing molecular hydrogen in an amount of at least 3% (based upon 100% total weight of the metal hydride without hydrogen stored in it) and reversibly releasing the hydrogen.

* * * * *